(12) United States Patent
Franz et al.

(10) Patent No.: US 8,778,643 B2
(45) Date of Patent: Jul. 15, 2014

(54) METHODS FOR INCREASING LIPID LEVELS AND PRODUCING TRIACYLGLYCEROLS IN ALGAE

(71) Applicant: The Regents of the University of California, Oakland, CA (US)

(72) Inventors: Annaliese Kirsten Franz, Davis, CA (US); Megan Danielewicz, Davis, CA (US); Diana Meiying Wong, Davis, CA (US); Lisa Adele Anderson, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/802,136

(22) Filed: Mar. 13, 2013

(65) Prior Publication Data

US 2013/0273620 A1 Oct. 17, 2013

Related U.S. Application Data

(60) Provisional application No. 61/611,347, filed on Mar. 15, 2012.

(51) Int. Cl.
C12P 7/64 (2006.01)

(52) U.S. Cl.
USPC ........................................ 435/134; 435/244

(58) Field of Classification Search
USPC ...................... 435/134, 244, 255.1
See application file for complete search history.

(56) References Cited

U.S. PATENT DOCUMENTS 7,901,928 B2 3/2011 Yadav et al.
2011/0078946 A1 4/2011 Newell et al.

FOREIGN PATENT DOCUMENTS

WO 2010/132413 A1 11/2010

OTHER PUBLICATIONS

El-Baky H. et al. Evaluation of Marine Alga *Ulva lactuca* L. as a Source of Natural Preservative Ingredient. American Eurasian J Agriculture & Environmental Science 3(3)434-444, 2008.*
Mostafa S. Microalgal Biotechnology: Prospects and Applications Chapter 12, published by Intech, 2012.*
Herrero M. et al. Sub and Supercritical Fluid Extraction of Functional Ingredients from Different Natural Sources . . . Instituto de Fermentaciones Industriales Madrid Spain.*
International Search Report and Written Opinion received for PCT Patent Application No. PCT/US2013/031059, mailed on Jun. 28, 2013, 10 pages.
Avasthi et al., "A Chemical Screen Identifies Class A G-Protein Coupled Receptors As Regulators of Cilia", ACS Chemical Biology, vol. 7, 2012, pp. 911-919.
Bajguz et al., "Synergistic Effect of Auxins and Brassinosteroids on the Growth and Regulation of Metabolite Content in the Green Alga *Chlorella vulgaris* (Trebouxiophyceae)", Plant Physiology and Biochemistry, vol. 71, 2013, pp. 290-297.
Bishop et al., "The Effect of Chloramphenicol and Cycloheximide on Lipid Synthesis during Chloroplast Development in *Euglena gracilis*", Archives of Biochemistry and Biophysics, vol. 137, 1970, pp. 179-189.
Burns et al., "High-Throughput Screening of Small Molecules for Bioactivity and Target Identification in *Caenorhabditis elegans*", Nature Protocols, vol. 1, No. 4, 2006, pp. 1906-1914.
Chen et al., "A High Throughput Nile Red Method for Quantitative Measurement of Neutral Lipids in Microalgae", Journal of Microbiological Methods, vol. 77, 2009, pp. 41-47.
Dehesh et al., "Overexpression of 3-Ketoacyl-Acyl-Carrier Protein Synthase IIIs in Plants Reduces the Rate of Lipid Synthesis", Plant Physiology, vol. 125, Feb. 2001, pp. 1103-1114.
Garcia et al., "Mixotrophic Growth of the Microalga *Phaeodactylum tricornutum* Influence of Different Nitrogen and Organic Carbon Sources on Productivity and Biomass Composition", Process Biochemistry, vol. 40, 2005, pp. 297-305.
Gardner et al., "Use of Sodium Bicarbonate to Stimulate Triacylglycerol Accumulation in the *Chlorophyte scenedesmus* sp. and the Diatom *Phaeodactylum tricornutum*", J Appl Phycol, vol. 24, 2012, pp. 1311-1320.
Huang et al., "Rapid Screening Method for Lipid Production in Alga Based on Nile Red Fluorescence", Biomass and Bioenergy, vol. 33, 2009, pp. 1386-1392.
Jain et al., "Enhancement of Seed Oil Content by Expression of Glycerol-3-Phosphate Acyltransferase Genes", Biochemical Society Transactions, vol. 28, No. 6, 2000, pp. 958-961.
Jay, A. El, "Effects of Organic Solvents and Solvent-Atrazine Interactions on Two Algae, *Chlorella vulgaris* and *Selenastrum capricornutum*", Archives of Environmental Contamination and Toxicology, vol. 31, 1996, pp. 84-90.
Kamiyama et al., "In vitro Inhibition of α-Glucosidases and Glycogen Phosphorylase by Catechin Gallates in Green Tea", Food Chemistry, vol. 122, 2010, pp. 1061-1066.
Kilian et al., "High-Efficiency Homologous Recombination in the Oil-Producing Alga *Nannochloropsis* Sp.", PNAS, vol. 108, No. 52, Dec. 27, 2011, pp. 21265-21269.
Kim et al., "Combinatorial Solid-Phase Synthesis of 4,6-Diaryl and 4-Aryl, 6-Alkyl-1,3,5-triazines and their Application to Efficient Biofuel Production", ACS Combinatorial Science, vol. 14, 2012, pp. 395-398.

(Continued)

*Primary Examiner* — Ralph Gitomer
(74) *Attorney, Agent, or Firm* — Morrison & Foerster LLP

(57) ABSTRACT

The present disclosure relates to methods of increasing lipid levels in an algal or yeast cell population, methods of producing saturated or monounsaturated triacylglycerols in an algal or yeast cell population, and methods of decreasing polyunsaturated triacylglycerol production in an algal or yeast cell population by contacting the cell population with a chemical compound that is capable of increasing lipid levels or altering the lipid composition in the cell population.

17 Claims, 24 Drawing Sheets

(56) References Cited

OTHER PUBLICATIONS

Lambert et al., "Mechanisms of Cancer Prevention by Tea Constituents", Proceedings of the Third International Scientific Symposium on Tea and Human Health: Role of Flavonoids in the Diet, The Journal of Nutrition, vol. 133, 2003, pp. 3262S-3267S.

Lee et al., "Intracellular Dimethylsulfoxide (Dmso) in Unicellular Marine Algae: Speculations on its Origin and Possible Biological Role", J. Phycol., vol. 35, 1999, pp. 8-18.

Lemieux et al., "A Whole Organism Screen Identifies Novel Regulators of Fat Storage", Nat Chem Biol., vol. 7, No. 4, Apr. 2011, pp. 1-20.

Li et al., "Inhibition of Starch Synthesis Results in Overproduction of Lipids in *Chlamydomonas reinhardtii*", Biotechnology and Bioengineering, vol. 107, No. 2, Oct. 1, 2010, pp. 258-268.

Moellering et al., "RNA Interference Silencing of a Major Lipid Droplet Protein Affects Lipid Droplet Size in *Chlamydomonas reinhardtii*", Eukaryotic Cell, vol. 9, No. 1, Jan. 2010, pp. 97-106.

Molnar et al., "Highly Specific Gene Silencing by Artificial MicroRNAs in the Unicellular Alga *Chlamydomonas reinhardtii*", The Plant Journal, vol. 58, 2009, pp. 165-174.

Murphy et al., "Quantitative Analysis of Lipid Droplet Fusion: Inefficient Steady State Fusion but Rapid Stimulation by Chemical Fusogens", PLoS One, vol. 5, No. 12, Dec. 2010, p. e15030 (pp. 1-12).

Nakai et al., "Algal Growth Inhibition Effects and Inducement Modes by Plant-Producing Phenols", Wat. Res. vol. 35, No. 7, 2001, pp. 1855-1859.

Okumura et al., "Influence of Organic Solvents on the Growth of Marine Microalgae", Archives of Environmental Contamination and Toxicology, vol. 41, 2001, pp. 123-128.

Osundeko et al., "Oxidative Stress-Tolerant Microalgae Strains are Highly Efficient for Biofuel Feedstock Production on Wastewater", Biomass and Bioenergy, vol. 56, 2013, pp. 284-294.

Piotrowska et al., "The Effect of Indomethacin on the Growth and Metabolism of Green Alga *Chlorella vulgaris* Beijerinck", Plant Growth Regul, vol. 55, 2008, pp. 125-136.

Richardson et al., "Effects of Nitrogen Limitation on the Growth and Composition of Unicellular Algae in Continuous Culture", Applied Microbiology, vol. 18, No. 2, Aug. 1969, pp. 245-250.

Roesler et al., "Targeting of the Arabidopsis Homomeric Acetyl-Coenzyme A Carboxylase to Plastids of Rapeseeds", Plant Physiol., vol. 113, 1997, pp. 75-81.

Ryckebosch et al., "Optimization of an Analytical Procedure for Extraction of Lipids from Microalgae", Journal of the American Oil Chemists Society, Jul. 24, 2011, 10 pages.

Saffari et al., "Green Tea Metabolite EGCG Protects Membranes Against Oxidative Damage in vitro", Life Sciences, vol. 74, 2004, pp. 1513-1518.

Schimmel, Richard J., "Stimulation of cAMP Accumulation and Lipolysis in Hamster Adipocytes with Forskolin", The American Physiological Society, 1984, pp. C63-C68.

Siaut et al., "Oil Accumulation in the Model Green Alga *Chlamydomonas reinhardtii*: Characterization, Variability between Common Laboratory Strains and Relationship with Starch Reserves", BMC Biotechnology, vol. 11, No. 7, 2011, 15 pages.

Suen et al., "Total Lipid Production of the Green Alga *Nannochloropsis* Sp. QII Under Different Nitrogen Regimes", J. Phycol., vol. 23, 1987, pp. 289-296.

Sunda et al., "An Antioxidant Function for DMSP and DMS in Marine Algae", Letters to Nature, vol. 418, Jul. 18, 2002, pp. 317-320.

Tanaka et al., "Comparison of Three *Chlamydomonas* Strains which Show Distinctive Oxidative Stress Tolerance", Journal of Bioscience and Bioengineering, vol. 112, No. 5, 2011, pp. 462-468.

Vega et al., "Dimethyl Sulfoxide Enhances Lipid Synthesis and Secretion by Long-Term Cultures of Adult Rat Hepatocytes", Biochimie, vol. 73, 1991, pp. 621-624.

Vigeolas et al., "Increased Levels of Glycerol-3-Phosphate Lead to a Stimulation of Flux into Triacylglycerol Synthesis after Supplying Glycerol to Developing Seeds of *Brassica napus* L. in Planta", Planta, vol. 219, 2004, pp. 827-835.

Wang et al., "Algal Lipid Bodies: Stress Induction, Purification, and Biochemical Characterization in Wild-Type and Starchless *Chlamydomonas reinhardtii*", Eukaryotic Cell, vol. 8, No. 12, Dec. 2009, pp. 1856-1868.

Wang et al., "Green Tea Epigallocatechin Gallate: A Natural Inhibitor of Fatty-Acid Synthase", Biochemical and Biophysical Research Communications, vol. 288, 2001, pp. 1200-1206.

White et al., "The Effect of Sodium Bicarbonate Supplementation on Growth and Biochemical Composition of Marine Microalgae Cultures", J Appl Phycol., vol. 25, 2013, pp. 153-165.

Yu et al., "Modifications of the Metabolic Pathways of Lipid and Triacylglycerol Production in Microalgae", Microbial Cell Factories, vol. 10, No. 91, 2011, 11 pages.

Zou et al., "Modification of Seed Oil Content and Acyl Composition in the *Brassicaceae* by Expression of a Yeast sn-2 Acyltransferase Gene", The Plant Cell, vol. 9, Jun. 1997, pp. 909-923.

\* cited by examiner

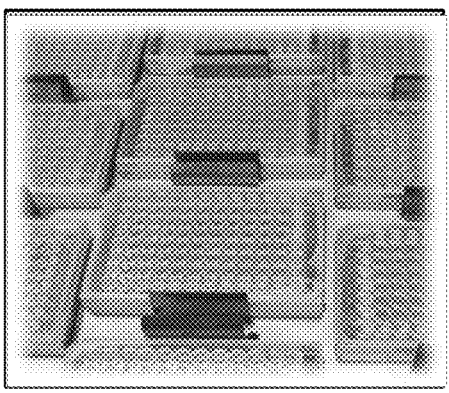

Phase 1: 54 Compound Assay

54 or more compounds
3x assay plate per Algae
1x control plate per Algae
4 different algae screened
Nile Red lipid analysis

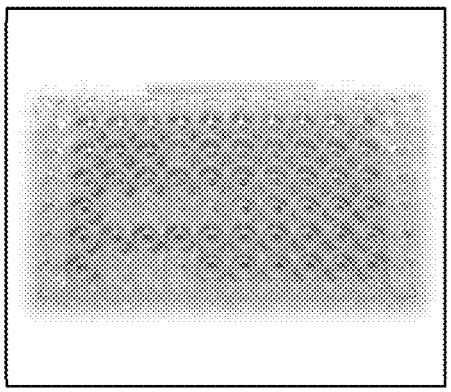

Phase 2: Lead Compounds

12+ Lead Focus Compounds
6 compounds per plate
9 Dose Response Concentrations
3x using DMSO delivery
3x using $H_2O$ delivery
2x control plate per algae
4 different Algae screened
Nile Red lipid analysis

Phase 3: Batch Cultures

5-10 Selected Lead Compounds
1 compound per flask
3 replicates
1 control flask
4 different algae screened
Aliquots analyzed with Nile Red

*Lipid composition then extracted
and analyzed by NMR Spectroscopy
and Mass Spectrometry*

Figure 1B

| Algae | Molecule | Absorbance Percent Increase | Nile Red Fluorescence Percent Increase |
|---|---|---|---|
| P. tricornutum 40 µM | CDK2 Inhibitor II | -14.6 | 150.6 |
|  | Ethyl 3,4-dephostatin | -2.4 | 115.0 |
|  | SB202190 | +4.26 | 112.4 |
| P. tricornutum 200 nM | Benzylaminopurine | -14.6 | 105.9 |
|  | Forskolin | -1.2 | 103.6 |
|  | Abscisic acid | -1.2 | 87.0 |
|  | CDK2 Inhibitor II | -7.9 | 50.3 |
| N. salina 20 µM | PTP Inhibitor II | +14.0 | 57.6 |
|  | Bohemine | +6.7 | 50.9 |
| N. salina 200 nM | BPDQ | -6.7 | 54.9 |
| Nannochloris sp. 20 µM | EGCG | +1.9 | 92.5 |
|  | Aloisine A | -12.6 | 84.1 |
|  | Arctigenin | -5.4 | 79.0 |
|  | Ethyl palmitate | -8.5 | 65.9 |
|  | Apigenin | -7.3 | 59.9 |
| Nannochloris sp. 200 nM | Cycloheximide | -12.4 | 178.1 |
|  | Bohemine | -12.1 | 150.4 |
|  | Alosine A | -5.4 | 125.9 |
|  | Thiamine | -12.1 | 122.6 |
|  | Rapamycin | -5.9 | 107.9 |
|  | CDK2 Inhibitor II | -14.0 | 103.2 |
|  | Cerulenin | -13.2 | 94.6 |
|  | EGCG | -1.0 | 92.1 |
|  | Erbstatin analog | -7.6 | 90.7 |
|  | Jasmonic acid | -7.6 | 87.5 |
|  | Atrazine | -1.7 | 86.2 |
|  | Kenpaullone | -8.1 | 77.5 |
|  | BPDQ | -6.5 | 75.8 |
|  | Kinetin | -9.0 | 72.4 |
|  | Giberellic Acid | -1.1 | 70.4 |
|  | Acetaminophen | -6.7 | 68.9 |
|  | Arctigenin | -3.4 | 66.0 |
|  | Cantharidin | -6.5 | 64.5 |
|  | Quercetin | -1.6 | 63.5 |
|  | Abscisic acid | -2.6 | 61.6 |
|  | Forskolin | -5.5 | 60.6 |
|  | Caffeine | -7.5 | 60.4 |
|  | Citric Acid | -6.5 | 55.1 |
| N. oculata 20 µM | Forskolin | -17.3 | 50.4 |

Figure 4

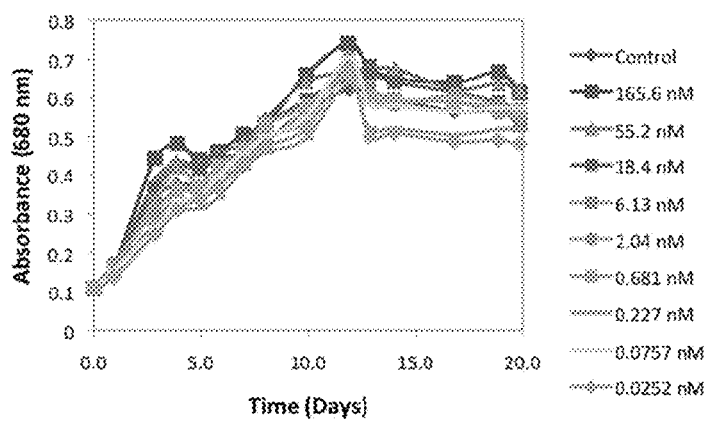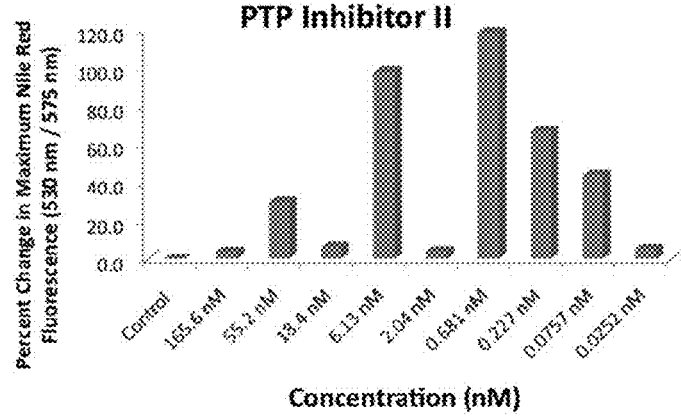
Figure 12

|  | Control | DMSO (0.4%) | 400 nM EGCG |
|---|---|---|---|
| Absorbance at harvest | 1.532 | 2.031 | 2.178 |
| Dry Weight (mg) | 713.7 | 613.4 | 905.85 ± 32.31 |
| Recovered Weight (mg) | 648 | 571.2 | 860.75 ± 27.22 |
| Biomass increase compared to control | 0 | 0-33 | 23-42 |
| Extract Weight (mg) | 30.2 | 40.3 | 62.50 ± 1.14 |
| Lipid increase compared to control | 0 | 33.4 | 106.5 ± 4.9 |

METHODS FOR INCREASING LIPID LEVELS AND PRODUCING TRIACYLGLYCEROLS IN ALGAE

CROSS-REFERENCE TO RELATED APPLICATIONS

This application claims the benefit of U.S. Provisional Application No. 61/611,347, filed Mar. 15, 2012, which is hereby incorporated by reference, in its entirety.

FIELD

The present disclosure relates to lipid levels in algae and yeast. In particular, the present disclosure relates to methods of increasing lipid levels in an algal or yeast cell population, methods of producing saturated or monounsaturated triacylglycerols in an algal or yeast cell population, and methods of decreasing polyunsaturated triacylglycerol production in an algal or yeast cell population by contacting the cell population with a chemical compound that is capable of increasing lipid levels or altering the lipid composition in the cell population.

BACKGROUND

Many strains of microalgae are efficient producers of triacylglycerols, which can be converted for use as biodiesel (Sheehan et al., *National Renewable Energy Laboratory*, 328, 1998). Algae have been identified as a viable feedstock for biofuels due to their efficient abilities to convert sunlight and $CO_2$ to biomass, synthesize large quantities of lipids (20-75% dry mass), thrive in saline water, grow on non-arable land, and grow in open or closed systems (Sheehan, J et al., *National Renewable Energy Laboratory*, 328, 1998; Huang, G et al., *Applied Energy*, 1-9, 2009; Rodolfi, L et al., *Biotechnol. Bioeng.* 102, 100-112, 2009; Hu, Q et al. *Plant J* 54, 621-639, 2008; and Spolaore, P. et al., *J. Biosci. Bioeng.* 101, 87-96, 2006). Microalgae are considered to be superior oil-producers compared to terrestrial competitors (e.g. corn, palm, rapeseed, jatropha, and soybean) because microalgae devote fewer resources to the synthesis of structural components such as cellulose and lignin (Song D. et al., *Chin J Biotechnol* 24, 341-348, 2008; Chisti, Y et al., *Biotechnol. Adv.* 25, 294-306, 2007; and Chisti, Y et al. *Trends Biotechnol.* 26, 126-131, 2008). While nitrogen-deficient conditions lead to an increase in lipid/cell, there is an overall decrease in the growth and cell-mass produced. Due to the commercial applications of these algae, there is a need to develop a better understanding of their metabolic pathways. Furthermore, a need exists for the development of novel ways to increase triacylglycerol production from algae that are economically competitive and sustainable. One solution for achieving this is to understand and control lipid-producing pathways.

Techniques for increasing lipid production in microalgae include nutrient-limitation and genetic engineering techniques for increasing lipid production in microalgae (James, G O et al., *Bioresour. Technol.* 102, 3343-3351, 2011; Wang, Z T et al., *Eukaryotic Cell* 8, 1856-1868, 2009; Lamers, P P et al., *Biotechnol. Bioeng.* doi:10.1002/bit.22725, 2010; Richardson, B et al., *Applied and Environmental Microbiology* 18, 245-250, 1969; Suen, Y et al., *J Phycol* 23, 289-296, 1987; Zhila, N O et al., *Botryococcus. J. Appl. Phycol.* 17, 309-315, 2005; Siaut, M et al., *BMC Biotechnology* 11, 7, 2011; and Li, Y et al., *Biotechnol. Bioeng.* 107, 258-268, 2010). However, these techniques do not allow for real-time, reversible, or temporal control at various stages of cell growth, and require genetic and biochemical knowledge of the pathways involved in lipid production. Moreover, nutrient-limitation also results in lower cell density.

The use of chemical genetics overcomes the problems of nutrient-limitation and genetic engineering techniques by utilizing a phenotypic approach to identify pathways of interest in lipid production that allows for probing of algae biology. Chemical genetics involves the systematic use of small molecules to modify protein function in real-time, rather than genetic mutation methods to disrupt gene function (Schreiber, S, *Nat Chem Biol*, 2005; Walsh, D P et al., *Chem. Rev.* 106, 2476-2530, 2006; and Stockwell, B R, *Nature*, 2004). Additionally, chemical genetics have several advantages over classical genetics, including: 1) real-time control, 2) reversible and temporal control at variable stages of cell growth, 3) access to a "partial knockout" based on concentration effects, 4) overcoming genetic redundancy, and 5) performing sequential treatments of small molecules to accomplish the effect of multiple mutations (Lehár, J et al, *Nat Chem Biol* 4, 674-681, 2008).

Moreover, while U.S. Patent Application Publication No. US 2011/0078946 disclose the use of compounds that inhibit fatty acid metabolism, such as gluconeogenesis inhibitors, fatty acid oxidation inhibitors, fatty acid transporter inhibitors, reductase inhibitors, isomerase inhibitors, and uncoupling protein inhibitors, to promote the accumulation or storage of fatty acids in plants, algae, or fungi; these compounds only target a single metabolic pathway.

Accordingly there exists a need for the development of a chemical genetics approach for identifying chemical compounds that that increase lipid production, without limiting cell growth or density in algae and yeast, and to increase growth rate in algae and yeast by targeting additional biochemical signaling pathways that control fatty acid and triacylglycerol biosynthesis, storage, and metabolism.

SUMMARY

In order to meet the above needs, the present disclosure provides novel methods of increasing lipid levels, of producing saturated triacylglycerols or monounsaturated triacylglycerols, and of decreasing polyunsaturated triacylglycerol production in algae by contacting the algae with one or more chemical compounds that increase lipid levels and alter lipid composition in algae. Moreover, the present disclosure is based, at least in part, on the use of a novel three-phase process with microalgae to identify small molecule compounds that target novel pathways involved in fatty acid and triacylglycerol biosynthesis, storage, and metabolism, thereby increasing lipid levels and growth rate, and alter the lipid composition in algae (FIG. 1). Advantageously, identified compounds can induce up to a four-fold increase in lipid levels in algae. Additionally, identified compounds were capable of inducing the production of saturated and monounsaturated triacylglycerols, and decrease the production of polyunsaturated triacylglycerols in algae. Such triacylglycerols can be used for the production of better quality biofuels, as polyunsaturated triacylglycerols generally lower ignition quality and are prone to oxidation, which can ultimately lead to hydroperioxide polymers that inhibit engine performance.

Accordingly, one aspect of the present disclosure provides a method of increasing lipid levels in a cell population, by: (a) providing an algal or yeast cell population; and (b) contacting the cell population with at least one compound selected from Table 1 in an amount sufficient to increase lipid levels in the cell population, where the at least one compound does not inhibit fatty acid metabolism. Another aspect of the present disclosure provides a method of increasing lipid levels in a cell population, by: contacting an algal or yeast cell population with at least one compound selected from Table 1 in an amount sufficient to increase lipid levels in the cell population, where the at least one compound does not inhibit fatty acid metabolism. Another aspect of the present disclosure provides a method of producing saturated or monounsaturated triacylglycerols in a cell population, by: contacting an algal or yeast cell population with at least one compound selected from Table 1 in an amount sufficient to induce production of one or more saturated or monounsaturated triacylglycerols in the cell population. Another aspect of the present disclosure provides a method of producing saturated or monounsaturated triacylglycerols in a cell population, by: (a) providing an algal cell population or a yeast cell population; and (b) contacting the cell population with at least one compound selected from Table 1 in an amount sufficient to induce production of one or more saturated or monounsaturated triacylglycerols in the cell population. In certain embodiments the cell population is an algal cell population. In certain embodiments the cell population is a yeast cell population. In certain embodiments the at least one compound includes a lipoxygenase inhibitor selected from curcumin, caffeic acid, baicalein, esculetin, and gossypol. In certain embodiments the at least one compound includes a tyrosine phosphatase inhibitor selected from PTP Inhibitor II, ethyl 3,4-dephostatin, cantharidin, napthyl acid phosphate, dephostatin, and 3,4-dephostatin. In certain embodiments the at least one compound includes a kinase inhibitor or kinase activator selected from t BPDQ, genistein, butein, emodin, piceatannol, quinazoline, and BPIQ-II, forskolin, SB202190, pd98059, 4-amino-5-(4-chlorophenyl)-7-(t-butyl)pyrazolo[3,4-d]pyrimidine, bisindolylmaleimide, bohemine, kenpaullone, BPIQ-II, CDK2 Inhibitor II, aloisine A, CDK4 Inhibitor I, cAMP, CDK4 Inhibitor 4, AICAR, CDK4 Inhibitor 3, and CDK4/6 Inhibitor 4. In certain embodiments the at least one compound includes a lipase inhibitor selected from RHC80267, orlistat, JZL 184 hydrate, halopemide, PTFK, edelfosine, pristimerin, disulfuram, octhilinone, and (2-butoxyphenyl)boronic acid. In certain embodiments the at least one compound includes an oxidative signaling compound selected from resveratrol, (+)-catechin, (−)-epicatechin gallate, (−)-epigallocatechin, (−)-epigallocatechin gallate, BHA, propyl gallate, ascorbic acid, N,N'-di-sec-butyl-p-phenylenediamine, α-D-tocopherol, quinacrine, chlorogenic acid, luteolin, NOX Inhibitor III, sulfasalazine, 2-amino-1,2,4-triazole, apocynin, cytochrome P450 1B1 inhibitor, DL-α-lipoic acid, formononetin, glutathione monoethyl ester, LY 231617, MCI-186, N-tert-butyl-α-phenylnitrone, U-74389G, and quercetin. In certain embodiments the at least one compound includes one of the group of CDK2 Inhibitor 2, CDK4 Inhibitor 1, gossypol, baicalein, AICAR, epigallocatechin gallate, SB202190, forskolin, cAMP, quinazoline, piceatannol, CDK4 Inhibitor 4, indomethacin, caffeic acid, PTP Inhibitor II, quinacrine, cycloheximide, BPDQ, butein, ethyl 3,4-dephostatin, cantharidin, JZL 184 hydrate, halopemide, BHA, resveratrol, propyl gallate, (−)-epigallocatechin, and (−)-epicatechin gallate. In certain embodiments the at least one compound is selected from a plant extract, a fruit extract, grape pomace, olive pomace, and tea extract. In certain embodiments the at least one compound includes two, three, four, or five compounds. In certain embodiments the at least one compound is present in an amount sufficient to increase growth rate of the cell population. In certain embodiments the cell population is grown under nutrient-deficient conditions. In certain embodiments the at least one compound is present in an amount sufficient to decrease growth rate of the cell population. In certain embodiments the cell population is contacted with the at least one compound during lag growth phase. In certain embodiments the cell population is contacted with the at least one compound during exponential growth phase. In certain embodiments the increased lipid levels comprise increased triacylglycerol levels. In certain embodiments the lipid levels in the cell population are increased by 40% to 400% as compared to a corresponding cell population not contacted with the at least one compound. In certain embodiments the lipid levels in the cell population are increased by at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 325%, at least 350%, at least 375%, at least 380%, at least 390%, at least 400%, at least 415%, at least 425%, at least 450%, at least 475%, or at least 500% compared to a corresponding cell population not contacted with the at least one inhibitor or compound. In certain embodiments that may be combined with any of the preceding embodiments, the method further includes producing a biofuel from the lipids.

Another aspect of the present disclosure provides a method of increasing lipid levels in an algal cell population, by: (a) providing an algal cell population; and (b) contacting the algal cell population with at least one lipoxygenase inhibitor in an amount sufficient for the at least one lipoxygenase inhibitor to increase lipid levels in the algal cell population, where the at least one lipoxygenase inhibitor does not inhibit fatty acid metabolism. In certain embodiments, the at least one lipoxygenase inhibitor is selected from lipoxygenase inhibitors listed in Table 2. In certain embodiments, the at least one lipoxygenase inhibitor is baicalein. In certain embodiments, the at least one lipoxygenase inhibitor is caffeic acid. In certain embodiments, the at least one lipoxygenase inhibitor is gossypol.

Another aspect of the present disclosure provides a method of increasing lipid levels in an algal cell population, by: (a) providing an algal cell population; and (b) contacting the algal cell population with at least one kinase inhibitor in an amount sufficient for the at least one kinase inhibitor to increase lipid levels in the algal cell population, where the at least one kinase inhibitor does not inhibit fatty acid metabolism. In certain embodiments, the at least one kinase inhibitor is selected from kinase inhibitors listed in Table 3. In certain embodiments, the at least one kinase inhibitor is BPDQ. In certain embodiments, the at least one kinase inhibitor is piceatannol. In certain embodiments, the at least one kinase inhibitor is butein.

Another aspect of the present disclosure provides a method of increasing lipid levels in an algal cell population, by: (a) providing an algal cell population; and (b) contacting the algal cell population with at least one phosphatase inhibitor in an amount sufficient for the at least one phosphatase inhibitor to increase lipid levels in the algal cell population, where the at least one phosphatase inhibitor does not inhibit fatty acid metabolism. In certain embodiments, the at least one phosphatase inhibitor is selected from phosphatase inhibitors listed in Table 4. In certain embodiments, the at least one phosphatase inhibitor is PTP Inhibitor II. In certain embodiments, the at least one phosphatase inhibitor is ethyl 3,4-dephostatin. In certain embodiments, where the at least one phosphatase inhibitor is cantharidin.

Another aspect of the present disclosure provides a method of increasing lipid levels in an algal cell population, by: (a)

providing an algal cell population; and (b) contacting the algal cell population with at least one kinase inhibitor in an amount sufficient for the at least one kinase inhibitor to increase lipid levels in the algal cell population, where the at least one kinase inhibitor does not inhibit fatty acid metabolism. Another aspect of the present disclosure provides a method of increasing lipid levels in an algal cell population, by: (a) providing an algal cell population; and (b) contacting the algal cell population with at least one kinase activator in an amount sufficient for the at least one kinase activator to increase lipid levels in the algal cell population, where the at least one kinase activator does not inhibit fatty acid metabolism. In certain embodiments that may be combined with any of the preceding embodiments, the at least one kinase inhibitor or kinase activator is selected from kinase inhibitors or activators listed in Table 5.

Another aspect of the present disclosure provides a method of increasing lipid levels in an algal cell population, by: (a) providing an algal cell population; and (b) contacting the algal cell population with at least one lipase inhibitor in an amount sufficient for the at least one lipase inhibitor to increase lipid levels in the algal cell population, where the at least one lipase inhibitor does not inhibit fatty acid metabolism. In certain embodiments, the at least one lipase inhibitor is selected from lipase inhibitors listed in Table 6. In certain embodiments, the at least one lipase inhibitor is JZL 184 hydrate. In certain embodiments, the at least one lipase inhibitor is halopemide.

Another aspect of the present disclosure provides a method of increasing lipid levels in an algal cell population, by: (a) providing an algal cell population; and (b) contacting the algal cell population with at least one oxidative signaling compound in an amount sufficient for the at least one oxidative signaling compound to increase lipid levels in the algal cell population, where the at least one oxidative signaling compound does not inhibit fatty acid metabolism. In certain embodiments, the at least one oxidative signaling compound is an antioxidant. In certain embodiments, the at least one oxidative signaling compound is selected from oxidative signaling compounds listed in Table 7. In certain embodiments, the at least one oxidative signaling compound is BHA. In certain embodiments, the at least one oxidative signaling compound is resveratol. In certain embodiments, the at least one oxidative signaling compound is propyl gallate. In certain embodiments, the at least one oxidative signaling compound is (−)-epigallocatechin. In certain embodiments, the at least one oxidative signaling compound is (−)-epicatechin gallate. In certain embodiments, the at least one oxidative signaling compound is selected from a plant extract, a fruit extract, grape pomace, olive pomace, and tea extract.

Another aspect of the present disclosure provides a method of increasing lipid levels in an algal cell population, by: (a) providing an algal cell population; and (b) contacting the algal cell population with at least one compound selected from the compounds listed in Table 1 in an amount sufficient for the at least one compound to increase lipid levels in the algal cell population, where the at least one compound does not inhibit fatty acid metabolism. Another aspect of the present disclosure provides a method of increasing lipid levels in an algal cell population, by: (a) providing an algal cell population; and (b) contacting the algal cell population with at least one compound, where the at least one compound increases lipid levels in the algal cell population, where the at least one compound is not derived from a biohydrogen waste stream, and where the at least one compound does not inhibit fatty acid metabolism. In certain embodiments, the at least one compound is selected from the compounds listed in Table 1.

In certain embodiments that may be combined with any of the preceding embodiments, the at least one compound is selected from a lipoxygenase inhibitor, a kinase inhibitor, a phosphatase inhibitor, a lipase inhibitor, and an oxidative signaling compound. In certain embodiments that may be combined with any of the preceding embodiments, the at least one compound is CDK2 Inhibitor 2. In certain embodiments that may be combined with any of the preceding embodiments, the at least one compound is CDK4 Inhibitor 1. In certain embodiments that may be combined with any of the preceding embodiments, the at least one compound is gossypol. In certain embodiments that may be combined with any of the preceding embodiments, the at least one compound is baicalein. In certain embodiments that may be combined with any of the preceding embodiments, the at least one compound is AICAR. In certain embodiments that may be combined with any of the preceding embodiments, the at least one compound is epigallocatechin gallate. In certain embodiments that may be combined with any of the preceding embodiments, the at least one compound is SB202190. In certain embodiments that may be combined with any of the preceding embodiments, the at least one compound is forskolin. In certain embodiments that may be combined with any of the preceding embodiments, the at least one compound is cAMP. In certain embodiments that may be combined with any of the preceding embodiments, the at least one compound is quinazoline. In certain embodiments that may be combined with any of the preceding embodiments, the at least one oxidative signaling compound is piceatannol. In certain embodiments that may be combined with any of the preceding embodiments, the at least one compound is CDK4 Inhibitor 4. In certain embodiments that may be combined with any of the preceding embodiments, the at least one compound is indomethacin. In certain embodiments that may be combined with any of the preceding embodiments, the at least one compound is caffeic acid. In certain embodiments that may be combined with any of the preceding embodiments, the at least one compound is PTP Inhibitor II. In certain embodiments that may be combined with any of the preceding embodiments, the at least one compound is quinacrine. In certain embodiments that may be combined with any of the preceding embodiments, the at least one compound is cycloheximide. In certain embodiments that may be combined with any of the preceding embodiments, the at least one compound is BPDQ. In certain embodiments that may be combined with any of the preceding embodiments, the at least one compound is butein. In certain embodiments that may be combined with any of the preceding embodiments, the at least one compound is ethyl 3,4-dephostatin. In certain embodiments that may be combined with any of the preceding embodiments, the at least one compound is cantharidin. In certain embodiments that may be combined with any of the preceding embodiments, the at least one compound is JZL 184 hydrate. In certain embodiments that may be combined with any of the preceding embodiments, the at least one compound is halopemide. In certain embodiments that may be combined with any of the preceding embodiments, the at least one compound is BHA. In certain embodiments that may be combined with any of the preceding embodiments, the at least one compound is resveratol. In certain embodiments that may be combined with any of the preceding embodiments, the at least one compound is propyl gallate. In certain embodiments that may be combined with any of the preceding embodiments, the at least one compound is (−)-epigallocatechin. In certain embodiments that may be combined with any of the preceding embodiments, the at least one compound is (−)-epicatechin gallate. In certain embodiments that may be combined with any of the preceding embodiments, the algal cell population is contacted with the at least one compound in an amount sufficient for the at least one compound to increase lipid levels in the algal cell population.

In certain embodiments that may be combined with any of the preceding embodiments, the at least one inhibitor or compound is at least two, at least three, at least four, or at least five inhibitors or compounds. In certain embodiments that may be combined with any of the preceding embodiments, the at least one inhibitor or compound further increases algal cell growth rate. In certain embodiments that may be combined with any of the preceding embodiments, the at least one inhibitor or compound is selected from the compounds listed in Table 8. In certain embodiments that may be combined with any of the preceding embodiments, the at least one inhibitor or compound further decreases algal cell growth rate. In certain embodiments that may be combined with any of the preceding embodiments, the algal cell population is contacted with the at least one inhibitor or compound during lag growth phase. In certain embodiments that may be combined with any of the preceding embodiments, the algal cell population is contacted with the at least one inhibitor or compound during exponential growth phase. In certain embodiments that may be combined with any of the preceding embodiments, the increased lipid levels are increased triacylglycerol levels. In certain embodiments, the increased triacylglycerol levels are increased saturated fatty acid levels or monounsaturated fatty acid levels. In certain embodiments, the saturated fatty acid has a carbon chain-length of at least 12 carbons, at least 14 carbons, at least 16 carbons, at least 18 carbons, at least 20 carbons, at least 22 carbons, at least 24 carbons, at least 26 carbons, at least 28 carbons, or at least 30 carbons. In certain embodiments that may be combined with any of the preceding embodiments, the monounsaturated fatty acid has a carbon chain-length of at least 12 carbons, at least 14 carbons, at least 16 carbons, at least 18 carbons, at least 20 carbons, at least 22 carbons, at least 24 carbons, at least 26 carbons, at least 28 carbons, or at least 30 carbons. In certain embodiments that may be combined with any of the preceding embodiments, lipid levels in the algal cell population are increased by at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 325%, at least 350%, at least 375%, at least 380%, at least 390%, at least 400%, at least 415%, at least 425%, at least 450%, at least 475%, or at least 500% compared to a corresponding algal cell population not contacted with the at least one inhibitor or compound. In certain embodiments that may be combined with any of the preceding embodiments, where the method further includes producing a biofuel from the lipids. In certain embodiments, the biofuel is a biodiesel.

Another aspect of the present disclosure provides a method of producing saturated or monounsaturated triacylglycerols in an algal cell population, by: (a) providing an algal cell population; and (b) contacting the algal cell population with at least one lipoxygenase inhibitor in an amount sufficient for the at least one lipoxygenase inhibitor to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one lipoxygenase inhibitor in an amount sufficient for the at least one lipoxygenase inhibitor to decrease polyunsaturated triacylglycerol production in the algal cell population compared to a corresponding algal cell population not contacted with the at least one lipoxygenase inhibitor. In certain embodiments that may be combined with any of the preceding embodiments, the at least one lipoxygenase inhibitor is selected from lipoxygenase inhibitors listed in Table 2.

Another aspect of the present disclosure provides a method of producing saturated or monounsaturated triacylglycerols in an algal cell population, by: (a) providing an algal cell population; and (b) contacting the algal cell population with at least one kinase inhibitor in an amount sufficient for the at least one kinase inhibitor to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one kinase inhibitor in an amount sufficient for the at least one kinase inhibitor to decrease polyunsaturated triacylglycerol production in the algal cell population compared to a corresponding algal cell population not contacted with the at least one kinase inhibitor. In certain embodiments that may be combined with any of the preceding embodiments, the at least one kinase inhibitor is selected from kinase inhibitors listed in Table 3.

Another aspect of the present disclosure provides a method of producing saturated or monounsaturated triacylglycerols in an algal cell population, by: (a) providing an algal cell population; and (b) contacting the algal cell population with at least one phosphatase inhibitor in an amount sufficient for the at least one phosphatase inhibitor to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one phosphatase inhibitor in an amount sufficient for the at least one phosphatase inhibitor to decrease polyunsaturated triacylglycerol production in the algal cell population compared to a corresponding algal cell population not contacted with the at least one phosphatase inhibitor. In certain embodiments that may be combined with any of the preceding embodiments, the at least one phosphatase inhibitor is selected from phosphatase inhibitors listed in Table 4.

Another aspect of the present disclosure provides a method of producing saturated or monounsaturated triacylglycerols in an algal cell population, by: (a) providing an algal cell population; and (b) contacting the algal cell population with at least one kinase inhibitor in an amount sufficient for the at least one kinase inhibitor to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one kinase inhibitor in an amount sufficient for the at least one kinase inhibitor to decrease polyunsaturated triacylglycerol production in the algal cell population compared to a corresponding algal cell population not contacted with the at least one kinase inhibitor. Another aspect of the present disclosure provides a method of producing saturated or monounsaturated triacylglycerols in an algal cell population, by: (a) providing an algal cell population; and (b) contacting the algal cell population with at least one kinase activator in an amount sufficient for the at least one kinase activator to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one kinase activator in an amount sufficient for the at least one kinase activator to decrease polyunsaturated triacylglycerol production in the algal cell population compared to a corresponding algal cell population not contacted with the at least one kinase activator. In certain embodiments that may be combined with any of the preceding embodiments, the at least one kinase inhibitor or kinase activator is selected from kinase inhibitors or activators listed in Table 5.

Another aspect of the present disclosure provides a method of producing saturated or monounsaturated triacylglycerols in an algal cell population, by: (a) providing an algal cell population; and (b) contacting the algal cell population with at least one lipase inhibitor in an amount sufficient for the at least one lipase inhibitor to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one lipase inhibitor in an amount sufficient for the at least one lipase inhibitor to decrease polyunsaturated triacylglycerol production in the algal cell population compared to a corresponding algal cell population not contacted with the at least one lipase inhibitor. In certain embodiments that may be combined with any of the preceding embodiments, the at least one lipase inhibitor is selected from lipase inhibitors listed in Table 6.

Another aspect of the present disclosure provides a method of producing saturated or monounsaturated triacylglycerols in an algal cell population, by: (a) providing an algal cell population; and (b) contacting the algal cell population with at least one oxidative signaling compound in an amount sufficient for the at least one oxidative signaling compound to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one oxidative signaling compound in an amount sufficient for the at least one oxidative signaling compound to decrease polyunsaturated triacylglycerol production in the algal cell population compared to a corresponding algal cell population not contacted with the at least one oxidative signaling compound. In certain embodiments that may be combined with any of the preceding embodiments, the at least one oxidative signaling compound is an antioxidant. In certain embodiments that may be combined with any of the preceding embodiments, the at least one oxidative signaling compound is selected from oxidative signaling compounds listed in Table 7. In certain embodiments that may be combined with any of the preceding embodiments, the at least one oxidative signaling compound is selected from a plant extract, a fruit extract, grape pomace, olive pomace, and tea extract.

Another aspect of the present disclosure provides a method of producing saturated or monounsaturated triacylglycerols in an algal cell population, by: (a) providing an algal cell population; and (b) contacting the algal cell population with at least one compound selected from the compounds listed in Table 1 in an amount sufficient for the at least one compound to induce production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least one compound selected from the compounds listed in Table 1 in an amount sufficient for the at least one compound to decrease polyunsaturated triacylglycerol production in the algal cell population compared to a corresponding algal cell population not contacted with the at least one compound. Another aspect of the present disclosure provides a method of producing saturated or monounsaturated triacylglycerols in an algal cell population, by: (a) providing an algal cell population; and (b) contacting the algal cell population with at least one compound, where the at least one compound induces production of one or more saturated or monounsaturated triacylglycerols in the algal cell population. Another aspect of the present disclosure provides a method of decreasing polyunsaturated triacylglycerol production in an algal cell population, by: (a) providing an algal cell population; and (b) contacting the algal cell population with at least compound, where the at least one compound decreases polyunsaturated triacylglycerol production in the algal cell population compared to a corresponding algal cell population not contacted with the at least one compound.

In certain embodiments that may be combined with any of the preceding embodiments, the at least one compound is selected from the compounds listed in Table 1. In certain embodiments that may be combined with any of the preceding embodiments, the at least one compound is selected from a lipoxygenase inhibitor, a tyrosine kinase inhibitor, a phosphatase inhibitor, a lipase inhibitor, and an oxidative signaling compound. In certain embodiments that may be combined with any of the preceding embodiments, the at least one compound is cycloheximide. In certain embodiments that may be combined with any of the preceding embodiments, the at least one compound is glycerol. In certain embodiments that may be combined with any of the preceding embodiments, the at least one compound is quinacrine. In certain embodiments that may be combined with any of the preceding embodiments, the at least one compound is cAMP. In certain embodiments that may be combined with any of the preceding embodiments, the at least one compound is (−)-epigallocatechin gallate. In certain embodiments that may be combined with any of the preceding embodiments, the at least one compound is forskolin. In certain embodiments that may be combined with any of the preceding embodiments, the at least one compound is PTP Inhibitor II. In certain embodiments that may be combined with any of the preceding embodiments, the at least one oxidative signaling compound is orlistat.

In certain embodiments that may be combined with any of the preceding embodiments, the method further includes producing a biofuel from the produced saturated or monounsaturated triacylglycerols. In certain embodiments that may be combined with any of the preceding embodiments, the method further includes producing a biofuel from lipids produced by the algal cell population having decreased polyunsaturated triacylglycerol production. In certain embodiments that may be combined with any of the preceding embodiments, the biofuel is a biodiesel.

In certain embodiments that may be combined with any of the preceding embodiments, the algal cell population is a population of oleaginous algal cells. In certain embodiments that may be combined with any of the preceding embodiments, the population of oleaginous algal cells are selected from diatoms, green algae, blue-green algae, golden-brown algae, brown algae, red algae, and haptophytes.

Another aspect of the present disclosure provides a method of increasing lipid levels in a yeast cell population, by: (a) providing a yeast cell population; and (b) contacting the yeast cell population with at least one lipoxygenase inhibitor in an amount sufficient for the at least one lipoxygenase inhibitor to increase lipid levels in the yeast cell population, where the at least one lipoxygenase inhibitor does not inhibit fatty acid metabolism. In certain embodiments, the at least one lipoxygenase inhibitor is selected from lipoxygenase inhibitors listed in Table 2. In certain embodiments, the at least one lipoxygenase inhibitor is baicalein. In certain embodiments, the at least one lipoxygenase inhibitor is caffeic acid. In certain embodiments, the at least one lipoxygenase inhibitor is gossypol.

Another aspect of the present disclosure provides a method of increasing lipid levels in a yeast cell population, by: (a) providing a yeast cell population; and (b) contacting the yeast cell population with at least one kinase inhibitor in an amount sufficient for the at least one kinase inhibitor to increase lipid levels in the yeast cell population, where the at least one kinase inhibitor does not inhibit fatty acid metabolism. In certain embodiments, the at least one kinase inhibitor is selected from kinase inhibitors listed in Table 3. In certain embodiments, the at least one kinase inhibitor is BPDQ. In certain embodiments, the at least one kinase inhibitor is piceatannol. In certain embodiments, the at least one kinase inhibitor is butein.

Another aspect of the present disclosure provides a method of increasing lipid levels in a yeast cell population, by: (a) providing a yeast cell population; and (b) contacting the yeast cell population with at least one phosphatase inhibitor in an amount sufficient for the at least one phosphatase inhibitor to increase lipid levels in the yeast cell population, where the at least one phosphatase inhibitor does not inhibit fatty acid metabolism. In certain embodiments, the at least one phosphatase inhibitor is selected from phosphatase inhibitors listed in Table 4. In certain embodiments, the at least one phosphatase inhibitor is PTP Inhibitor II. In certain embodiments, the at least one phosphatase inhibitor is ethyl 3,4-dephostatin. In certain embodiments, the at least one phosphatase inhibitor is cantharidin.

Another aspect of the present disclosure provides a method of increasing lipid levels in a yeast cell population, by: (a) providing a yeast cell population; and (b) contacting the yeast cell population with at least one kinase inhibitor in an amount sufficient for the at least one kinase inhibitor to increase lipid levels in the yeast cell population, where the at least one kinase inhibitor does not inhibit fatty acid metabolism. Another aspect of the present disclosure provides a method of increasing lipid levels in a yeast cell population, by: (a) providing a yeast cell population; and (b) contacting the yeast cell population with at least one kinase activator in an amount sufficient for the at least one kinase activator to increase lipid levels in the yeast cell population, where the at least one kinase activator does not inhibit fatty acid metabolism. In certain embodiments that may be combined with any of the preceding embodiments, the at least one kinase inhibitor or kinase activator is selected from kinase inhibitors or activators listed in Table 5.

Another aspect of the present disclosure provides a method of increasing lipid levels in a yeast cell population, by: (a) providing a yeast cell population; and (b) contacting the yeast cell population with at least one lipase inhibitor in an amount sufficient for the at least one lipase inhibitor to increase lipid levels in the yeast cell population, where the at least one lipase inhibitor does not inhibit fatty acid metabolism. In certain embodiments, the at least one lipase inhibitor is selected from lipase inhibitors listed in Table 6. In certain embodiments, the at least one lipase inhibitor is JZL 184 hydrate. In certain embodiments, the at least one lipase inhibitor is halopemide.

Another aspect of the present disclosure provides a method of increasing lipid levels in a yeast cell population, by: (a) providing a yeast cell population; and (b) contacting the yeast cell population with at least one oxidative signaling compound in an amount sufficient for the at least one oxidative signaling compound to increase lipid levels in the yeast cell population, where the at least one oxidative signaling compound does not inhibit fatty acid metabolism. In certain embodiments, the at least one oxidative signaling compound is an antioxidant. In certain embodiments, the at least one oxidative signaling compound is selected from oxidative signaling compounds listed in Table 7. In certain embodiments, the at least one oxidative signaling compound is BHA. In certain embodiments, the at least one oxidative signaling compound is resveratol. In certain embodiments, the at least one oxidative signaling compound is propyl gallate. In certain embodiments, the at least one oxidative signaling compound is (−)-epigallocatechin. In certain embodiments, the at least one oxidative signaling compound is (−)-epicatechin gallate. In certain embodiments, the at least one oxidative signaling compound is selected from a plant extract, a fruit extract, grape pomace, olive pomace, and tea extract.

Another aspect of the present disclosure provides a method of increasing lipid levels in a yeast cell population, by: (a) providing a yeast cell population; and (b) contacting the yeast cell population with at least one compound selected from the compounds listed in Table 1 in an amount sufficient for the at least one compound to increase lipid levels in the yeast cell population, where the at least one compound does not inhibit fatty acid metabolism. Another aspect of the present disclosure provides a method of increasing lipid levels in a yeast cell population, by: (a) providing a yeast cell population; and (b) contacting the yeast cell population with at least one compound, where the at least one compound increases lipid levels in the yeast cell population, where the at least one compound is not derived from a biohydrogen waste stream, and where the at least one compound does not inhibit fatty acid metabolism. In certain embodiments, the at least one compound is selected from the compounds listed in Table 1.

In certain embodiments that may be combined with any of the preceding embodiments, the at least one compound is selected from a lipoxygenase inhibitor, a kinase inhibitor, a phosphatase inhibitor, a lipase inhibitor, and an oxidative signaling compound. In certain embodiments that may be combined with any of the preceding embodiments, the at least one compound is CDK2 Inhibitor 2. In certain embodiments that may be combined with any of the preceding embodiments, the at least one compound is CDK4 Inhibitor 1. In certain embodiments that may be combined with any of the preceding embodiments, the at least one compound is gossypol. In certain embodiments that may be combined with any of the preceding embodiments, the at least one compound is baicalein. In certain embodiments that may be combined with any of the preceding embodiments, the at least one compound is AICAR. In certain embodiments that may be combined with any of the preceding embodiments, the at least one compound is epigallocatechin gallate. In certain embodiments that may be combined with any of the preceding embodiments, the at least one compound is SB202190. In certain embodiments that may be combined with any of the preceding embodiments, the at least one compound is forskolin. In certain embodiments that may be combined with any of the preceding embodiments, the at least one compound is cAMP. In certain embodiments that may be combined with any of the preceding embodiments, the at least one compound is quinazoline. In certain embodiments that may be combined with any of the preceding embodiments, the at least one oxidative signaling compound is piceatannol. In certain embodiments that may be combined with any of the preceding embodiments, the at least one compound is CDK4 Inhibitor 4. In certain embodiments that may be combined with any of the preceding embodiments, the at least one compound is indomethacin. In certain embodiments that may be combined with any of the preceding embodiments, the at least one compound is caffeic acid. In certain embodiments that may be combined with any of the preceding embodiments, the at least one compound is PTP Inhibitor II. In certain embodiments that may be combined with any of the preceding embodiments, the at least one compound is quinacrine. In certain embodiments that may be combined with any of the preceding embodiments, the at least one compound is cycloheximide. In certain embodiments that may be combined with any of the preceding embodiments, the at least one compound is BPDQ. In certain embodiments that may be combined with any of the preceding embodiments, the at least one compound is butein. In certain embodiments that may be combined with any of the preceding embodiments, the at least one compound is ethyl 3,4-dephostatin. In certain embodiments that may be combined with any of the preceding embodiments, the at least one compound is cantharidin. In certain embodiments that may be combined with any of the preceding embodiments, the at least one compound is JZL 184 hydrate. In certain embodiments that may be combined with any of the preceding embodiments, the at least one compound is halopemide. In certain embodiments that may be combined with any of the preceding embodiments, the at least one compound is BHA. In certain embodiments that may be combined with any of the preceding embodiments, the at least one compound is resveratol. In certain embodiments that may be combined with any of the preceding embodiments, the at least one compound is propyl gallate. In certain embodiments that may be combined with any of the preceding embodiments, the at least one compound is (−)-epigallocatechin. In certain embodiments that may be combined with any of the preceding embodiments, the at least one compound is (−)-epicatechin gallate. In certain embodiments that may be combined with any of the preceding embodiments, the yeast cell population is contacted with the at least one compound in an amount sufficient for the at least one compound to increase lipid levels in the yeast cell population.

In certain embodiments that may be combined with any of the preceding embodiments, the at least one inhibitor or compound is at least two, at least three, at least four, or at least five compounds. In certain embodiments that may be combined with any of the preceding embodiments, the at least one inhibitor or compound further increases yeast cell growth rate. In certain embodiments that may be combined with any of the preceding embodiments, the at least one inhibitor or compound is selected from the compounds listed in Table 8. In certain embodiments that may be combined with any of the preceding embodiments, the at least one inhibitor or compound further decreases yeast cell growth rate. In certain embodiments that may be combined with any of the preceding embodiments, the yeast cell population is contacted with the at least one inhibitor or compound during lag growth phase. In certain embodiments that may be combined with any of the preceding embodiments, the yeast cell population is contacted with the at least one inhibitor or compound during exponential growth phase. In certain embodiments that may be combined with any of the preceding embodiments, the increased lipid levels are increased triacylglycerol levels. In certain embodiments, the increased triacylglycerol levels are increased saturated fatty acid levels or monounsaturated fatty acid levels. In certain embodiments, the saturated fatty acid has a carbon chain-length of at least 12 carbons, at least 14 carbons, at least 16 carbons, at least 18 carbons, at least 20 carbons, at least 22 carbons, at least 24 carbons, at least 26 carbons, at least 28 carbons, or at least 30 carbons. In certain embodiments that may be combined with any of the preceding embodiments, the monounsaturated fatty acid has a carbon chain-length of at least 12 carbons, at least 14 carbons, at least 16 carbons, at least 18 carbons, at least 20 carbons, at least 22 carbons, at least 24 carbons, at least 26 carbons, at least 28 carbons, or at least 30 carbons. In certain embodiments that may be combined with any of the preceding embodiments, lipid levels in the yeast cell population are increased by at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 325%, at least 350%, at least 375%, at least 380%, at least 390%, at least 400%, at least 415%, at least 425%, at least 450%, at least 475%, or at least 500% compared to a corresponding yeast cell population not contacted with the at least one inhibitor or compound. In certain embodiments that may be combined with any of the preceding embodiments, where the method further includes producing a biofuel from the lipids. In certain embodiments, the biofuel is a biodiesel.

Another aspect of the present disclosure provides a method of producing saturated or monounsaturated triacylglycerols in a yeast cell population, by: (a) providing a yeast cell population; and (b) contacting the yeast cell population with at least one lipoxygenase inhibitor in an amount sufficient for the at least one lipoxygenase inhibitor to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one lipoxygenase inhibitor in an amount sufficient for the at least one lipoxygenase inhibitor to decrease polyunsaturated triacylglycerol production in the yeast cell population compared to a corresponding yeast cell population not contacted with the at least one lipoxygenase inhibitor. In certain embodiments that may be combined with any of the preceding embodiments, the at least one lipoxygenase inhibitor is selected from lipoxygenase inhibitors listed in Table 2.

Another aspect of the present disclosure provides a method of producing saturated or monounsaturated triacylglycerols in a yeast cell population, by: (a) providing a yeast cell population; and (b) contacting the yeast cell population with at least one kinase inhibitor in an amount sufficient for the at least one kinase inhibitor to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one kinase inhibitor in an amount sufficient for the at least one kinase inhibitor to decrease polyunsaturated triacylglycerol production in the yeast cell population compared to a corresponding yeast cell population not contacted with the at least one kinase inhibitor. In certain embodiments that may be combined with any of the preceding embodiments, the at least one kinase inhibitor is selected from kinase inhibitors listed in Table 3.

Another aspect of the present disclosure provides a method of producing saturated or monounsaturated triacylglycerols in a yeast cell population, by: (a) providing a yeast cell population; and (b) contacting the yeast cell population with at least one phosphatase inhibitor in an amount sufficient for the at least one phosphatase inhibitor to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one phosphatase inhibitor in an amount sufficient for the at least one phosphatase inhibitor to decrease polyunsaturated triacylglycerol production in the yeast cell population compared to a corresponding yeast cell population not contacted with the at least one phosphatase inhibitor. In certain embodiments that may be combined with any of the preceding embodiments, the at least one phosphatase inhibitor is selected from phosphatase inhibitors listed in Table 4.

Another aspect of the present disclosure provides a method of producing saturated or monounsaturated triacylglycerols in a yeast cell population, by: (a) providing a yeast cell population; and (b) contacting the yeast cell population with at least one kinase inhibitor in an amount sufficient for the at least one kinase inhibitor to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one kinase inhibitor in an amount sufficient for the at least one kinase inhibitor to decrease polyunsaturated triacylglycerol production in the yeast cell population compared to a corresponding yeast cell population not contacted with the at least one kinase inhibitor. Another aspect of the present disclosure provides a method of producing saturated or monounsaturated triacylglycerols in a yeast cell population, by: (a) providing a yeast cell population; and (b) contacting the yeast cell population with at least one kinase activator in an amount sufficient for the at least one kinase activator to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one kinase activator in an amount sufficient for the at least one kinase activator to decrease polyunsaturated triacylglycerol production in the yeast cell population compared to a corresponding yeast cell population not contacted with the at least one kinase activator. In certain embodiments that may be combined with any of the preceding embodiments, the at least one kinase inhibitor or kinase activator is selected from kinase inhibitors or activators listed in Table 5.

Another aspect of the present disclosure provides a method of producing saturated or monounsaturated triacylglycerols in a yeast cell population, by: (a) providing a yeast cell population; and (b) contacting the yeast cell population with at least one lipase inhibitor in an amount sufficient for the at least one lipase inhibitor to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one lipase inhibitor in an amount sufficient for the at least one lipase inhibitor to decrease polyunsaturated triacylglycerol production in the yeast cell population compared to a corresponding yeast cell population not contacted with the at least one lipase inhibitor. In certain embodiments that may be combined with any of the preceding embodiments, the at least one lipase inhibitor is selected from lipase inhibitors listed in Table 6.

Another aspect of the present disclosure provides a method of producing saturated or monounsaturated triacylglycerols in a yeast cell population, by: (a) providing a yeast cell population; and (b) contacting the yeast cell population with at least one oxidative signaling compound in an amount sufficient for the at least one oxidative signaling compound to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one oxidative signaling compound in an amount sufficient for the at least one oxidative signaling compound to decrease polyunsaturated triacylglycerol production in the yeast cell population compared to a corresponding yeast cell population not contacted with the at least one oxidative signaling compound. In certain embodiments that may be combined with any of the preceding embodiments, the at least one oxidative signaling compound is an antioxidant. In certain embodiments that may be combined with any of the preceding embodiments, the at least one oxidative signaling compound is selected from oxidative signaling compounds listed in Table 7. In certain embodiments that may be combined with any of the preceding embodiments, the at least one oxidative signaling compound is selected from a plant extract, a fruit extract, grape pomace, olive pomace, and tea extract.

Another aspect of the present disclosure provides a method of producing saturated or monounsaturated triacylglycerols in a yeast cell population, by: (a) providing a yeast cell population; and (b) contacting the yeast cell population with at least one compound selected from the compounds listed in Table 1 in an amount sufficient for the at least one compound to induce production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least one compound selected from the compounds listed in Table 1 in an amount sufficient for the at least one compound to decrease polyunsaturated triacylglycerol production in the yeast cell population compared to a corresponding yeast cell population not contacted with the at least one compound. Another aspect of the present disclosure provides a method of producing saturated or monounsaturated triacylglycerols in a yeast cell population, by: (a) providing a yeast cell population; and (b) contacting the yeast cell population with at least one compound, where the at least one compound induces production of one or more saturated or monounsaturated triacylglycerols in the yeast cell population. Another aspect of the present disclosure provides a method of decreasing polyunsaturated triacylglycerol production in a yeast cell population, by: (a) providing a yeast cell population; and (b) contacting the yeast cell population with at least compound, where the at least one compound decreases polyunsaturated triacylglycerol production in the yeast cell population compared to a corresponding yeast cell population not contacted with the at least one compound.

In certain embodiments that may be combined with any of the preceding embodiments, the at least one compound is selected from the compounds listed in Table 1. In certain embodiments that may be combined with any of the preceding embodiments, the at least one compound is selected from a lipoxygenase inhibitor, a kinase inhibitor, a phosphatase inhibitor, a lipase inhibitor, and an oxidative signaling compound. In certain embodiments that may be combined with any of the preceding embodiments, the at least one compound is cycloheximide. In certain embodiments that may be combined with any of the preceding embodiments, the at least one compound is glycerol. In certain embodiments that may be combined with any of the preceding embodiments, the at least one compound is quinacrine. In certain embodiments that may be combined with any of the preceding embodiments, the at least one compound is cAMP. In certain embodiments that may be combined with any of the preceding embodiments, the at least one compound is (−)-epigallocatechin gallate. In certain embodiments that may be combined with any of the preceding embodiments, the at least one compound is forskolin. In certain embodiments that may be combined with any of the preceding embodiments, the at least one compound is PTP Inhibitor II. In certain embodiments that may be combined with any of the preceding embodiments, the at least one oxidative signaling compound is orlistat.

In certain embodiments that may be combined with any of the preceding embodiments, the method further includes producing a biofuel from the produced saturated or monounsaturated triacylglycerols. In certain embodiments that may be combined with any of the preceding embodiments, the method further includes producing a biofuel from lipids produced by the yeast cell population having decreased polyunsaturated triacylglycerol production. In certain embodiments that may be combined with any of the preceding embodiments, the biofuel is a biodiesel.

BRIEF DESCRIPTION OF THE DRAWINGS

FIG. 1B depicts a three-phase process used with microalgae to identify small molecule compounds that target novel pathways involved in fatty acid and triacylglycerol biosynthesis, storage, and metabolism, thereby increasing lipid levels.

FIG. 2A depicts four Venn Diagrams showing the differences in analysis methods when looking at the results of the 54-compound screen. FIG. 2B depicts example of microplate in chemical genetic assay with microalgae.

FIG. 4 depicts a comparison of compound assay results in the four algae strains *P. tricornutum, N. salina, N. oculata,* and *Nannochloris* sp. Compounds were used at a concentration of either 200 nM or 20 μM. *Nannochloris* sp. was grown for 7 days longer than all other algae in order to reach stationary phase.

FIG. 9A depicts cell growth based on absorbance at 680 nm. FIG. 9B depicts cell growth based on increase of chlorophyll fluorescence (530/590 nm). FIG. 9C depicts percent fluorescence relative to the control, which is set to zero. FIG. 9D depicts fluorescence values with standard.

FIG. 12A depicts growth of *N. salina* in 96-well plates tracked by absorbance with varying concentrations of PTP Inhibitor II. Compound wells contain 100 μL media+150 μL algae+PTP inhibitor II diluted in 1 μL of DMSO. Control wells contain 0.4% DMSO. FIG. 12B depicts percent increase for Nile Red lipid measurement is relative to the DMSO control, based on day 20.

FIG. 17A depicts green tea extract. FIG. 17B depicts black tea extract. Values represent an average of four plate replicates. Tea (Tazo brand) was extracted using 20 mL isopropyl alcohol, and then extract was filtered and concentrated. A stock solution was prepared by diluting the extract in DMSO. Compound wells contain 100 μL media+150 μL algae+compound diluted in 1 μL of DMSO. Control wells contain 0.4% DMSO.

FIG. 20A depicts the dose-response effects of (-)-epigallocatechin gallate (EGCG) with *N. salina*. FIG. 20B depicts the dose-response effects of quinacrine with *N. oculata*. FIG. 20C depicts the dose-response effects of BPDQ with *N. salina*. Data points and error bars (s.e.m.) in optical density and Nile Red fluorescence measurements represent a mean of replicates. For FIG. 20A, there were 6 replicates. For FIG. 20B there were 4 replicates. For FIG. 20C, there were 2 replicates for 4.0 μM and 1.5 μM and 3 replicates for all other concentrations. *=P<0.05, **=P<0.01, two-tailed t-test.

FIG. 21A depicts dose-response effects of quinacrine delivered in water with *Nannochloris* sp. FIG. 21B depicts dose-response effects of bisindolylmaleimide delivered in water with *Nannochloris* sp. FIG. 21C depicts dose-response effects of BPDQ in water with *N. salina*. FIG. 21D depicts dose-response effects of gossypol with *N. salina*. Cell density was measured by optical density at 680 nm. Nile red fluorescence (530/590 nm) intensity values represent the difference relative to the control measured. Data points and error bars (s.e.m.) in optical density and Nile Red fluorescence measurements represent the mean of three replicates. * denotes concentrations that are statistically significant (P<0.05, two-tailed t-test).

FIG. 22a depicts a comparison of growth analysis with the addition of cycloheximide in the initial phase (day 0) and at exponential phase (day 6). FIG. 22b depicts a comparison of lipid analysis based on Nile Red fluorescence intensity at harvest (day 16) showing temporal effects for cycloheximide on intracellular lipid levels. FIG. 22c depicts the molecular structure of cycloheximide. FIG. 22d depicts a comparison of growth analysis with the addition of SB202190 in the initial phase (day 0) and at exponential phase (day 6). FIG. 22e depicts lipid analysis based on Nile Red fluorescence intensity were compared at harvest (day 16) showing temporal effects for SB202190 on intracellular lipid levels. FIG. 22f depicts the molecular structure of SB202190. Error bars represent s.e.m. for the difference in absorbance (FIGS. 22a and 22d) and Nile Red fluorescence (FIGS. 22b and 22e) represent the standard deviation of 3 replicates. The error bars in absorbance measurements are not visible because the standard deviation for each data point is approximately 0.01.

DETAILED DESCRIPTION

Overview

Figure 1A:
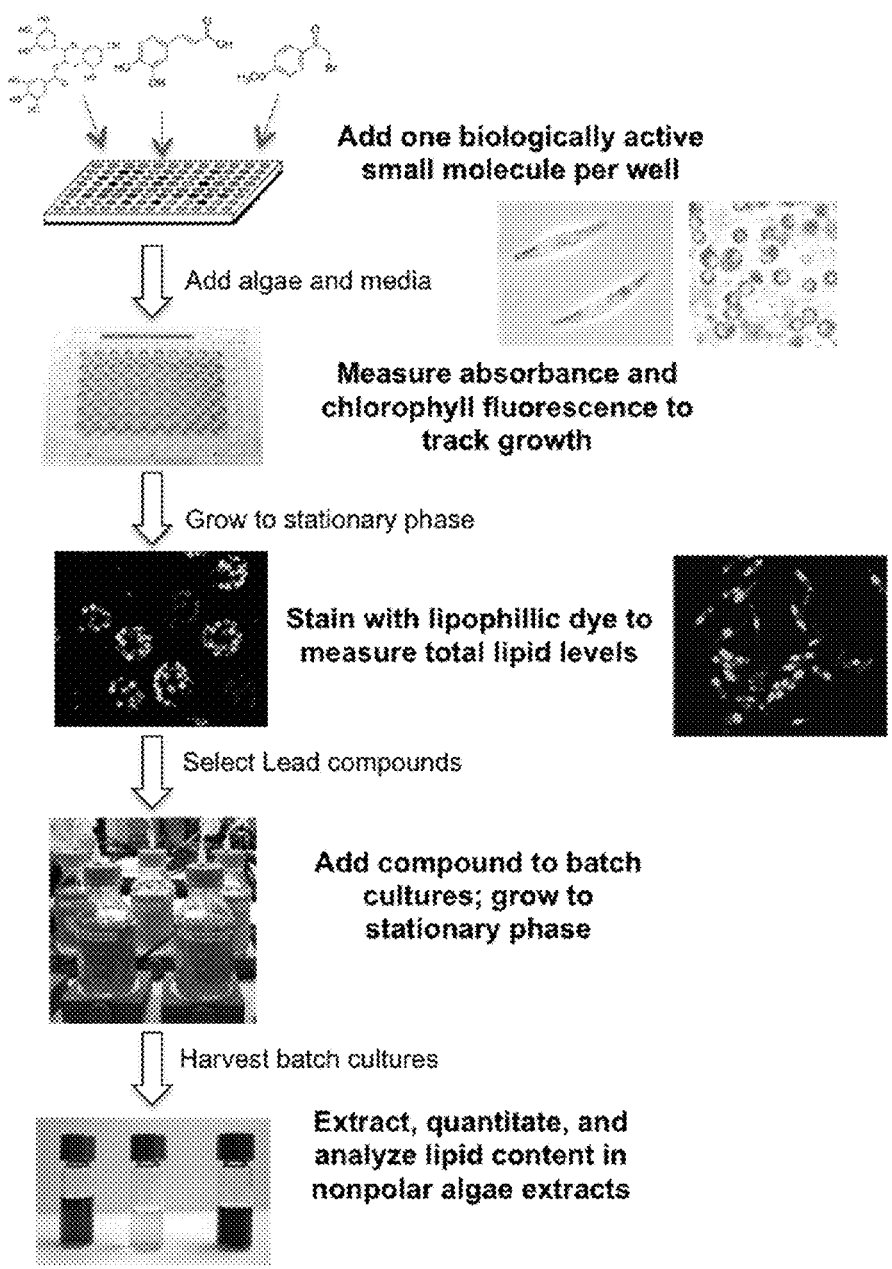
FIG. 1A depicts the overall process to identify small molecules that increase lipid production in algae.

The present disclosure relates to methods of increasing lipid levels, of producing saturated triacylglycerols or monounsaturated triacylglycerols, and of decreasing polyunsaturated triacylglycerol production in algae and yeast cell populations by contacting the cell population with one or more chemical compounds that increase lipid levels and alter lipid composition in the cell population. Moreover, the present disclosure is based, at least in part, on the use of a novel three-phase process to identify small molecule compounds that increase lipid levels, increase growth rate, and alter the lipid composition in algae and yeast.

Accordingly, certain aspects of the present disclosure relate to methods of increasing lipid levels in an algal or yeast cell population, by providing an algal or yeast cell population; and contacting the algal or yeast cell population with at least one lipoxygenase inhibitor, kinase inhibitor, phosphatase inhibitor, kinase inhibitor or activator, lipase inhibitor, or oxidative signaling compound in an amount sufficient for the at least one lipoxygenase inhibitor, kinase inhibitor, phosphatase inhibitor, kinase inhibitor or activator, lipase inhibitor, or oxidative signaling compound to increase lipid levels in the algal or yeast cell population, where the at least one lipoxygenase inhibitor, kinase inhibitor, phosphatase inhibitor, kinase inhibitor or activator, lipase inhibitor, or oxidative signaling compound does not inhibit fatty acid metabolism. Other aspects of the present disclosure relate to methods of increasing lipid levels in an algal or yeast cell population, by providing an algal or yeast cell population; and contacting the algal or yeast cell population with at least one compound from Table 1 in an amount sufficient for the at least one compound to increase lipid levels in the algal or yeast cell population, where the at least one compound does not inhibit fatty acid metabolism. Still other aspects of the present disclosure relate to methods of increasing lipid levels in an algal or yeast cell population, by providing an algal or yeast cell population; and contacting the algal or yeast cell population with at least one compound that increases lipid production in the algal or yeast cell population in amount sufficient for the compound to increase lipid levels in the algal or yeast cell population, where the at least one compound is not derived from a biohydrogen waste stream, and where the at least one compound does not inhibit fatty acid metabolism.

Further aspects of the present disclosure relate to methods of producing saturated triacylglycerols or monounsaturated triacylglycerols in an algal or yeast cell population, by providing an algal or yeast cell population; and contacting the with at least one lipoxygenase inhibitor, kinase inhibitor, phosphatase inhibitor, kinase inhibitor or activator, lipase inhibitor, or oxidative signaling compound in an amount sufficient for the at least one lipoxygenase inhibitor, kinase inhibitor, phosphatase inhibitor, kinase inhibitor or activator, lipase inhibitor, or oxidative signaling compound to induce production of one or more saturated or monounsaturated triacylglycerols in the algal or yeast cell population. Other aspects of the present disclosure relate to methods of producing saturated triacylglycerols or monounsaturated triacylglycerols in an algal or yeast cell population, by providing an algal or yeast cell population; and contacting the algal or yeast cell population with at least one compound from Table 1 in an amount sufficient for the at least one compound to induce production of one or more saturated or monounsaturated triacylglycerols in the algal or yeast cell population. Still other aspects of the present disclosure relate to methods of producing saturated triacylglycerols or monounsaturated triacylglycerols in an algal or yeast cell population, by providing an algal or yeast cell population; and contacting the algal or yeast cell population with at least one compound that induces production of one or more saturated or monounsaturated triacylglycerols in the algal or yeast cell population.

Still further aspects of the present disclosure relate to methods of decreasing polyunsaturated triacylglycerol production in an algal or yeast cell population, by providing an algal or yeast cell population; and contacting the with at least one lipoxygenase inhibitor, kinase inhibitor, phosphatase inhibitor, kinase inhibitor or activator, lipase inhibitor, or oxidative signaling compound in an amount sufficient for the at least one lipoxygenase inhibitor, kinase inhibitor, phosphatase inhibitor, kinase inhibitor or activator, lipase inhibitor, or oxidative signaling compound to decrease polyunsaturated triacylglycerol production in the algal or yeast cell population compared to a corresponding algal or yeast cell population not contacted with the at least one lipoxygenase inhibitor, kinase inhibitor, phosphatase inhibitor, kinase inhibitor or activator, lipase inhibitor, or oxidative signaling compound. Other aspects of the present disclosure relate to methods of decreasing polyunsaturated triacylglycerol production in an algal or yeast cell population, by providing an algal or yeast cell population; and contacting the algal or yeast cell population with at least one compound from Table 1 in an amount sufficient for the at least one compound to decrease polyunsaturated triacylglycerol production in the algal or yeast cell population compared to a corresponding algal or yeast cell population not contacted with the at least one compound. Still other aspects of the present disclosure relate to methods of decreasing polyunsaturated triacylglycerol production in an algal or yeast cell population, by providing an algal or yeast cell population; and contacting the algal or yeast cell population with at least one compound that decreases polyunsaturated triacylglycerol production in the algal or yeast cell population compared to a corresponding algal or yeast cell population not contacted with the at least one compound.

Definitions

As used herein, "lipid" refers to a fat-soluble (lipophilic), naturally-occurring molecule. Lipids include, without limitation, fats, waxes, sterols, fat-soluble vitamins (e.g., vitamins A, D, E, and K), phospholipids, and fatty-acids and their derivatives, such as monoglycerides, diglycerides, and triglycerides. As used herein, the terms "triacylglycerol(s)," "triglyceride(s)," "triacylglyceride(s)," "triglycerol(s)", and TAG(s)" are used interchangeably and refer to any naturally occurring ester of glycerol and three fatty acids that may be of different chain lengths.

As used herein, "lipid levels" refers to the total amount of the various types of lipids, such as triacylglycerols, within an algal cell population.

As used herein, "fatty acid metabolism" refers to the catabolic and anabolic processing of cellular fatty acids, such as the breakdown or degradation of fatty acids within a cell, to generate energy, primary metabolites, and biologically important molecules. Examples of cellular fatty acid metabolism pathways can include gluconeogenesis (i.e., conversion of fatty acids into sugars/carbohydrates), or beta-oxidation (i.e., oxidation of fatty acids to generate acetyl-CoA for energy).

Cell Populations

Algal Cells

Certain aspects of the present disclosure relate to treating an algal cell population with at least one compound, such as a lipoxygenase inhibitor, kinase inhibitor, phosphatase inhibitor, kinase inhibitor or activator, lipase inhibitor, or oxidative signaling compound, to increase lipid levels, produce saturated triacylglycerols or monounsaturated triacylglycerols, or decrease polyunsaturated triacylglycerol production in the algal cell population.

Algal cells, or algae, are photosynthetic organisms of multiple phylogenetic groups, and includes numerous unicellular and multicellular species.

Examples of algae include, without limitation, seaweed, sea grass, marine microflora, microalgae, brown algae, green algae, red algae, golden algae, golden-brown algae, diatoms, and haptophytes.

In certain embodiments, algal cells or algae of the present disclosure are microalgae.

As used herein, algae also include prokaryotic cyanobacteria, such as blue-green algae.

Examples of suitable algae that may be used in the methods of the present disclosure include, without limitation, algae from the phylogenetic groups *Amphipleura, Amphora, Ankistrodesmus, Bacillariophyta, Boekelovia, Botryococcus, Chaetoceros, Chlorella, Chlorococcum, Chlorophyta, Chrysophyta, Cryptophyta, Cyclotella, Cymbella, Dunaliella, Euglenophyta, Eustigmatophyta, Fragilaria, Glaucophyta, Hantzschia, Haptophyta, Isochysis, Monoraphidium, Nannochloropsis, Navicula, Nitzschia, Oocystis, Oscillatoria, Phaeodactylum, Phaeophyta, Pleurochysi, Prasinophyta, Pyrrophyta, Raphidophyta, Rhodophyta, Scenedesmus, Synechococcus, Tetraselmis, Thalassiosira*, and *Xanthophyta*.

In certain preferred aspects, the algal cell population is a population of *Phaeodactylum tricornutum, Nannochloropsis salina, Nannochloropsis oculata*, or *Nannochloris* sp. cells.

Methods of culturing algal cells are well known in the art, and include, without limitation, the methods disclosed herein. For example, algal cells are cultured in a suitable medium (e.g., F/2 medium or Erdschriber's medium). The medium may further contain a suitable carbon source. The algae may be grown under autotrophic, heterotrophic, or mixotrophic conditions and include without limitation, various external organic carbon sources such as glycerol or glucose. Additionally, algae may be grown under either microplate or larger scale batch culture conditions.

Yeast Cells

Other aspects of the present disclosure relate to treating a yeast cell population with at least one compound, such as a lipoxygenase inhibitor, kinase inhibitor, phosphatase inhibitor, kinase inhibitor or activator, lipase inhibitor, or oxidative signaling compound, to increase lipid levels, produce saturated or monounsaturated triacylglycerols, or decrease polyunsaturated triacylglycerol production in the yeast cell population.

As used herein, "yeast" includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

Examples of yeast include, without limitation, industrial yeast strains, laboratory yeast strains, and wild-type yeast strains.

Examples of suitable yeast that may be used in the methods of the present disclosure include, without limitation, yeast from the phylogenetic groups *Brettanomyces, Brettanomyces custersii, Candida, Candida shehatae, Hansenula, Kluyveromyces, Kluyveromyces lactis, Kluyveromyces marxiamus, Pichia, Pichia stipitis, Pichia pastorus, Saccharomyces, Saccharomyces carlsbergensis, Saccharomyces cerevisiae, Saccharomyces diastaticus, Saccharomyces douglasii, Saccharomyces kluyveri, Saccharomyces norbensis, Saccharomyces monacensis, Saccharomyces bayanus, Saccharomyces pastorianus, Saccharomyces pombe, Saccharomyces oviformis, Schizosaccharomyces, Yarrowia, Yarrowia lipolytica, Zygosaccharomyces, Zygosaccharomyces roux*.

Methods of culturing yeast cells are well known in the art. For example, yeast cells may be grown at 35° C. in appropriate media. Suitable growth media include, for example, common commercially prepared media such as Yeast medium (YM) broth. Other defined or synthetic growth media may also be used and the appropriate medium for growth of the particular host cell will be known by someone skilled in the art of microbiology or fermentation science. Temperature ranges and other conditions suitable for growth are known in the art (see, e.g., Bailey and 011 is 1986).

Compounds of the Disclosure

Other aspects of the present disclosure relate to compounds, such as a lipoxygenase inhibitor, kinase inhibitor, phosphatase inhibitor, kinase inhibitors or activators, lipase inhibitor, or oxidative signaling compound that increase lipid levels, produce saturated triacylglycerols or monounsaturated triacylglycerols, or decrease polyunsaturated triacylglycerol production in algal and yeast cell populations.

Compounds of the present disclosure are small molecules that can target and modulate a variety of pathways in algal and yeast cells. The modulation in these pathways results in increased lipid levels, production of saturated triacylglycerols or monounsaturated triacylglycerols, or decreased polyunsaturated triacylglycerol production in the algal and yeast cell. Generally, compounds of the present disclosure target proteins involved in cell signaling processes, such as protein kinases, and also specific proteins involved in metabolism, such as acetyl-CoA carboxylase, lipoxygenases, fatty acid synthase, adenylate cyclase, protein kinase A, and AMP-activated protein kinase. Compounds of the present disclosure can be dissolved in solvents that include, without limitation, nonpolar solvents; polar aprotic solvents, such as dimethyl sulfoxide (DMSO); and polar protic solvents, such as water. The type of solvent used will depend on the type and concentration of compound that is used with a given algal or yeast cell population.

Compounds of the present disclosure that increase lipid levels, produce saturated triacylglycerols or monounsaturated triacylglycerols, or decrease polyunsaturated triacylglycerol production in algal and yeast cells may include, without limitation, kinase inhibitors, kinase activators, phosphatase inhibitors, protein synthesis inhibitors, lipoxygenase inhibitors, lipase inhibitors, monoamine oxidase inhibitors, cyclooxygenase inhibitors, methyltransferase inhibitors, fatty acid synthase inhibitors, oxidative signaling compounds (e.g., antioxidants and NF-kB activators), plant hormones, organic acids, and pharmaceuticals.

Accordingly, suitable compounds of the present disclosure that increase lipid levels, produce saturated triacylglycerols or monounsaturated triacylglycerols, or decrease polyunsaturated triacylglycerol production in algal and yeast cells include, without limitation, the compounds listed in Table 1.

TABLE 1

| Compound | Chemical Name/Structure | Compound Class |
|---|---|---|
| Abscisic acid | (2Z,4E)-5-[(1S)-1-hydroxy-2,6,6-trimethyl-4-oxocyclohex-2-en-1-yl]-3-methylpenta-2,4-dienoic acid | Plant Growth Hormone |
| BPDQ | 4-[(3-bromophenyl)amino]-6,7-diamino-quinazoline | Kinase Inhibitor |
| Arctigenin | (3R,4R)-4-[(3,4-dimethoxyphenyl)methyl]-3-[(4-hydroxy-3-methoxyphenyl)methyl]-2-tetrahydrofuranone | Plant Lignan, Antiviral, Antitumor |
| Baicalein | 5,6,7-Trihydroxy-2-phenyl-chromen-4-one | Lipoxygenase Inhibitor |

TABLE 1-continued

| Compound | Chemical Name/Structure | Compound Class |
| --- | --- | --- |
| CDC25 Phosphatase Inhibiror I | 6-Chloro-7-(2-morpholin-4-yl-ethylamino)-quinoline-5,8-dione | Phosphatase Inhibitor |
| Cerulenin | (2R,3S)-3-[(4E,7E)-Nona-4,7-dienoyl]oxirane-2-carboxamide | Antifungal, Fatty Acid Synthesis Inhibitor |
| Eicosapentaenoic acid | (5Z,8Z,11Z,14Z,17Z)-eicosa-5,8,11,14,17-pentenoic acid | Cyclooxygenase Inhibitor |
| Ethyl 3,4-dephostatin | 4-[(hydroxyamino)-ethylamino]cyclohexa-3,5-diene-1,2-dione | Phosphatase Inhibitor |
| Forskolin | (3R,4aR,5S,6S,6aS,10S,10aR,10bS)-6,10,10b-Trihydroxy-3,4a,7,7,10a-pentamethyl-1-oxo-3-vinyldodecahydro-1H-benzo[f]chromen-5-yl acetate | MAP Kinase inhibitor, stimulates cAMP, Protein Kinase A Activator |
| Genistein | 5,7-Dihydroxy-3-(4-hydroxyphenyl)chromen-4-one | Kinase Inhibitor |
| SB202190 | 4-(4-Flurophenyl)-2-(4-hydroxyphenyl)-5-(4-pyridyl)-1H-imidazole | MAP Kinase Inhibitor |
| pd98059 | 2'-amino-3'-methoxyflavone | Flavone, MAP Kinase Inhibitor |
| N/A | 4-amino-5-(4-chlorophenyl)-7-(t-butyl)pyrazolo[3,4-d]pyrimidine | Tyrosine Kinase inhibitor |
| PTP Inhibitor II | α-Bromo-4-methoxyacetophenone (4-Methoxyphenacyl Br) | Phosphatase Inhibitor |
| Bisindolylmaleimide | 2-[1-(3-Dimethylaminopropyl)-1H-indol-3-yl]-3-(1H-indol-3-yl)-maleimide | Protein kinase C Inhibitor |
| Bohemine | 2-(3-Hydroxypropylamino)-6-benzylamino-9-isopropylpurine | CDK inhibitor |
| Kenpaullone | 9-Bromo-7,12-dihydro-indolo[3,2-][1]benzazepin-6(5H)-one | CDK inhibitor |
| Butein | (E)-1-(2,4-dihydroxyphenyl)-3-(3,4-dihydroxyphenyl)prop-2-en-1-one | Kinase Inhibitor |
| BPIQ-II | 8-[(3-Bromophenyl)amino]-1H-imidazo[4,5-G]-quinazoline | Tyrosine Kinase Inhibitor |
| CDK2 Inhibitor II | 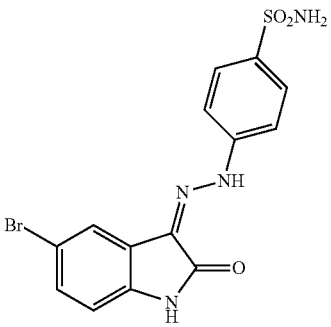 [SMILES: NS(=O)(=O)c1ccc(N/N=C2\C(=O)Nc3ccc(Br)cc32)cc1] | Kinase Inhibitor |
| Aloisine A | 7-n-Butyl-6-(4-hydroxyphenyl)[5H]pyrrolo[2,3-b]pyrazine | Kinase Inhibitor |
| Benzylaminopurine | N-(phenylmethyl)-7H-purin-6-amine | Kinase Inhibitor |
| FAAH Inhibitor I | 4-Benzyloxyphenyl-n-butylcarbamate | Fatty acid hydrolase inhibitor |
| FAAH Inhibitor II | Cyclohexylcarbamic acid-3'-carbamoyl-biphenyl-3-yl Ester, 3'-Carbamoyl-biphenyl-3-yl-cyclohexylcarbamate | Fatty acid hydrolase inhibitor |
| Jasmonic acid | (1R,2R)-3-Oxo-2-(2Z)-2-pentenyl-cyclopentaneacetic acid | Plant hormone |
| Kinetin | $N^6$-furfuryladenine | Plant Hormone |
| Indole acetic acid (IAA) | 2-(1H-indol-3-yl)acetic acid | Plant hormone |
| Resveratrol | 5-[(E)-2-(4-hydroxyphenyl)ethenyl]benzene-1,3-diol | Antioxidant |
| Apigenin | 5,7-Dihydroxy-2-(4-hydroxyphenyl)-4H-1-benzopyran-4-one | Plant Hormone |
| N/A | indole-3-butyric acid | Plant hormone |
| Zeatin | (E)-2-methyl-4-(7H-purin-6-ylamino)but-2-en-1-ol | Cytokinin, plant hormone |
| Epinephrin | (R)-4-(1-hydroxy-2-(methylamino)ethyl)benzene-1,2-diol | Plant Hormone |
| Glycerol | propane-1,2,3-triol | Triacylyglyceride Precursor |
| Ethyl palmitate | Ethyl stearate | Fatty acid |
| Atrazine | 1-Chloro-3-ethylamino-5-isopropylamino-2,4,6-triazine | Herbicide |
| Caffeic acid | 3-(3,4-Dihydroxyphenyl 2-propenoic acid | Lipoxygenase Inhibitor |
| Cantharidin | 2,6-Dimethyl-4,10-dioxatricyclo-[5.2.1.0$^{2,6}$]decane-3,5-dione | Phosphatase Inhibitor |

TABLE 1-continued

| Compound | Chemical Name/Structure | Compound Class |
|---|---|---|
| Citric acid monohydrate | 2-hydroxypropane-1,2,3-tricarboxylic acid | Phosphofructokinase Inhibitor, Glycolysis Regulator |
| Curcumin | (1E,6E)-1,7-bis (4-hydroxy-3-methoxyphenyl)-1,6-heptadiene-3,5-dione | Lipoxygenase Inhibitor |
| D-glucosamine hydrochloride | D-Glucose, 2-amino-2-deoxy-, hydrochloride | Anti-tumor |
| Erbstatin analog | 2,5-Dihydroxymethylcinnamate | Tyrosine Kinase Inhibitor |
| Gibberellic acid | (3S,3aS,4S,4aS,6S,8aR,8bR,11S)-6,11-Dihydroxy-3-methyl-12-methylene-2-oxo-4a,6-ethano-3,8bprop-1-enoperhydroindeno[1,2-b]furan-4-ca | Plant Hormone |
| Ketoconazole | cis-1-Acetyl-4-[4-[[2-(2,4-dichlorophenyl)-2-(1H-imidazol-1-ylmethyl)-1,3-dioxolan-4-yl]methoxy]phenyl]piperazine, R-41400 | Fungicide |
| Naproxen | (S)-(+)-2-(6-Methoxy-2-naphthyl)propionic acid | Cyclooxygenase Inhibitor |
| Cycloheximide | 3-[2-(3,5-Dimethyl-2-oxocyclohexyl)-2-hydroxyethyl]glutarimide | Protein Synthesis Inhibitor |
| Thiamine | Aneurine hydrochloride, Vitamin B1 hydrochloride | Vitamin |
| Acetaminophen | N-(4-hydroxyphenyl)ethanamide | Cyclooxygenase Inhibitor |
| Quercetin | 2-(3,4-dihydroxyphenyl)-3,5,7-trihydroxy-4H-chromen-4-one | MAO Inhibitor |
| Caffeine | 1,3,7-trimethyl-1H-purine-2,6(3H,7H)-dione | Inhibitor of cAMP phosphodiesterase |
| CDK4 Inhibitor I | 2-Bromo-12,13-dihydro-5H-indolo[2,3-a]pyrrolo[3,4-c]carbazole-5,7(6H)-dione | Kinase Inhibitor |
| cAMP | Adenosine 3',5'-cyclophosphate | Kinase Activator |
| Piceatannol | (E)-4-[2-(3,5Dihydroxyphenyl)ethenyl]1,2-benzenediol, 3,3',4,5'-Tetrahydroxy-trans-stilbene | Kinase Inhibitor |
| CDK4 Inhibitor 4 | trans-4-((6-(ethylamino)-2-((1-(phenylmethyl)-1H-indol-5-yl)amino)-4-pyrimidinyl)amino)-cyclohexanol | Kinase Inhibitor |
| Indomethacin | 1-(4-Chlorobenzoyl)-5-methoxy-2-methyl-3-indoleacetic acid | Inhibits prostoglandin synthesis, Cyclooxygenase Inhibitor |
| Quinacrine | 6-Chloro-9-(4-diethylamino-1-methylbutyl-amino)-2-methoxyacridine dihydrochloride | Histamine N-methyl transferase inhibitor, NF-kB activator, p53 activator |
| AICAR (acadesine) | [(2R,3S,4R,5R)-5-(4-Carbamoyl-5-amino-imidazol-1-yl)-3,4-dihydroxyoxolan-2-yl]methyl dihydrogen phosphate | Kinase Activator |
| Orlistat (tetrahydrolipstatin) | (S)-((S)-1-((2S,3S)-3-hexyl-4-oxooxetan-2-yl) tridecan-2-yl) 2-formamido-4-methylpentanoate | Lipase Inhibitor |
| (+)-Catechin | (2R,3S)-2-(3,4-dihydroxyphenyl)-3,4-dihydro-2H-chromene-3,5,7-triol | Antioxidant |
| (−)-Epicatechin gallate | [(2R,3R)-2-(3,4-dihydroxyphenyl)-5,7-dihydroxy-3,4-dihydro-2H-chromen-3-yl] 3,4,5-trihydroxybenzoate | Antioxidant |
| (−)-Epigallocatechin | (2R,3R)-2-(3,4,5-trihydroxyphenyl)-3,4-dihydro-2H-chromene-3,5,7-triol | Antioxidant |
| (−)-Epigallocatechin gallate | [(2R,3R)-5,7-dihydroxy-2-(3,4,5-trihydroxy-phenyl)-3,4-dihydro-2H-chromen-3-yl] 3,4,5-trihydroxybenzoate | Antioxidant |
| Emodin | 1,3,8-trihydroxy-6-methylanthracene-9,10-dione | Kinase Inhibitor |
| Naphthyl acid phosphate | naphthalen-2-yl hydrogen phosphate | Phosphatase Inhibitor |
| Dephostatin | 2-[(hydroxyamino)-methylamino]cyclohexa-2,5-diene-1,4-dione | Phosphatase Inhibitor |
| 3,4-Dephostatin | 4-[(hydroxyamino)-methylamino]cyclohexa-3,5-diene-1,2-dione | Phosphatase Inhibitor |
| Esculetin | 6,7-Dihydroxy-2-chromenone | Lipoxygenase Inhibitor |
| RHC80267 | 1,6-bis(Cyclohexyloximinocarbonylamino)hexane | Lipase Inhibitor |
| JZL 184 hydrate | 4-nitrophenyl-4-[bis(1,3-benzodioxol-5-yl)(hydroxy)methyl]piperidine-1-carboxylate | Lipase Inhibitor |
| Halopemide | N-[2-[4-(5-Chloro-2,3-dihydro-2-oxo-1H-benzimidazol-1-yl)piperidino]ethyl]-4-fluorobenzamide | Lipase Inhibitor |
| Palmityl Trifluoromethyl Ketone (PTFK) | 1,1,1-Trifluoro-2-heptadecanone | Lipase Inhibitor |
| ET-18-OCH$_3$ | 2-Methoxy-3-(octadecyloxy)propyl 2-(trimethylammonio)ethyl phosphate | Lipase Inhibitor |
| BHA | 2-tert-Butyl-4-hydroxyanisole and 3-tert-butyl-4-hydroxyanisole (mixture) | Antioxidant |
| Propyl gallate | propyl 3,4,5-trihydroxybenzoate | Antioxidant |
| CDK4 Inhibitor 3 | 2-Bromo-12,13-dihydro-5H-indolo[2,3a]pyrrolo[3,4-c]carbazole-5,7(6H)-dione | CDK Inhibitor |

TABLE 1-continued

| Compound | Chemical Name/Structure | Compound Class |
|---|---|---|
| CDK4/6 Inhibitor 4 | trans-4-((6-(ethylamino)-2-((1-(phenylmethyl)-1H-indol-5-yl)amino)-4-pyrimidinyl)amino)-cyclohexanol | CDK Inhibitor |
| Apigenin | 5,7-Dihydroxy-2-(4-hydroxyphenyl)-4H-1-benzopyran-4-one | Flavone, PTP Inhibitor, Cytochrome P450, 2C9 inhibitor |
| Quercetin | 2-(3,4-dihydroxyphenyl)-3,5,7-trihydroxy-4H-chromen-4-one | Flavone, Antioxidant, MAO Inhibitor |
| Ascorbic acid | (2R)-2-[(1S)-1,2-dihydroxyethyl]-3,4-dihydroxy-2H-furan-5-one | Antioxidant |
| Melatonin | N-Acetyl-5-methoxytryptamine, 5-Methoxy-N-acetyltryptamine | Hormone |
| N,N'-di-sec-butyl-p-phenylenediamine | 1-N,4-N-di(butan-2-yl)benzene-1,4-diamine | Antioxidant |
| DL-α-Tocopherol (Vitamin E) | (2R)-2,5,7,8-tetramethyl-2-[(4R,8R)-4,8,12-trimethyltridecyl]-3,4-dihydrochromen-6-ol | Antioxidant |
| Gossypol | 2,2'-bis-(Formyl-1,6,7-trihydroxy-5-isopropyl-3-methylnaphthalene) | Lipoxygenase Inhibitor |
| Quinazoline | Benzopyrimidine | PTK Inhibitor |
| Chlorogenic acid | (1S,3R,4R,5R)-3-{[(2Z)-3-(3,4-dihydroxyphenyl)prop-2-enoyl]oxy}-1,4,5-trihydroxycyclohexanecarboxylic acid | Phenol, Oxidative Signaling Compound |
| Luteolin | 2-(3,4-Dihydroxyphenyl)-5,7-dihydroxy-4-chromenone | Flavone, Phosphodiesterase (PDE) Inhibitor, Antioxidant |
| NOX Inhibitor III | 7-(1,3-Benzoxazol-2-ylsulfanyl)-3-benzyl-3H-[1,2,3]triazolo[4,5-d]pyrimidine, 1,3-Benzoxazol-2-yl-3-benzyl-3H-[1,2,3]triazolo[4,5-d]pyrimidin-7-yl sulfide | Oxidative Signaling Compound |
| Sulfasalazine | 2-hydroxy-5-[(E)-2-{4-[(pyridin-2-yl)sulfamoyl]phenyl}diazen-1-yl]benzoic acid | Oxidative Signaling Compound |
| 2-amino-1,2,4-triazole | 1,2,4-triazol-4-amine | Oxidative Signaling Compound |
| Apocynin | 1-(4-Hydroxy-3-methoxyphenyl)ethanone | Oxidative Signaling Compound, NADPH Oxidase Inhibitor |
| Cytochrome P450 1B1 inhibitor | (E)-2,3',4,5'-Tetramethoxystilbene | Antioxidant, Cytochrome Inhibitor |
| DL-α-Lipoic Acid | 6,8-dimercaptooctanoic acid | Oxidative Signaling Compound |
| Formononetin | 7-hydroxy-3-(4-methoxyphenyl)chromen-4-one | Oxidative Signaling Compound |
| Glutathione Monoethyl Ester | (2S)-2-amino-5-[[(2R)-1-(carboxymethylamino)-3-ethylsulfanyl-1-oxopropan-2-yl]amino]-5-oxopentanoic acid | Oxidative Signaling Compound |
| LY 231617 | 2,6-bis(1,1-Dimethylethyl)-4-[[(1-ethyl)amino]methyl]phenol | Oxidative Signaling Compound |
| MCI-186 | 3-Methyl-1-phenyl-2-pyrazolin-5-one | Oxidative Signaling Compound |
| N-tert-Butyl-α-phenylnitrone (PBN) | N-(benzylidene)-tert-butylamine | Oxidative Signaling Compound |
| U-74389G | 21-(4-(2,6-di-1-Pyrrolidinyl-4-pyrimidinyl)-1-piperazinyl)-pregna-1,4,9(11)-triene-3,20-dione (Z)-2-butenedioate | Oxidative Signaling Compound |
| Pristimerin | methyl10-hydroxy-2,4a,6a,6a,9,14a-hexamethyl-11-oxo-1,3,4,5,6,13,14,14b-octahydropicene-2-carboxylate | Lipase Inhibitor |
| disulfiram | 1,1',1'',1'''-[disulfanediylbis(carbonothioylnitrilo)]tetraethane | Lipase Inhibitor |
| octhilinone | 2-octyl-1,2-thiazol-3(2H)-one | Lipase Inhibitor |
| N/A | (2-butoxyphenyl)boronic acid | Lipase Inhibitor |
| DMSO | dimethylsulfoxide | Antioxidant, Oxidative Signaling Compound |
| Rapamycin | (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone | Antibiotic |

Lipoxygenase Inhibitors

In some aspects of the present disclosure, compounds that increase lipid levels, produce saturated triacylglycerols or monounsaturated triacylglycerols, or decrease polyunsaturated triacylglycerol production in algal and yeast cells are lipoxygenase inhibitors.

As used herein, lipoxygenase inhibitors are a class of compounds that slows the action of a lipoxygenase enzyme. Lipoxygenases are iron-containing enzymes that catalyze the dioxygenation of polyunsaturated fatty acids. In one non-limiting example, the lipoxygenase arachidonate 5-lipoxygenase converts essential fatty acids, such as linoleic acid, into leukotrienes. Leukotrienes are important signaling molecules. Without wishing to be bound by theory, it is believed that inhibiting the synthesis of leukotrienes will alter signaling pathways and result in an increase of fatty acid triglycerides in algae and yeast.

Accordingly, lipoxygenase inhibitors suitable for use in the methods of the present disclosure include, without limitation, the compounds listed in Table 2.

TABLE 2

| Compound | Chemical Name/Structure | Compound Class |
|---|---|---|
| Curcumin | (1E,6E)-1,7-bis (4-hydroxy-3-methoxyphenyl)-1,6-heptadiene-3,5-dione | Lipoxygenase Inhibitor |
| Caffeic acid | 3-(3,4-Dihydroxyphenyl 2-propenoic acid | Lipoxygenase Inhibitor |
| Baicalein | 5,6,7-Trihydroxy-2-phenyl-chromen-4-one | Lipoxygenase Inhibitor |
| Esculetin | 6,7-Dihydroxy-2-chromenone | Lipoxygenase Inhibitor |
| Gossypol | 2,2'-bis-(Formyl-1,6,7-trihydroxy-5-isopropyl-3-methylnaphthalene) | Lipoxygenase Inhibitor |

Kinase Inhibitors

In some aspects of the present disclosure, compounds that increase lipid levels, produce saturated triacylglycerols or monounsaturated triacylglycerols, or decrease polyunsaturated triacylglycerol production in algal and yeast cells are kinase inhibitors, including but not limited to protein tyrosine kinase (PTK) inhibitors.

As used herein, kinase inhibitors are a class of compounds that slows the action of kinases. Kinases are molecular switches for cellular functions and regulate cell division. Constitutively active kinase mutations can lead to unregulated cell growth, which may result in tumorigenesis. Thus, kinase inhibitors are commonly used in cancer treatment.

Accordingly, kinase inhibitors suitable for use in the methods of the present disclosure include, without limitation, the compounds listed in Table 3.

TABLE 3

| Compound | Chemical Name/Structure | Compound Class |
|---|---|---|
| BPDQ | 4-[(3-Bromophenyl)amino]-6,7-diaminoquinazoline | Kinase Inhibitor |
| Genistein | 5,7-Dihydroxy-3-(4-hydroxyphenyl)chromen-4-one | Kinase Inhibitor |
| Butein | (E)-1-(2,4-dihydroxyphenyl)-3-(3,4-dihydroxyphenyl)prop-2-en-1-one | Kinase Inhibitor |
| Emodin | 1,3,8-trihydroxy-6-methylanthracene-9,10-dione | Kinase Inhibitor |
| Piceatannol | 5-[(E)-2-(3,'-dihydroxyphenyl)vinyl]-benzene-1,3-diol | Kinase Inhibitor |
| Quinazoline | Benzopyrimidine | Kinase Inhibitor |
| BPIQ-II | 8-[(3-Bromophenyl)amino]-1H-imidazo[4,5-G]-quinazoline | Kinase Inhibitor |

Phosphatase Inhibitors

In some aspects of the present disclosure, compounds that increase lipid levels, produce saturated triacylglycerols or monounsaturated triacylglycerols, or decrease polyunsaturated triacylglycerol production in algal and yeast cells are phosphatase inhibitors, including but not limited to protein tyrosine phosphatase (PTP) inhibitors.

As used herein, phosphatase inhibitors are a class of compounds that slows the action of phosphatases. Phosphatases generally regulate cellular growth and differentiation, and can be key components for MAP (mitogen activate protein) kinase pathways. MAP kinases are enzymes that regulate cell activities in response to environmental stimuli. The MAP kinase cascade involves protein tyrosine kinases, protein kinase C, and G-protein coupled receptors.

Accordingly, phosphatase inhibitors suitable for use in the methods of the present disclosure include, without limitation, the compounds listed in Table 4.

TABLE 4

| Compound | Chemical Name/Structure | Compound Class |
|---|---|---|
| PTP Inhibitor II | α-Bromo-4-methoxyacetophenone | Phosphatase Inhibitor |
| Ethyl 3,4-dephostatin | 4-[hydroxyamino)-ethylamino]cyclohexa-3,5-diene-1,2-dione | Phosphatase Inhibitor |
| Cantharidin | 2,6-Dimethyl-4,10-dioxatricyclo-[5.2.1.0$^{2,6}$]decane-3,5-dione | Phosphatase Inhibitor |
| Napthyl acid phosphate | naphthalen-2-yl hydrogen phosphate | Phosphatase Inhibitor |
| Dephostatin | 2-[(hydroxyamino)-methylamino]-cyclohexa-2,5-diene-1,4-dione | Phosphatase Inhibitor |
| 3,4-dephostatin | 4-[(hydroxyamino)-methylamino]-cyclohexa-3,5-diene-1,2-dione | Phosphatase Inhibitor |

Kinase Inhibitors and Activators

In some aspects of the present disclosure, compounds that increase lipid levels, produce saturated triacylglycerols or monounsaturated triacylglycerols, or decrease polyunsaturated triacylglycerol production in algal and yeast cells are kinase inhibitors or activators.

As used herein, kinases are enzymes that add a phosphate group to control the activity of specific target proteins. Kinases regulate a variety of cellular processes, including those involved with signal transduction. Kinases that are involved in growth and lipid production include, without limitation, cyclic-dependent kinases, protein kinase A, mitogen-activated protein (MAP) kinases, and protein tyrosine kinases.

Cyclin-dependent kinases are involved in signaling for the regulation of the cell cycle.

As used herein, protein kinase A (PKA) kinases are enzymes that have activity dependent on cyclic adenosine mono-phosphate (cAMP), and thus are also known as cAMP-dependent protein kinases. PKAs are involved in the regulation of lipid metabolism.

As used herein, MAP (mitogen activated protein) kinases are enzymes that regulate cell activities in response to environmental stimuli. The MAP kinase cascade can involve protein tyrosine kinases, protein kinase C, and G-protein coupled receptors. Protein tyrosine phosphatases generally regulate cellular growth and differentiation, and can be key components for MAP kinase pathways.

Accordingly, kinase inhibitors or activators suitable for use in the methods of the present disclosure include, without limitation, the compounds listed in Table 5.

TABLE 5

| Compound | Chemical Name/Structure | Compound Class |
|---|---|---|
| BPDQ | 4-[(3-bromophenyl)amino]-6,7-diamino-quinazoline | Kinase Inhibitor |
| Forskolin | (3R,4aR,5S,6S,6aS,10S,10aR,10bS)-6,10,10b-Trihydroxy-3,4a,7,7,10a-pentamethyl-1-oxo-3-vinyldodecahydro-1H-benzo[f]chromen-5-yl acetate | MAP Kinase inhibitor, stimulates cAMP, Protein Kinase A Activator |
| Genistein | 5,7-Dihydroxy-3-(4-hydroxyphenyl)chromen-4-one | Kinase Inhibitor |
| SB202190 | 4-(4-Fluorophenyl)-2-(4-hydroxyphenyl)-5-(4-pyridyl)-1H-imidazole | MAP Kinase Inhibitor |
| pd98059 | 2'-amino-3'-methoxyflavone | Flavone, MAP Kinase Inhibitor |
| N/A | 4-amino-5-(4-chlorophenyl)-7-(t-butyl)pyrazolo[3,4-d]pyrimidine | Tyrosine Kinase inhibitor |
| Bisindolylmaleimide | 2-[1-(3-Dimethylaminopropyl)-1H-indol-3-yl]-3-(1H-indol-3-yl)-maleimide | Protein kinase C Inhibitor |
| Bohemine | 2-(3-Hydroxypropylamino)-6-benzylamino-9-isoproylpurine | CDK inhibitor |
| Kenpaullone | 9-Bromo-7,12-dihydro-indolo[3,2-d][1]benzazepin-6(5H)-one | CDK inhibitor |
| Butein | (E)-1-(2,4-dihydroxyphenyl)-3-(3,4-dihydroxyphenyl)prop-2-en-1-one | Kinase Inhibitor |
| BPIQ-II | 8-[(3-Bromophenyl)amino]-1H-imidazo[4,5-]-quinazoline | Tyrosine Kinase Inhibitor |
| CDK2 Inhibitor II | [structure] | Kinase Inhibitor |
| Aloisine A | 7-n-Butyl-6-(4-hydroxyphenyl)[5H]pyrrolo[2,3-b]pyrazine | Kinase Inhibitor |
| CDK4 Inhibitor I | 2-Bromo-12,13-dihydro-5H-indolo[2,3-a]pyrrolo[3,4-c]carbazole-5,7(6H)-dione | Kinase Inhibitor |
| cAMP | Adenosine 3',5'-cyclophosphate | Kinase Activator |
| Piceatannol | (E)-4-[2-(3,5Dihydroxyphenyl)ethenyl]1,2-benzenediol, 3,3',4,5'-Tetrahydroxy-trans-stilbene | Kinase Inhibitor |
| CDK4 Inhibitor 4 | trans-4-((6-(ethylamino)-2-((1-(phenylmethyl)-1H-indol-5-yl)amino)-4-pyrimidinyl)amino)-cyclohexanol | Kinase Inhibitor |
| AICAR (acadesine) | [(2R,3S,4R,5R)-5-(4-Carbamoyl-5-amino-imidazol-1-yl)-3,4-dihydroxyoxolan-2-yl]methyl dihydrogen phosphate | Kinase Activator |
| CDK4 Inhibitor 3 | 2-Bromo-12,13-dihydro-5H-indolo[2,3a]pyrrolo[3,4-c]carbazole-5,7(6H)-dione | CDK Inhibitor |
| CDK4/6 Inhibitor 4 | trans-4-((6-(ethylamino)-2-((1-(phenylmethyl)-1H-indol-5-yl)amino)-4-pyrimidinyl)amino)-cyclohexanol | CDK Inhibitor |

Lipase Inhibitors

In some aspects of the present disclosure, compounds that increase lipid levels, produce saturated triacylglycerols or monounsaturated triacylglycerols, or decrease polyunsaturated triacylglycerol production in algal and yeast cells are lipase inhibitors.

As used herein, lipase inhibitors are a class of compounds that slows the action of a lipase enzyme. Lipases enzymes catalyze the cleavage, or breakdown, of lipids.

Accordingly, lipase inhibitors suitable for use in the methods of the present disclosure include, without limitation, the compounds listed in Table 6.

TABLE 6

| Compound | Chemical Name/Structure | Compound Class |
|---|---|---|
| RHC80267 | 1,6-bis(Cyclohexyloximino-carbonylamino)hexane | Lipase Inhibitor |
| Orlistat (tetrahydrolipstatin) | (S)-((S)-1-((2S,3S)-3-hexyl-4-oxooxetan-2-yl)tridecan-2-yl) 2-formamido-4-methylpentanoate | Lipase Inhibitor |
| JZL 184 hydrate | 4-nitrophenyl-4-[bis(1,3-benzodioxol-5-yl)(hydroxy)methyl]piperidine-1-carboxylate | Lipase Inhibitor |

TABLE 6-continued

| Compound | Chemical Name/Structure | Compound Class |
|---|---|---|
| Halopemide | N-[2-[4-(5-Chloro-2,3-dihydro-2-oxo-1H-benzimidazol-1-yl)-piperidino]ethyl]-4-fluorobenzamide | Lipase Inhibitor |
| PTFK | 1,1,1-Trifluoro-2-heptadecanone | Lipase Inhibitor |
| ET-18-OCH$_3$ (Edelfosine) | 2-Methoxy-3-(octadecyloxy)-propyl 2-(trimethyl ammonio) ethyl phosphate | Lipase Inhibitor |
| Pristimerin | methyl10-hydroxy-2,4a,6a,6a,9,14a-hexamethyl-11-oxo-1,3,4,5,6,13,14,14b-octahydropicene-2-carboxylate | Lipase Inhibitor |
| disulfiram | 1,1',1'',1'''-[disulfanediylbis(carbonothioylnitrilo)]tetraethane | Lipase Inhibitor |
| octhilinone | 2-octyl-1,2-thiazol-3(2H)-one | Lipase Inhibitor |
| N/A | (2-butoxyphenyl)boronic acid | Lipase Inhibitor |

Oxidative Signaling Compounds

In some aspects of the present disclosure, compounds that increase lipid levels, produce saturated triacylglycerols or monounsaturated triacylglycerols, or decrease polyunsaturated triacylglycerol production in algal and yeast cells are oxidative signaling compounds. As used herein, an "oxidative signaling compound" is a compound involved in signaling pathways that regulate oxidation and reduction (i.e., antioxidant network) and thus regulate gene expression, such as pathways that are responsive to oxidative stress or damage due to sunlight, photosynthesis, environmental damage (Foyer and Shigeoka, *Plant Physiology* 155, 93-100, 2011). These pathways regulate carbon-nitrogen metabolism (Hu et al., *The Plant Journal* 54, 621-639, 2008; and Tones et al., *Ecotoxicology and Environmental Safety,* 2008) and therefore are connected to lipid-production pathways. Cells have a natural antioxidant network with molecules that are electron acceptors in the cell wall that act together with antioxidant genes such as ascorbate oxidase to regulate metabolism and growth, a cycle crucial to cell expansion. Oxidative signaling compounds may include, without limitation, antioxidants, adneylate cyclase inhibitors/activators, glutathione S-transferase inhibitors, free radical scavengers, NF-kB inhibitors, cytochrome inhibitors, NADPH oxidase inhibitors, protein kinase activators, and protein kinase inhibitors.

As used herein, antioxidants are a class of compounds that inhibit the oxidation of molecules. Oxidation is a chemical reaction that transfers electrons or hydrogen from a substance to an oxidizing agent. Oxidation reactions can produce free radicals, which can start chain reactions. When the chain reaction occurs in a cell, it can cause damage or death to the cell. Antioxidants are capable of terminating such chain reactions by removing free radical intermediates, and by inhibiting further oxidation reactions.

Accordingly, oxidative signaling compounds suitable for use in the methods of the present disclosure include, without limitation, the compounds listed in Table 7.

TABLE 7

| Compound | Chemical Name/Structure | Compound Class |
|---|---|---|
| Resveratrol | 5-[(E)-2-(4-hydroxyphenyl)ethenyl]benzene-1,3-diol | Antioxidant |
| (+)-Catechin | (2R,3S)-2-(3,4-dihydroxyphenyl)-3,4-dihydro-2H-chromene-3,5,7-triol | Antioxidant |
| (−)-Epicatechin gallate | [(2R,3R)-2-(3,4-dihydroxyphenyl)-5,7-dihydroxy-3,4-dihydro-2H-chromen-3-yl] 3,4,5-trihydroxybenzoate | Antioxidant |
| (−)-Epigallocatechin | (2R,3R)-2-(3,4,5-trihydroxyphenyl)-3,4-dihydro-2H-chromene-3,5,7-triol | Antioxidant |
| (−)-Epigallocatechin gallate | [(2R,3R)-5,7-dihydroxy-2-(3,4,5-trihydroxy phenyl)-3,4-dihydro-2H-chromen-3-yl] 3,4,5-trihydroxybenzoate | Antioxidant |
| BHA | 2-tert-Butyl-4-hydroxyanisole and 3-tert-butyl-4-hydroxyanisole (mixture) | Antioxidant |
| Propyl gallate | Propyl-3,4,5-trihydroxybenzoate | Antioxidant |
| Ascorbic acid | (2R)-2-[(1S)-1,2-dihydroxyethyl]-3,4-dihydroxy-2H-furan-5-one | Antioxidant |
| N,N'-di-sec-butyl-p-phenylenediamine | 1-N,4-N-di(butan-2-yl)benzene-1,4-diamine | Antioxidant |
| α-D-Tocopherol (Vitamin E) | (2R)-2,5,7,8-tetramethyl-2-[(4R,8R)-4,8,12-trimethyltridecyl]-3,4-dihydrochromen-6-ol | Antioxidant |
| Quinacrine | 6-Chloro-9-(4-diethylamino-1-methylbutyl-amino)-2-methoxyacridine dihydrochloride | Histamine N-methyl transferase inhibitor, NF-kB activator, p53 activator |
| Chlorogenic acid | (1S,3R,4R,5R)-3-{[(2Z)-3-(3,4-dihydroxyphenyl)prop-2-enoyl]oxy}-1,4,5-trihydroxycyclohexanecarboxylic acid | Phenol, Oxidative Signaling Compound |
| Luteolin | 2-(3,4-Dihydroxyphenyl)-5,7-dihydroxy-4-chromenone | Flavone, Phosphodiesterase (PDE) Inhibitor, Antioxidant |
| NOX Inhibitor III | 7-(1,3-Benzoxazol-2-ylsulfanyl)-3-benzyl-3H-[1,2,3]triazolo[4,5-d]pyrimidine, 1,3-Benzoxazol-2-yl-3-benzyl-3H-[1,2,3]triazolo[4,5-d]pyrimidin-7-yl sulfide | Oxidative Signaling Compound |
| Sulfasalazine | 2-hydroxy-5-[(E)-2-{4-[(pyridin-2-yl)sulfamoyl]phenyl}diazen-1-yl]benzoic acid | Oxidative Signaling Compound |
| 2-amino-1,2,4-triazole | 1,2,4-triazol-4-amine | Oxidative Signaling Compound |

TABLE 7-continued

| Compound | Chemical Name/Structure | Compound Class |
|---|---|---|
| Apocynin | 1-(4-Hydroxy-3-methoxyphenyl)ethanone | Oxidative Signaling Compound, NADPH Oxidase Inhibitor |
| Cytochrome P450 1B1 inhibitor | (E)-2,3',4,5'-Tetramethoxystilbene | Antioxidant, Cytochrome Inhibitor |
| DL-α-Lipoic Acid | 6,8-dimercaptooctanoic acid | Oxidative Signaling Compound |
| Formononetin | 7-hydroxy-3-(4-methoxyphenyl)chromen-4-one | Oxidative Signaling Compound |
| Glutathione Monoethyl Ester | (2S)-2-amino-5-[[(2R)-1-(carboxymethylamino)-3-ethylsulfanyl-1-oxopropan-2-yl]amino]-5-oxopentanoic acid | Oxidative Signaling Compound |
| LY 231617 | 2,6-bis(1,1-Dimethylethyl)-4-[[(1-ethyl)amino]methyl]phenol | Oxidative Signaling Compound |
| MCI-186 | 3-Methyl-1-phenyl-2-pyrazolin-5-one | Oxidative Signaling Compound |
| N-tert-Butyl-α-phenylnitrone (PBN) | N-(benzylidene)-tert-butylamine | Oxidative Signaling Compound |
| U-74389G | 21-(4-(2,6-di-1-Pyrrolidinyl-4-pyrimidinyl)-1-piperazinyl)-pregna-1,4,9(11)-triene-3,20-dione (Z)-2-butenedioate | Oxidative Signaling Compound |
| Quercetin | 2-(3,4-dihydroxyphenyl)-3,5,7-trihydroxy-4H-chromen-4-one | MAO Inhibitor |

In other aspects, oxidative signaling compounds of the present disclosure also include biomass extracts that contain compounds such as antioxidants. Such extracts include, without limitation, plant extracts, fruit extracts, grape pomace (e.g., seeds, skins and/or stems), olive pomace, tea extract (e.g., green tea extract, black tea extract, white tea extract, and oolong tea extract].

Methods of Increasing Lipid levels

Other aspects of the present disclosure relate to increasing lipid levels in an algal and yeast cell population by treating the algal and yeast cell population with at least one, at least two, at least three, or more compounds, such as such as a lipoxygenase inhibitor, kinase inhibitor, phosphatase inhibitor, kinase inhibitor or activator, lipase inhibitor, or oxidative signaling compound, in an amount sufficient for the compound to increase lipid levels in the cell population. As disclosed herein, compounds of the present disclosure may increase lipid levels in a population of algal and yeast cells by increasing the growth rate of the population, which increases the number of cells in the population thereby increasing the total level of lipids in the population. Additionally, compounds of the present disclosure may increase lipid levels in a population of algal and yeast cells by increasing cellular lipid production in each cell of the population.

The amount of the at least one, at least two, at least three, or more compounds that are sufficient to increase lipid levels in an algal or yeast cell population may vary with the specific compounds used, the strain of algae or yeast used, and the culturing conditions. Methods of determining the optimal amount for a given compound for a given algal or yeast strain and culturing conditions are well known in the art and include, without limitation, the methods disclosed herein. In certain aspects, the algal or yeast cell population is treated with the at least one, at least two, at least three, or more compounds during the lag growth phase of the algal or yeast cell population. In other aspects, the algal or yeast cell population is treated with the at least one, at least two, at least three, or more compounds during the exponential growth phase of the algal or yeast cell population. In other aspects, the algal or yeast cell population is treated with the at least one, at least two, at least three, or more compounds during the stationary growth phase of the algal or yeast cell population.

In some aspects, the at least one, at least two, at least three, or more compounds are compounds that increase lipid levels in algae or yeast, such as those listed in Table 1. In other aspects, the at least one, at least two, at least three, or more compounds are lipoxygenase inhibitors, such as those listed in Table 2. In still other aspects, the at least one, at least two, at least three, or more compounds are kinase inhibitors, such as those listed in Table 3. In yet other aspects, the at least one, at least two, at least three, or more compounds are phosphatase inhibitors, such as those listed in Table 4. In other aspects, the at least one, at least two, at least three, or more compounds are protein kinase inhibitor or activators, such as those listed in Table 5. In still other aspects, the at least one, at least two, at least three, or more compounds are lipase inhibitors, such as those listed in Table 6. In further aspects, the at least one, at least two, at least three, or more compounds are oxidative signaling compounds, such as those listed in Table 7.

The concentration of the at least one, at least two, at least three, or more compounds used to increase lipid levels in algae or yeast may range from about 0.0200 nM to about 100 µM, 0.0200 nM to about 80 µM, 0.0200 nM to about 60 µM, 0.0200 nM to about 40 µM, from about 0.0200 nM to about 20 µM, from about 0.0200 nM to about 15 µM, from about 0.0200 nM to about 10 µM, from about 0.0200 nM to about 5 µM, from about 0.0200 nM to about 1 µM, from about 0.0200 nM to about 800 nM, from about 0.0200 nM to about 600 nM, from about 0.0200 nM to about 400 nM, from about 0.0200 nM to about 200 nM, from about 0.0200 nM to about 100 nM, from about 0.0200 nM to about 50 nM, from about 0.0200 nM to about 40 nM, from about 0.0200 nM to about 30 nM, from about 0.0200 nM to about 20 nM, from about 0.0200 nM to about 10 nM, from about 0.0200 nM to about 5 nM, from about 0.0200 nM to about 4 nM, from about 0.0200 nM to about 2 nM, from about 0.0200 nM to about 1 nM, from about 0.0200 nM to about 0.800 nM, from about 0.0200 nM to about 0.600 nM, from about 0.0200 nM to about 0.400 nM, from about 0.0200 nM to about 0.200 nM, from about 0.0200 nM to about 0.100 nM, from about 0.0200 nM to about 0.0900 nM, from about 0.0200 nM to about 0.0800 nM, from about 0.0200 nM to about 0.0700 nM, from about 0.0200 nM to about 0.0600 nM, from about 0.0200 nM to about 0.0500 nM, from about 0.0200 nM to about 0.0400 nM, or from about 0.0200 nM to about 0.0300 nM.

In certain aspects, the concentration of the at least one, at least two, at least three, or more compounds used to increase lipid levels in algae or yeast is at least about 0.0200 nM, at least about 0.0210 nM, at least about 0.0220 nM, at least about 0.0230 nM, at least about 0.0240 nM, at least about 0.0250 nM, at least about 0260 nM, at least about 0.0270 nM, at least about 0.0280 nM, at least about 0.0290 nM, at least about 0.0300 nM, at least about 0.0350 nM, at least about 0.0400 nM, at least about 0.0450 nM, at least about 0.0500 nM, at least about 0.0550 nM, at least about 0.0600 nM, at least about 0.0650 nM, at least about 0.0700 nM, at least about 0.0750 nM, at least about 0.0800 nM, at least about 0.0850 nM, at least about 0.0900 nM, at least about 0.0950 nM, at least about 0.1000 nM, at least about 0.200 nM, at least about 0.225 nM, at least about 0.300 nM, at least about 0.400 nM, at least about 0.500 nM, at least about 0.600 nM, at least about 0.650 nM, at least about 0.660 nM, at least about 0.670 nM, at least about 0.680 nM, at least about 0.690 nM, at least about 0.700 nM, at least about 0.750 nM, at least about 0.800 nM, at least about 0.850 nM, at least about 0.900 nM, at least about 0.950 nM, at least about 1 nM, at least about 1.5 nM, at least about 2 nM, at least about 2.5 nM, at least about 3 nM, at least about 3.5 nM, at least about 4 nM, at least about 4.5 nM, at least about 5 nM, at least about 5.5 nM, at least about 6 nM, at least about 6.5 nM, at least about 7 nM, at least about 7.5 nM, at least about 8 nM, at least about 8.5 nM, at least about 9 nM, at least about 9.5 nM, at least about 10 nM, at least about 10.5 nM, at least about 11 nM, at least about 11.5 nM, at least about 12 nM, at least about 12.5 nM, at least about 13 nM, at least about 13.5 nM, at least about 14 nM, at least about 14.5 nM, at least about 15 nM, at least about 15.5 nM, at least about 16 nM, at least about 16.5 nM, at least about 17 nM, at least about 17.5 nM, at least about 18 nM, at least about 18.5 nM, at least about 19 nM, at least about 19.5 nM, at least about 20 nM, at least about 21 nM, at least about 22 nM, at least about 23 nM, at least about 24 nM, at least about 25 nM, at least about 26 nM, at least about 27 nM, at least about 28 nM, at least about 29 nM, at least about 30 nM, at least about 31 nM, at least about 32 nM, at least about 33 nM, at least about 34 nM, at least about 35 nM, at least about 36 nM, at least about 37 nM, at least about 38 nM, at least about 39 nM, at least about 40 nM, at least about 41 nM, at least about 42 nM, at least about 43 nM, at least about 44 nM, at least about 45 nM, at least about 46 nM, at least about 47 nM, at least about 48 nM, at least about 49 nM, at least about 50 nM, at least about 51 nM, at least about 52 nM, at least about 53 nM, at least about 54 nM, at least about 55 nM, at least about 56 nM, at least about 57 nM, at least about 58 nM, at least about 59 nM, at least about 60 nM, at least about 61 nM, at least about 62 nM, at least about 63 nM, at least about 64 nM, at least about 65 nM, at least about 66 nM, at least about 67 nM, at least about 68 nM, at least about 69 nM, at least about 70 nM, at least about 71 nM, at least about 72 nM, at least about 73 nM, at least about 74 nM, at least about 75 nM, at least about 76 nM, at least about 77 nM, at least about 78 nM, at least about 79 nM, at least about 80 nM, at least about 81 nM, at least about 82 nM, at least about 83 nM, at least about 84 nM, at least about 85 nM, at least about 86 nM, at least about 87 nM, at least about 88 nM, at least about 89 nM, at least about 90 nM, at least about 91 nM, at least about 92 nM, at least about 93 nM, at least about 94 nM, at least about 95 nM, at least about 96 nM, at least about 97 nM, at least about 98 nM, at least about 99 nM, at least about 100 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 185 nM, at least about 190 nM, at least about 195 nM, at least about 200 nM, at least about 225 nM, at least about 250 nM, at least about 275 nM, at least about 300 nM, at least about 325 nM, at least about 350 nM, at least about 375 nM, at least about 400 nM, at least about 425 nM, at least about 450 nM, at least about 475 nM, at least about 500 nM, at least about 525 nM, at least about 550 nM, at least about 575 nM, at least about 600 nM, at least about 625 nM, at least about 650 nM, at least about 655 nM, at least about 660 nM, at least about 665 nM, at least about 670 nM, at least about 675 nM, at least about 680 nM, at least about 685 nM, at least about 690 nM, at least about 695 nM, at least about 700 nM, at least about 725 nM, at least about 750 nM, at least about 775 nM, at least about 800 nM, at least about 825 nM, at least about 850 nM, at least about 875 nM, at least about 900 nM, at least about 925 nM, at least about 950 nM, at least about 975 nM, at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 5.5 µM, at least about 6 µM, at least about 6.5 µM, at least about 7 µM, at least about 7.5 µM, at least about 8 µM, at least about 8.5 µM, at least about 9 µM, at least about 9.5 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 21 µM, at least about 22 µM, at least about 23 µM, at least about 24 µM, at least about 25 µM, at least about 26 µM, at least about 27 µM, at least about 28 µM, at least about 29 µM, at least about 30 µM, at least about 31 µM, at least about 32 µM, at least about 33 µM, at least about 34 µM, at least about 35 µM, at least about 36 µM, at least about 37 µM, at least about 38 µM, at least about 39 µM, at least about 40 µM, at least about 41 µM, at least about 42 µM, at least about 43 µM, at least about 44 µM, at least about 45 µM, at least about 50 µM, at least about 55 µM, at least about 60 µM, at least about 65 µM, at least about 70 µM, at least about 75 µM, at least about 80 µM, at least about 85 µM, at least about 90 µM, at least about 95 µM, or at least about 100 µM.

In further aspects, the at least one, at least two, at least three, or more compounds used to increase lipid levels in algae or yeast, increase lipid levels in an algal and yeast cell population by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 205%, at least 210%, at least 215%, at least 220%, at least 225%, at least 230%, at least 235%, at least 240%, at least 245%, at least 250%, at least 255%, at least 260%, at least 265%, at least 270%, at least 275%, at least 280%, at least 285%, at least 290%, at least 295%, at least 300%, at least 305%, at least 310%, at least 315%, at least 320%, at least 325%, at least 330%, at least 335%, at least 340%, at least 345%, at least 350%, at least 355%, at least 360%, at least 365%, at least 370%, at least 375%, at least 380%, at least 385%, at least 390%, at least 395%, at least 400%, at least 405%, at least 410%, at least 415%, at least 420%, at least 425%, at least 430%, at least 435%, at least 440%, at least 445%, at least 450%, at least 455%, at least 460%, at least 465%, at least 470%, at least 475%, at least 480%, at least 485%, at least 490%, at least 495%, at least 500%, at least 550%, at least 600%, at least 650%, at least 700%, at least 750%, at least 800%, at least 850%, at least 900%, at least 950%, at least 1,000% or more compared to a corresponding algal or yeast cell population not contacted with the at least one, at least two, at least three, or more compounds used to increase lipid levels in algae or yeast.

In other aspects, the at least one, at least two, at least three, or more compounds used to increase lipid levels in algae or yeast, increase levels of triacylglycerols in an algal or yeast cell population. Preferably, the at least one, at least two, at least three, or more compounds increase levels of saturated fatty acid levels or monounsaturated fatty acid levels in the algal or yeast cell population. In certain aspects, the saturated triacylglycerols have carbon chain-lengths of at least 8 carbons, at least 10 carbons, carbons, at least 12 carbons, at least 14 carbons, at least 16 carbons, at least 18 carbons, at least 20 carbons, at least 22 carbons, at least 24 carbons, at least 26 carbons, at least 28 carbons at least 30 carbons, or more. In other aspects, the monounsaturated triacylglycerols have carbon chain-lengths of at least 8 carbons, at least 10 carbons, carbons, at least 12 carbons, at least 14 carbons, at least 16 carbons, at least 18 carbons, at least 20 carbons, at least 22 carbons, at least 24 carbons, at least 26 carbons, at least 28 carbons at least 30 carbons, or more. Such long carbon chain-length saturated triacylglycerols monounsaturated triacylglycerols are useful in the production of biofuels, such as biodiesel.

Methods of Modulating Cell Growth

Other aspects of the present disclosure relate to altering the growth rate of an algal or yeast cell population by treating the algal or yeast cell population with at least one, at least two, at least three, or more compounds, such as such as a lipoxygenase inhibitor, kinase inhibitor, phosphatase inhibitor, kinase inhibitor or activator, lipase inhibitor, or oxidative signaling compound, in an amount sufficient for the compound to alter the growth rate in the cell population. Certain compounds may increase the growth rate, while others may decrease the growth rate of the algal or yeast cell population or not have an effect on growth rate.

In certain aspects, the least one, at least two, at least three, or more compounds alter the growth rate of the algal or yeast cell population without increasing lipid levels in the cell population. In other aspects, the least one, at least two, at least three, or more compounds alter the growth rate in addition to increasing the lipid levels in the cell population.

In some aspects, the at least one, at least two, at least three, or more compounds used to alter algal or yeast growth rate are compounds that increase lipid levels in algae or yeast, such as those listed in Table 1. In other aspects, the at least one, at least two, at least three, or more compounds used to alter algal or yeast growth rate are lipoxygenase inhibitors, such as those listed in Table 2. In still other aspects, the at least one, at least two, at least three, or more compounds used to alter algal or yeast growth rate are kinase inhibitors, such as those listed in Table 3. In yet other aspects, the at least one, at least two, at least three, or more compounds used to alter algal or yeast growth rate are phosphatase inhibitors, such as those listed in Table 4. In other aspects, the at least one, at least two, at least three, or more compounds used to alter algal or yeast growth rate are protein kinase inhibitors or activators, such as those listed in Table 5. In other aspects, the at least one, at least two, at least three, or more compounds used to alter algal or yeast growth rate are lipase inhibitors, such as those listed in Table 6. In further aspects, the at least one, at least two, at least three, or more compounds used to alter algal or yeast growth rate are oxidative signaling compounds, such as those listed in Table 7.

In further aspects, treating an algal or yeast cell population with at least one, at least two, at least three, or more compounds, such as such as a lipoxygenase inhibitor, kinase inhibitor, phosphatase inhibitor, kinase inhibitor or activator, lipase inhibitor, or oxidative signaling compound increases algal or yeast cell growth rate. In some aspects, the at least one, at least two, at least three, or more compounds are selected from the compounds listed in Table 8. In some embodiments, treating an algal or yeast cell population with at least one, at least two, at least three, or more compounds of the present disclosure increases algal or yeast cell growth rate when the algal or yeast cells are grown under nitrogen-deficient conditions. Methods of growing algal and yeast cells under nitrogen-deficient conditions are well known in the art and include, without limitation, those disclosed herein. In one non-limiting example, growing algal or yeast cells under nitrogen-deficient conditions includes growing the cells in culture medium containing at least 75%, at least 70%, at least 65%, at least 60%, at least 55%, at least 50%, at least 45%, at least 40%, at least 35%, at least 34%, at least 33%, at least 32%, at least 31%, at least 30%, at least 29%, at least 28%, at least 27%, at least 26%, at least 25%, at least 24%, at least 23%, at least 22%, at least 21%, at least 20%, at least 19%, at least 18%, at least 17%, at least 16%, at least 15%, at least 14%, at least 13%, at least 12%, at least 11%, at least 10%, at least 9%, at least 8%, at least 7%, at least 6%, at least 5%, at least 4%, at least 3%, at least 2%, at least 1%, or less nitrogen as compared to the amount that is present in nitrogen-containing culture medium.

TABLE 8

| Compound | Chemical Name/Structure | Compound Class |
| --- | --- | --- |
| (−)-Epigallocatechin gallate | [(2R,3R)-5,7-dihydroxy-2-(3,4,5-trihydroxy phenyl)-3,4-dihydro-2H-chromen-3-yl] 3,4,5-trihydroxybenzoate | Antioxidant |
| Propyl gallate | Propyl-3,4,5-trihydroxybenzoate | Antioxidant |
| BHA | 2-tert-Butyl-4-hydroxyanisole and 3-tert-butyl-4-hydroxyanisole (mixture) | Antioxidant |

TABLE 8-continued

| Compound | Chemical Name/Structure | Compound Class |
| --- | --- | --- |
| DMSO | dimethylsulfoxide | Antioxidant |
| cAMP | Adenosine 3',5'-cyclophosphate | Kinase Activator |
| Forskolin | (3R,4aR,5S,6S,6aS,10S,10aR,10bS)-6,10,10b-Trihydroxy-3,4a,7,7,10a-pentamethyl-1-oxo-3-vinyldodecahydro-1H-benzo[f]chromen-5-yl acetate | Kinase Activator |
| Ethyl 3,4-dephostatin | 4-[(hydroxyamino)-ethylamino]cyclohexa-3,5-diene-1,2-dione | PTP Inhibitor |
| Naphthyl acid phosphate | naphthalen-2-yl hydrogen phosphate | PTP Inhibitor |
| Dephostatin | 2-[(hydroxyamino)-methylamino]cyclohexa-2,5-diene-1,4-dione | PTP Inhibitor |
| 3,4-dephostatin | 4-[(hydroxyamino)-methylamino]cyclohexa-3,5-diene-1,2-dione | PTP Inhibitor |
| PTP Inhibitor II | α-Bromo-4-methoxyacetophenone | PTP Inhibitor |
| SB202190 | 4-(4-Fluorophenyl)-2-(4-hydroxyphenyl)-5-(4-pyridyl)-1H-imidazole | Kinase Inhibitor |
| Benzylaminopurine | N-(phenylmethyl)-7H-purin-6-amine | Kinase Inhibitor |
| Quinacrine | 6-Chloro-9-(4-diethylamino-1-methylbutyl-amino)-2-methxoyacridine dihydrochloride | Histamine N-methyl transferase inhibitor, NF-kB activator, p53 activator |
| Arctigenin | (3R,4R)-4-[(3,4-dimethoxyphenyl)methyl]-3-[(4-hydroxy-3-methoxyphenyl)methyl]-2-tetrahydrofuranone | Plant Lignan, Antiviral, Antitumor |
| Atrazine | 1-Chloro-3-ethylamino-5-isopropylamino-2,4,6-triazine | Herbicide |
| Orlistat (tetrahydrolipstatin) | (S)-((S)-1-((2S,3S)-3-hexyl-4-oxooxetan-2-yl)tridecan-2-yl) 2-formamido-4-methylpentanoate | Lipase Inhibitor |
| Cycloheximide | 3-[2-(3,5-Dimethyl-2-oxocyclohexyl)-2-hydroxyethyl]glutarimide | Protein Synthesis Inhibitor |
| CDK2 Inhibitor II | (structure shown) | Kinase Inhibitor |
| Zeatin | (E)-2-methyl-4-(7H-purin-6-ylamino)but-2-en-1-ol | Cytokinin, plant hormone |
| AICAR (Acadesine) | [(2R,3S,4R,5R)-5-(4-Carbamoyl-5-amino-imidazol-1-yl)-3,4-dihydroxyoxolan-2-yl]methyl dihydrogen phosphate | Kinase Activator |

The amount of the at least one, at least two, at least three, or more compounds that are sufficient to alter the growth rate in an algal or yeast cell population may vary with the specific compounds used, the strain of algae or yeast used, and the culturing conditions. Methods of determining the optimal amount for a given compound for a given algal or yeast strain and culturing conditions are well known in the art and include, without limitation, the methods disclosed herein. In certain aspects, the algal or yeast cell population is treated with the at least one, at least two, at least three, or more compounds during the lag growth phase of the algal or yeast cell population. In other aspects, the algal or yeast cell population is treated with the at least one, at least two, at least three, or more compounds during the exponential growth phase of the algal or yeast cell population.

The concentration of the at least one, at least two, at least three, or more compounds used to alter the growth rate in algae or yeast may range from about 0.0200 nM to about 100 μM, 0.0200 nM to about 80 μM, 0.0200 nM to about 60 μM, 0.0200 nM to about 40 μM, from about 0.0200 nM to about 20 μM, from about 0.0200 nM to about 15 μM, from about 0.0200 nM to about 10 μM, from about 0.0200 nM to about 5 μM, from about 0.0200 nM to about 1 μM, from about 0.0200 nM to about 800 nM, from about 0.0200 nM to about 600 nM, from about 0.0200 nM to about 400 nM, from about 0.0200 nM to about 200 nM, from about 0.0200 nM to about 100 nM, from about 0.0200 nM to about 50 nM, from about 0.0200 nM to about 40 nM, from about 0.0200 nM to about 30 nM, from about 0.0200 nM to about 20 nM, from about 0.0200 nM to about 10 nM, from about 0.0200 nM to about 5 nM, from about 0.0200 nM to about 4 nM, from about 0.0200 nM to about 2 nM, from about 0.0200 nM to about 1 nM, from about 0.0200 nM to about 0.800 nM, from about 0.0200 nM to about 0.600 nM, from about 0.0200 nM to about 0.400 nM, from about 0.0200 nM to about 0.200 nM, from about 0.0200 nM to about 0.100 nM, from about 0.0200 nM to about 0.0900 nM, from about 0.0200 nM to about 0.0800 nM, from about 0.0200 nM to about 0.0700 nM, from about 0.0200 nM to about 0.0600 nM, from about 0.0200 nM to about 0.0500 nM, from about 0.0200 nM to about 0.0400 nM, or from about 0.0200 nM to about 0.0300 nM.

In certain aspects, the concentration of the at least one, at least two, at least three, or more compounds used to alter the growth rate in algae or yeast is at least about 0.0200 nM, at least about 0.0210 nM, at least about 0.0220 nM, at least about 0.0230 nM, at least about 0.0240 nM, at least about 0.0250 nM, at least about 0260 nM, at least about 0.0270 nM, at least about 0.0280 nM, at least about 0.0290 nM, at least about 0.0300 nM, at least about 0.0350 nM, at least about 0.0400 nM, at least about 0.0450 nM, at least about 0.0500 nM, at least about 0.0550 nM, at least about 0.0600 nM, at least about 0.0650 nM, at least about 0.0700 nM, at least about 0.0750 nM, at least about 0.0800 nM, at least about 0.0850 nM, at least about 0.0900 nM, at least about 0.0950 nM, at least about 0.1000 nM, at least about 0.200 nM, at least about 0.225 nM, at least about 0.300 nM, at least about 0.400 nM, at least about 0.500 nM, at least about 0.600 nM, at least about 0.650 nM, at least about 0.660 nM, at least about 0.670 nM, at least about 0.680 nM, at least about 0.690 nM, at least about 0.700 nM, at least about 0.750 nM, at least about 0.800 nM, at least about 0.850 nM, at least about 0.900 nM, at least about 0.950 nM, at least about 1 nM, at least about 1.5 nM, at least about 2 nM, at least about 2.5 nM, at least about 3 nM, at least about 3.5 nM, at least about 4 nM, at least about 4.5 nM, at least about 5 nM, at least about 5.5 nM, at least about 6 nM, at least about 6.5 nM, at least about 7 nM, at least about 7.5 nM, at least about 8 nM, at least about 8.5 nM, at least about 9 nM, at least about 9.5 nM, at least about 10 nM, at least about 10.5 nM, at least about 11 nM, at least about 11.5 nM, at least about 12 nM, at least about 12.5 nM, at least about 13 nM, at least about 13.5 nM, at least about 14 nM, at least about 14.5 nM, at least about 15 nM, at least about 15.5 nM, at least about 16 nM, at least about 16.5 nM, at least about 17 nM, at least about 17.5 nM, at least about 18 nM, at least about 18.5 nM, at least about 19 nM, at least about 19.5 nM, at least about 20 nM, at least about 21 nM, at least about 22 nM, at least about 23 nM, at least about 24 nM, at least about 25 nM, at least about 26 nM, at least about 27 nM, at least about 28 nM, at least about 29 nM, at least about 30 nM, at least about 31 nM, at least about 32 nM, at least about 33 nM, at least about 34 nM, at least about 35 nM, at least about 36 nM, at least about 37 nM, at least about 38 nM, at least about 39 nM, at least about 40 nM, at least about 41 nM, at least about 42 nM, at least about 43 nM, at least about 44 nM, at least about 45 nM, at least about 46 nM, at least about 47 nM, at least about 48 nM, at least about 49 nM, at least about 50 nM, at least about 51 nM, at least about 52 nM, at least about 53 nM, at least about 54 nM, at least about 55 nM, at least about 56 nM, at least about 57 nM, at least about 58 nM, at least about 59 nM, at least about 60 nM, at least about 61 nM, at least about 62 nM, at least about 63 nM, at least about 64 nM, at least about 65 nM, at least about 66 nM, at least about 67 nM, at least about 68 nM, at least about 69 nM, at least about 70 nM, at least about 71 nM, at least about 72 nM, at least about 73 nM, at least about 74 nM, at least about 75 nM, at least about 76 nM, at least about 77 nM, at least about 78 nM, at least about 79 nM, at least about 80 nM, at least about 81 nM, at least about 82 nM, at least about 83 nM, at least about 84 nM, at least about 85 nM, at least about 86 nM, at least about 87 nM, at least about 88 nM, at least about 89 nM, at least about 90 nM, at least about 91 nM, at least about 92 nM, at least about 93 nM, at least about 94 nM, at least about 95 nM, at least about 96 nM, at least about 97 nM, at least about 98 nM, at least about 99 nM, at least about 100 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 185 nM, at least about 190 nM, at least about 195 nM, at least about 200 nM, at least about 225 nM, at least about 250 nM, at least about 275 nM, at least about 300 nM, at least about 325 nM, at least about 350 nM, at least about 375 nM, at least about 400 nM, at least about 425 nM, at least about 450 nM, at least about 475 nM, at least about 500 nM, at least about 525 nM, at least about 550 nM, at least about 575 nM, at least about 600 nM, at least about 625 nM, at least about 650 nM, at least about 655 nM, at least about 660 nM, at least about 665 nM, at least about 670 nM, at least about 675 nM, at least about 680 nM, at least about 685 nM, at least about 690 nM, at least about 695 nM, at least about 700 nM, at least about 725 nM, at least about 750 nM, at least about 775 nM, at least about 800 nM, at least about 825 nM, at least about 850 nM, at least about 875 nM, at least about 900 nM, at least about 925 nM, at least about 950 nM, at least about 975 nM, at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 5.5 µM, at least about 6 µM, at least about 6.5 µM, at least about 7 µM, at least about 7.5 µM, at least about 8 µM, at least about 8.5 µM, at least about 9 µM, at least about 9.5 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 21 µM, at least about 22 µM, at least about 23 µM, at least about 24 µM, at least about 25 µM, at least about 26 µM, at least about 27 µM, at least about 28 µM, at least about 29 µM, at least about 30 µM, at least about 31 µM, at least about 32 µM, at least about 33 µM, at least about 34 µM, at least about 35 µM, at least about 36 µM, at least about 37 µM, at least about 38 µM, at least about 39 µM, at least about 40 µM, at least about 41 µM, at least about 42 µM, at least about 43 µM, at least about 44 µM, at least about 45 µM, at least about 50 µM, at least about 55 µM, at least about 60 µM, at least about 65 µM, at least about 70 µM, at least about 75 µM, at least about 80 µM, at least about 85 µM, at least about 90 µM, at least about 95 µM, or at least about 100 µM.

Methods of Producing Saturated and Monounsaturated Triacylglycerols

Other aspects of the present disclosure relate to producing saturated triacylglycerols or monounsaturated triacylglycerols in an algal or yeast cell population by treating the algal or yeast cell population with at least one, at least two, at least three, or more compounds, such as such as a lipoxygenase inhibitor, kinase inhibitor, phosphatase inhibitor, kinase inhibitor or activator, lipase inhibitor, or oxidative signaling compound, in an amount sufficient for the compound to induce production of one or more saturated or monounsaturated triacylglycerols in said algal or yeast cell population. As used herein, "saturated triacylglycerols" refers to triacylglycerols that do not contain double bonds between the individual carbon atoms of the fatty acid carbon chain. As used herein, "monounsaturated triacylglycerols" refers to triacylglycerols that contain a single double bond within the fatty acid carbon chain.

The amount of the at least one, at least two, at least three, or more compounds that are sufficient to induce production of one or more saturated or monounsaturated triacylglycerols in an algal or yeast cell population may vary with the specific compounds used, the strain of algae or yeast used, and the culturing conditions. Methods of determining the optimal amount for a given compound for a given algal or yeast strain and culturing conditions are well known in the art and include, without limitation, the methods disclosed herein. In certain aspects, the algal or yeast cell population is treated with the at least one, at least two, at least three, or more compounds during the lag growth phase of the algal or yeast cell population. In other aspects, the algal or yeast cell population is treated with the at least one, at least two, at least three, or more compounds during the exponential growth phase of the algal or yeast cell population.

In some aspects, the at least one, at least two, at least three, or more compounds used to induce production of one or more saturated or monounsaturated triacylglycerols are compounds that increase lipid levels in algae or yeast, such as those listed in Table 1. In other aspects, the at least one, at least two, at least three, or more compounds used to induce production of one or more saturated or monounsaturated triacylglycerols are lipoxygenase inhibitors, such as those listed in Table 2. In still other aspects, the at least one, at least two, at least three, or more compounds used to induce production of one or more saturated or monounsaturated triacylglycerols are kinase inhibitors, such as those listed in Table 3. In yet other aspects, the at least one, at least two, at least three, or more compounds used to induce production of one or more saturated or monounsaturated triacylglycerols are phosphatase inhibitors, such as those listed in Table 4. In other aspects, the at least one, at least two, at least three, or more compounds used to induce production of one or more saturated or monounsaturated triacylglycerols are protein kinase inhibitors or activators, such as those listed in Table 5. In other aspects, the at least one, at least two, at least three, or more compounds used to induce production of one or more saturated or monounsaturated triacylglycerols are lipase inhibitors, such as those listed in Table 6. In further aspects, the at least one, at least two, at least three, or more compounds used to induce production of one or more saturated or monounsaturated triacylglycerols are oxidative signaling compounds, such as those listed in Table 7.

The concentration of the at least one, at least two, at least three, or more compounds used to induce production of one or more saturated or monounsaturated triacylglycerols in algae or yeast may range from about 0.0200 nM to about 100 µM, 0.0200 nM to about 80 µM, 0.0200 nM to about 60 µM, 0.0200 nM to about 40 µM, from about 0.0200 nM to about 20 µM, from about 0.0200 nM to about 15 µM, from about 0.0200 nM to about 10 µM, from about 0.0200 nM to about 5 µM, from about 0.0200 nM to about 1 µM, from about 0.0200 nM to about 800 nM, from about 0.0200 nM to about 600 nM, from about 0.0200 nM to about 400 nM, from about 0.0200 nM to about 200 nM, from about 0.0200 nM to about 100 nM, from about 0.0200 nM to about 50 nM, from about 0.0200 nM to about 40 nM, from about 0.0200 nM to about 30 nM, from about 0.0200 nM to about 20 nM, from about 0.0200 nM to about 10 nM, from about 0.0200 nM to about 5 nM, from about 0.0200 nM to about 4 nM, from about 0.0200 nM to about 2 nM, from about 0.0200 nM to about 1 nM, from about 0.0200 nM to about 0.800 nM, from about 0.0200 nM to about 0.600 nM, from about 0.0200 nM to about 0.400 nM, from about 0.0200 nM to about 0.200 nM, from about 0.0200 nM to about 0.100 nM, from about 0.0200 nM to about 0.0900 nM, from about 0.0200 nM to about 0.0800 nM, from about 0.0200 nM to about 0.0700 nM, from about 0.0200 nM to about 0.0600 nM, from about 0.0200 nM to about 0.0500 nM, from about 0.0200 nM to about 0.0400 nM, or from about 0.0200 nM to about 0.0300 nM.

In certain aspects, the concentration of the at least one, at least two, at least three, or more compounds used to induce production of one or more saturated or monounsaturated triacylglycerols in algae or yeast is at least about 0.0200 nM, at least about 0.0210 nM, at least about 0.0220 nM, at least about 0.0230 nM, at least about 0.0240 nM, at least about 0.0250 nM, at least about 0260 nM, at least about 0.0270 nM, at least about 0.0280 nM, at least about 0.0290 nM, at least about 0.0300 nM, at least about 0.0350 nM, at least about 0.0400 nM, at least about 0.0450 nM, at least about 0.0500 nM, at least about 0.0550 nM, at least about 0.0600 nM, at least about 0.0650 nM, at least about 0.0700 nM, at least about 0.0750 nM, at least about 0.0800 nM, at least about 0.0850 nM, at least about 0.0900 nM, at least about 0.0950 nM, at least about 0.1000 nM, at least about 0.200 nM, at least about 0.225 nM, at least about 0.300 nM, at least about 0.400 nM, at least about 0.500 nM, at least about 0.600 nM, at least about 0.650 nM, at least about 0.660 nM, at least about 0.670 nM, at least about 0.680 nM, at least about 0.690 nM, at least about 0.700 nM, at least about 0.750 nM, at least about 0.800 nM, at least about 0.850 nM, at least about 0.900 nM, at least about 0.950 nM, at least about 1 nM, at least about 1.5 nM, at least about 2 nM, at least about 2.5 nM, at least about 3 nM, at least about 3.5 nM, at least about 4 nM, at least about 4.5 nM, at least about 5 nM, at least about 5.5 nM, at least about 6 nM, at least about 6.5 nM, at least about 7 nM, at least about 7.5 nM, at least about 8 nM, at least about 8.5 nM, at least about 9 nM, at least about 9.5 nM, at least about 10 nM, at least about 10.5 nM, at least about 11 nM, at least about 11.5 nM, at least about 12 nM, at least about 12.5 nM, at least about 13 nM, at least about 13.5 nM, at least about 14 nM, at least 14.5 nM, at least about 15 nM, at least about 15.5 nM, at least about 16 nM, at least about 16.5 nM, at least about 17 nM, at least about 17.5 nM, at least about 18 nM, at least about 18.5 nM, at least about 19 nM, at least about 19.5 nM, at least about 20 nM, at least about 21 nM, at least about 22 nM, at least about 23 nM, at least about 24 nM, at least about 25 nM, at least about 26 nM, at least about 27 nM, at least about 28 nM, at least about 29 nM, at least about 30 nM, at least about 31 nM, at least about 32 nM, at least about 33 nM, at least about 34 nM, at least about 35 nM, at least about 36 nM, at least about 37 nM, at least about 38 nM, at least about 39 nM, at least about 40 nM, at least about 41 nM, at least about 42 nM, at least about 43 nM, at least about 44 nM, at least about 45 nM, at least about 46 nM, at least about 47 nM, at least about 48 nM, at least about 49 nM, at least about 50 nM, at least about 51 nM, at least about 52 nM, at least about 53 nM, at least about 54 nM, at least about 55 nM, at least about 56 nM, at least about 57 nM, at least about 58 nM, at least about 59 nM, at least about 60 nM, at least about 61 nM, at least about 62 nM, at least about 63 nM, at least about 64 nM, at least about 65 nM, at least about 66 nM, at least about 67 nM, at least about 68 nM, at least about 69 nM, at least about 70 nM, at least about 71 nM, at least about 72 nM, at least about 73 nM, at least about 74 nM, at least about 75 nM, at least about 76 nM, at least about 77 nM, at least about 78 nM, at least about 79 nM, at least about 80 nM, at least about 81 nM, at least about 82 nM, at least about 83 nM, at least about 84 nM, at least about 85 nM, at least about 86 nM, at least about 87 nM, at least about 88 nM, at least about 89 nM, at least about 90 nM, at least about 91 nM, at least about 92 nM, at least about 93 nM, at least about 94 nM, at least about 95 nM, at least about 96 nM, at least about 97 nM, at least about 98 nM, at least about 99 nM, at least about 100 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 185 nM, at least about 190 nM, at least about 195 nM, at least about 200 nM, at least about 225 nM, at least about 250 nM, at least about 275 nM, at least about 300 nM, at least about 325 nM, at least about 350 nM, at least about 375 nM, at least about 400 nM, at least about 425 nM, at least about 450 nM, at least about 475 nM, at least about 500 nM, at least about 525 nM, at least about 550 nM, at least about 575 nM, at least about 600 nM, at least about 625 nM, at least about 650 nM, at least about 655 nM, at least about 660 nM, at least about 665 nM, at least about 670 nM, at least about 675 nM, at least about 680 nM, at least about 685 nM, at least about 690 nM, at least about 695 nM, at least about 700 nM, at least about 725 nM, at least about 750 nM, at least about 775 nM, at least about 800 nM, at least about 825 nM, at least about 850 nM, at least about 875 nM, at least about 900 nM, at least about 925 nM, at least about 950 nM, at least about 975 nM, at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 5.5 µM, at least about 6 µM, at least about 6.5 µM, at least about 7 µM, at least about 7.5 µM, at least about 8 µM, at least about 8.5 µM, at least about 9 µM, at least about 9.5 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 21 µM, at least about 22 µM, at least about 23 µM, at least about 24 µM, at least about 25 µM, at least about 26 µM, at least about 27 µM, at least about 28 µM, at least about 29 µM, at least about 30 µM, at least about 31 µM, at least about 32 µM, at least about 33 µM, at least about 34 µM, at least about 35 µM, at least about 36 µM, at least about 37 µM, at least about 38 µM, at least about 39 µM, at least about 40 µM, at least about 41 µM, at least about 42 µM, at least about 43 µM, at least about 44 µM, at least about 45 µM, at least about 50 µM, at least about 55 µM, at least about 60 µM, at least about 65 µM, at least about 70 µM, at least about 75 µM, at least about 80 µM, at least about 85 µM, at least about 90 µM, at least about 95 µM, or at least about 100 µM.

Methods of Decreasing Polyunsaturated Triacylglycerol Production

Other aspects of the present disclosure relate to decreasing polyunsaturated triacylglycerol production in an algal or yeast cell population by treating the algal or yeast cell population with at least one, at least two, at least three, or more compounds, such as such as lipoxygenase inhibitors, kinase inhibitors, phosphatase inhibitors, kinase inhibitors or activators, lipase inhibitors, or oxidative signaling compounds, in an amount sufficient for the compound to decreasing polyunsaturated triacylglycerol production in said algal or yeast cell population compared to a corresponding algal or yeast cell population not treated with the compound. As used herein, a "polyunsaturated triacylglycerol" refers to a triacylglycerol that includes two or more double bonds within the fatty acid carbon chain.

The amount of the at least one, at least two, at least three, or more compounds that are sufficient to decrease polyunsaturated triacylglycerol production in said algal or yeast cell population may vary with the specific compounds used, the strain of algae or yeast used, and the culturing conditions. Methods of determining the optimal amount for a given compound for a given algal or yeast strain and culturing conditions are well known in the art and include, without limitation, the methods disclosed herein. In certain aspects, the algal or yeast cell population is treated with the at least one, at least two, at least three, or more compounds during the lag growth phase of the algal or yeast cell population. In other aspects, the algal or yeast cell population is treated with the at least one, at least two, at least three, or more compounds during the exponential growth phase of the algal or yeast cell population.

In some aspects, the at least one, at least two, at least three, or more compounds used to decrease polyunsaturated triacylglycerol production are compounds that increase lipid levels in algae or yeast, such as those listed in Table 1. In other aspects, the at least one, at least two, at least three, or more compounds used to decrease polyunsaturated triacylglycerol production are lipoxygenase inhibitors, such as those listed in Table 2. In still other aspects, the at least one, at least two, at least three, or more compounds used to decrease polyunsaturated triacylglycerol production are kinase inhibitors, such as those listed in Table 3. In yet other aspects, the at least one, at least two, at least three, or more compounds used to decrease polyunsaturated triacylglycerol production are phosphatase inhibitors, such as those listed in Table 4. In other aspects, the at least one, at least two, at least three, or more compounds used to decrease polyunsaturated triacylglycerol production are protein kinase inhibitors or activators, such as those listed in Table 5. In other aspects, the at least one, at least two, at least three, or more compounds used to decrease polyunsaturated triacylglycerol production are lipase inhibitors, such as those listed in Table 6. In further aspects, the at least one, at least two, at least three, or more compounds used to decrease polyunsaturated triacylglycerol production are oxidative signaling compounds, such as those listed in Table 7.

The concentration of the at least one, at least two, at least three, or more compounds used to decrease polyunsaturated triacylglycerol production in algae or yeast may range from about 0.0200 nM to about 100 µM, 0.0200 nM to about 80 µM, 0.0200 nM to about 60 µM, 0.0200 nM to about 40 µM, from about 0.0200 nM to about 20 µM, from about 0.0200 nM to about 15 µM, from about 0.0200 nM to about 10 µM, from about 0.0200 nM to about 5 µM, from about 0.0200 nM to about 1 µM, from about 0.0200 nM to about 800 nM, from about 0.0200 nM to about 600 nM, from about 0.0200 nM to about 400 nM, from about 0.0200 nM to about 200 nM, from about 0.0200 nM to about 100 nM, from about 0.0200 nM to about 50 nM, from about 0.0200 nM to about 40 nM, from about 0.0200 nM to about 30 nM, from about 0.0200 nM to about 20 nM, from about 0.0200 nM to about 10 nM, from about 0.0200 nM to about 5 nM, from about 0.0200 nM to about 4 nM, from about 0.0200 nM to about 2 nM, from about 0.0200 nM to about 1 nM, from about 0.0200 nM to about 0.800 nM, from about 0.0200 nM to about 0.600 nM, from about 0.0200 nM to about 0.400 nM, from about 0.0200 nM to about 0.200 nM, from about 0.0200 nM to about 0.100 nM, from about 0.0200 nM to about 0.0900 nM, from about 0.0200 nM to about 0.0800 nM, from about 0.0200 nM to about 0.0700 nM, from about 0.0200 nM to about 0.0600 nM, from about 0.0200 nM to about 0.0500 nM, from about 0.0200 nM to about 0.0400 nM, or from about 0.0200 nM to about 0.0300 nM.

In certain aspects, the concentration of the at least one, at least two, at least three, or more compounds used to decrease polyunsaturated triacylglycerol production in algae or yeast is at least about 0.0200 nM, at least about 0.0210 nM, at least about 0.0220 nM, at least about 0.0230 nM, at least about 0.0240 nM, at least about 0.0250 nM, at least about 0260 nM, at least about 0.0270 nM, at least about 0.0280 nM, at least about 0.0290 nM, at least about 0.0300 nM, at least about 0.0350 nM, at least about 0.0400 nM, at least about 0.0450 nM, at least about 0.0500 nM, at least about 0.0550 nM, at least about 0.0600 nM, at least about 0.0650 nM, at least about 0.0700 nM, at least about 0.0750 nM, at least about 0.0800 nM, at least about 0.0850 nM, at least about 0.0900 nM, at least about 0.0950 nM, at least about 0.1000 nM, at least about 0.200 nM, at least about 0.225 nM, at least about 0.300 nM, at least about 0.400 nM, at least about 0.500 nM, at least about 0.600 nM, at least about 0.650 nM, at least about 0.660 nM, at least about 0.670 nM, at least about 0.680 nM, at least about 0.690 nM, at least about 0.700 nM, at least about 0.750 nM, at least about 0.800 nM, at least about 0.850 nM, at least about 0.900 nM, at least about 0.950 nM, at least about 1 nM, at least about 1.5 nM, at least about 2 nM, at least about 2.5 nM, at least about 3 nM, at least about 3.5 nM, at least about 4 nM, at least about 4.5 nM, at least about 5 nM, at least about 5.5 nM, at least about 6 nM, at least about 6.5 nM, at least about 7 nM, at least about 7.5 nM, at least about 8 nM, at least about 8.5 nM, at least about 9 nM, at least about 9.5 nM, at least about 10 nM, at least about 10.5 nM, at least about 11 nM, at least about 11.5 nM, at least about 12 nM, at least about 12.5 nM, at least about 13 nM, at least about 13.5 nM, at least about 14 nM, at least 14.5 nM, at least about 15 nM, at least about 15.5 nM, at least about 16 nM, at least about 16.5 nM, at least about 17 nM, at least about 17.5 nM, at least about 18 nM, at least about 18.5 nM, at least about 19 nM, at least about 19.5 nM, at least about 20 nM, at least about 21 nM, at least about 22 nM, at least about 23 nM, at least about 24 nM, at least about 25 nM, at least about 26 nM, at least about 27 nM, at least about 28 nM, at least about 29 nM, at least about 30 nM, at least about 31 nM, at least about 32 nM, at least about 33 nM, at least about 34 nM, at least about 35 nM, at least about 36 nM, at least about 37 nM, at least about 38 nM, at least about 39 nM, at least about 40 nM, at least about 41 nM, at least about 42 nM, at least about 43 nM, at least about 44 nM, at least about 45 nM, at least about 46 nM, at least about 47 nM, at least about 48 nM, at least about 49 nM, at least about 50 nM, at least about 51 nM, at least about 52 nM, at least about 53 nM, at least about 54 nM, at least about 55 nM, at least about 56 nM, at least about 57 nM, at least about 58 nM, at least about 59 nM, at least about 60 nM, at least about 61 nM, at least about 62 nM, at least about 63 nM, at least about 64 nM, at least about 65 nM, at least about 66 nM, at least about 67 nM, at least about 68 nM, at least about 69 nM, at least about 70 nM, at least about 71 nM, at least about 72 nM, at least about 73 nM, at least about 74 nM, at least about 75 nM, at least about 76 nM, at least about 77 nM, at least about 78 nM, at least about 79 nM, at least about 80 nM, at least about 81 nM, at least about 82 nM, at least about 83 nM, at least about 84 nM, at least about 85 nM, at least about 86 nM, at least about 87 nM, at least about 88 nM, at least about 89 nM, at least about 90 nM, at least about 91 nM, at least about 92 nM, at least about 93 nM, at least about 94 nM, at least about 95 nM, at least about 96 nM, at least about 97 nM, at least about 98 nM, at least about 99 nM, at least about 100 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 185 nM, at least about 190 nM, at least about 195 nM, at least about 200 nM, at least about 225 nM, at least about 250 nM, at least about 275 nM, at least about 300 nM, at least about 325 nM, at least about 350 nM, at least about 375 nM, at least about 400 nM, at least about 425 nM, at least about 450 nM, at least about 475 nM, at least about 500 nM, at least about 525 nM, at least about 550 nM, at least about 575 nM, at least about 600 nM, at least about 625 nM, at least about 650 nM, at least about 655 nM, at least about 660 nM, at least about 665 nM, at least about 670 nM, at least about 675 nM, at least about 680 nM, at least about 685 nM, at least about 690 nM, at least about 695 nM, at least about 700 nM, at least about 725 nM, at least about 750 nM, at least about 775 nM, at least about 800 nM, at least about 825 nM, at least about 850 nM, at least about 875 nM, at least about 900 nM, at least about 925 nM, at least about 950 nM, at least about 975 nM, at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 5.5 µM, at least about 6 µM, at least about 6.5 µM, at least about 7 µM, at least about 7.5 µM, at least about 8 µM, at least about 8.5 µM, at least about 9 µM, at least about 9.5 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 21 µM, at least about 22 µM, at least about 23 µM, at least about 24 µM, at least about 25 µM, at least about 26 µM, at least about 27 µM, at least about 28 µM, at least about 29 µM, at least about 30 µM, at least about 31 µM, at least about 32 µM, at least about 33 µM, at least about 34 µM, at least about 35 µM, at least about 36 µM, at least about 37 µM, at least about 38 µM, at least about 39 µM, at least about 40 µM, at least about 41 µM, at least about 42 µM, at least about 43 µM, at least about 44 µM, at least about 45 µM, at least about 50 µM, at least about 55 µM, at least about 60 µM, at least about 65 µM, at least about 70 µM, at least about 75 µM, at least about 80 µM, at least about 85 µM, at least about 90 µM, at least about 95 µM, or at least about 100 µM.

Methods of Producing Biofuels

Other aspects of the present disclosure relate to methods of producing biofuels from the lipids produced by algal or yeast cell populations treated with at least one, at least two, at least three, or more compounds, such as such as lipoxygenase inhibitors, kinase inhibitors, phosphatase inhibitors, kinase inhibitors or activators, lipase inhibitors, or oxidative signaling compounds. Such lipids may be obtained from algal or yeast cell populations that have been treated with at least one, at least two, at least three, or more compounds to increased lipid levels in the cell population; from algal or yeast cell populations that have been treated with the at least one, at least two, at least three, or more compounds to produce saturated triacylglycerols or monounsaturated triacylglycerols in the cell population; or from algal or yeast cell populations that have been treated with the at least one, at least two, at least three, or more compounds to decrease polyunsaturated triacylglycerol production in the cell population.

Biofuels include, without limitation, ethanol, propanol, biodiesel, and biodiesel derivatives and other fatty acid derivatives. Biodiesel may refer generally to plant oil-, animal fat-, or algal or yeast lipid-based diesel fuel composed mainly of long-chain alkyl, methyl, propyl, or ethyl esters (i.e., fatty acid esters), though it can include other fatty acids, and terpenoids. Biodiesel equivalents and other fatty acid derivatives include, without limitation, wax esters, fatty alcohols, and fatty aldehydes.

Certain aspects provide for isolated lipids produced from the methods of the present invention, which are subsequently processed into biofuels of the present disclosure. Isolating the lipids involves separating at least part or all of the cells of an algal or yeast cell population from the isolated lipids. The lipids may be free or essentially free of impurities formed from at least part or all of the cells of the algal or yeast cell population. The isolated lipids are essentially free of these impurities when the amount and properties of the impurities do not interfere in the use of the lipids to produce a fuel, such as a fuel in a combustion reaction. Isolated lipids of the present disclosure can then be converted into biofuels, such as biodiesel, by any methods known in the art. For example, isolated lipids, or fractions thereof, may be converted into fatty acid esters, fatty alcohols, fatty aldehydes, or terpenoids by any chemical, biological, or enzymatic process known in the art.

In some aspects, algal and yeast cells of the present disclosure naturally produce biofuels, such as biodiesel, from lipids.

In other aspects, algal and yeast cells of the present disclosure do not naturally produce biofuels, such as biodiesel, from lipids. Such algal and yeast cells may be engineered to heterologously express the one or more genes necessary for the algal or yeast cell to produce biofuels from lipids.

It is to be understood that, while the methods and compositions disclosed herein have been described in conjunction with the preferred embodiments thereof, the foregoing description is intended to illustrate and not limit the scope thereof as defined in the appended claims. Other aspects, advantages, and modifications within the scope thereof as defined in the appended claims will be apparent to those skilled in the art to which the present disclosure pertains.

All patents, patent applications, and publications mentioned herein are hereby incorporated by reference in their entireties.

EXAMPLES

The following Examples describes a three-phase process to identify small molecule probes as chemical triggers to increase lipid levels and compare the chemical effects on multiple algae strains containing high lipid or hydrocarbon content for biofuel production (FIG. 1). The initial screening phase utilized 96-well microplates to screen multiple compounds and algae strains, and the final screening phase test lead compounds in 500-mL batch cultures, where traditional techniques of lipid analysis could also be performed. The high throughput assay was developed to monitor cell growth and intracellular lipid levels in microplates, using absorbance and chlorophyll fluorescence measurements during all growth phases followed by the addition of a lipophilic dye (Nile Red, 9-diethylamino-5H-benzo[alpha]phenoxazine-5-one) in stationary phase.[22] A diverse collection of bioactive small molecules was selected based on targets that may be involved in lipid signaling pathways related to lipid metabolism/catabolism. The positive hits identified as lead compounds in the microplate assay were then evaluated in a more focused manner, first with dose-response screening in microplates, and then in larger 500 mL cultures to quantify and compare lipid levels and composition using gravimetric analysis, $^1$H NMR spectroscopy, microscopy, and direct mass spectrometric analysis (MALDI-TOF and GCMS).[23] These techniques also facilitated the pre-characterization of fuel properties in order to attain desired properties of biodiesel (such as volatility and viscosity)[24] where small changes resulting from unsaturation or chain length can have a substantial effect on fuel properties.[25,26]

The results show that compounds identified in the microplate screening assay can be used in larger cultures to increase both the biomass and lipid levels in algae. Using only nanomolar concentrations in 500 mL cultures, we have identified conditions that increase lipid levels by at least two-fold. Furthermore, we have identified compounds that can alter the triacylglycerol (TAG) fatty acid saturation levels to target desired biodiesel properties. The results show that chemical triggers increased lipid levels in algae, and match the lipid/cell levels typically observed under nitrogen-deficient conditions, but without the overall decrease in cell mass.

Example 1

The following Example relates to the identification and characterization of chemical triggers that increase lipid production in microalgae.

Materials and Methods

Algae Strains and Culture Conditions

Algal species grown for this study were purchased from the UTEX Culture Collection of Algae at the University of Texas, Austin USA (*Phaeodactylum tricornutum* UTEX B2089, *Nannochloropsis oculata* UTEX LB2164, *Nannochloris* sp. UTEX LB2055, the Provasoli-Guillard Center for the Culture of Marine Phytoplankton (CCMP) at Bigelow Laboratory for Ocean Sciences, Massachusetts, USA (*Nannochloropsis salina* CCMP 537). *P. tricornutum* and *N. salina* were grown in F/2 medium (prepared from stocks from CCMP) while *N. oculata* and *Nannochloris* sp. were cultured in Erdschrieber's medium (prepared as indicated by UTEX) as indicated by the specific algae's culture center. Stock cultures were aerated by stirring with bubbling air (homemade manifold with Petco air pump, 2-4% $CO_2$) or by orbital shaking (Thermo Scientific MAXQ 2000) at a constant speed of 150 rpm at 22±3° C. with a 16:8 hour light/dark cycle. Stocks were kept at stationary phase for use. Algae were prepared as dictated by culture center.

High Throughput Assay Part 1: Preparation of Algae for Assay

TABLE 9

| Culture number | Species | Media |
| --- | --- | --- |
| UTEX B2089 | *Phaeodactylum tricornutum* | F/2 |
| CCMP 537 | *Nannochloropsis salina* | F/2 |
| UTEX LB2164 | *Nannochloropsis oculata* | Erdschrieber's |
| UTEX LB2055 | *Nannochloris* sp. | Erdschrieber's |

High Throughput Assay Part 2: Preparation of Compound Stock Solutions for Assay

Compounds were selected based on reported biological activity in non-microalgae organisms. To ensure that compounds retained their quality, they were stored under advised conditions after purchasing from the manufacturer. Solutions of all assay compounds were prepared as 10 mM stock solutions by dissolving in DMSO in 2-dram amber vials and then stored in darkness −20° C. 96-well PCR plates were used to create a stock plate layout that was then transferred to the algae microplates. A plate map was used to distribute each compound to a well based on molecule name, collection number, and CAS number. For 20 µM and 200 nM assay plates, 10 mM compound stock in DMSO was diluted into plate maps of 5 mM and 50 µM assay stocks, respectively. Table 10 lists the selected compounds, the vendor used to obtain the compounds, and the catalog number for each compound.

TABLE 10

| Molecule | Catalog # | Vendor |
| --- | --- | --- |
| (−) flurbiprofen | 215816301 | MP Biomedicals Inc |
| (−)-Epicatechin | 5125 | Chromadex Chemicals |
| (−)-Epicatechin Gallate | 5135 | Chromadex Chemicals |
| (−)-Epigallocatechin | 5145 | Chromadex Chemicals |
| (−)-Epigallocatechin Gallate | NC9045247 | Axxora LLC. |

TABLE 10-continued

| Molecule | Catalog # | Vendor |
| --- | --- | --- |
| (−)-Epigallocatechin Gallate | 5150 | Chromadex Chemicals |
| (+)-Catechin | 3310 | Chromadex Chemicals |
| 2-arachidonylglycerol | 181251 | EMD Chemicals Inc. |
| 2-methylthio ATP | 119126 | EMD Chemicals Inc. |
| 3,4-dephostatin | 263202 | EMD Chemicals Inc. |
| Abscisic acid | ICN19067380 | MP Biomedicals Inc. |
| Acetaminophen | AC10233-2500 | Acros Organics |
| AG 112 | 658440 | EMD Chemicals Inc. |
| AG 1288 | 658510 | EMD Chemicals Inc. |
| AG 183 | 658410 | EMD Chemicals Inc. |
| AG 30 | 121760 | EMD Chemicals Inc. |
| AG 99 | 658430 | EMD4 Biosciences Inc. |
| AG82 | 658400 | EMD Chemicals Inc. |
| AICAR | A9978 | Sigma Aldrich |
| Aloisine A | 128125 | EMD Millipore |
| Aloisine, RP106 | 128135 | EMD Chemicals Inc. |
| apigenin | 80055-806 | EMD Millipore |
| arctigenin | 50810264 | Tocris Cookson |
| atrazine | 1912-24-9 | Cayman Chemical Inc. |
| Baicalein | A385022M005 | Axxora LLC. |
| benzylaminopurine | AC22641-0010 | Acros Organics |
| BHA | IC10115980 | MP Biomedicals Inc |
| BHQ | 286888 | EMD Chemicals Inc. |
| bisindolylmaleimide | A270-019-M001 | Axxora LLC. |
| bohemine | 203600 | EMD Chemicals Inc. |
| (4-[(3-bromophenyl)amino]-6,7-diaminoquinazoline) | 203697 | EMD Chemicals Inc. |
| BPIQ | 203696 | EMD Chemicals Inc. |
| BPIQ-II | 80108-822 | EMD Millipore |
| Butein | 80050-502 | EMD Millipore |
| Caffeic acid | A270231G001 | Axxora LLC. |
| caffeine | AA3921414 | Cen-Med Enterprises |
| cAMP, sodium salt hydrate | AC22821-1000 | Acros Organics |
| Cantharidin | 210155 | EMD4Biosciences Inc. |
| CDC25 Phosphatase Inhibitor I | 217691 | EMD Chemicals Inc. |
| CDK2 inhibitor II | 80510-390 | EMD Millipore |
| CDK2 inhibitor IV | 238804 | EMD Chemicals Inc. |
| CDK4 Inhibitor | 219476 | EMD Chemicals Inc. |
| CDK4 Inhibitor II NSC | 219477 | EMD Chemicals Inc. |
| CDK4 Inhibitor III | 219478 | EMD Chemicals Inc. |
| CDK4/6 Inhibitor IV | 219492 | EMD Chemicals Inc. |
| Cerulinin | ICN19509801 | MP Biomedicals Inc. |
| cilostazol | 50810589 | Tocris Cookson |
| citric acid monohydrate | AC12491-0250 | Acros Organics |
| Clotrimazole | NC9956111 | Calbiochem |
| coenzyme A | BP251025 | Fisher Bioreagents |
| COX-1 Inhibitor 2 | 236006 | EMD Chemicals Inc. |
| Curcumin | AC21858-0100 | Acros Organics |
| cycloheximide | AC35742-0010 | Acros Organics |
| D-Glucosamine hydrochloride | AC11990-0100 | Acros Organics |
| Daphnetin | 268295 | EMD Chemicals Inc. |
| dephostatin | 263200 | EMD Chemicals Inc. |
| diniconazole | 50-735-67 | Crescent chemical co inc. |
| DMSO | D136-1 | ThermoFischer |
| DNA-PK inhibitor IV | 260963 | EMD Chemicals Inc. |
| Eicosapentaenoic acid | NC9297605 | Cell Signalling technologies |
| emodin | 219045350 | MP Biomedicals Inc |
| epinephrin | ICN15106401 | MP Biomedicals Inc. |
| Erbstatin analog | ICN15881305 | MP Biomedicals Inc |
| esculetin | E0386-1G | TCI America |
| ET-18-OCH3 | 341207 | EMD Chemicals Inc. |
| Ethyl 3,4-Dephostatin | 263203 | EMD Chemicals Inc. |
| ethyl palmitate | AC41031-0050 | Acros Organics |
| F16 | 341246 | EMD Chemicals Inc. |
| FAAH Inhibitor I | 341248 | EMD Chemicals Inc. |
| FAAH Inhibitor II | 341249 | EMD Chemicals Inc. |
| Fluconazole | NC9254916 | Calbiochem |
| forskolin | BP25201 | Fisher Bioreagents |
| fructose | AC16135-5000 | Acros Organics |
| genistein | AC32827-0250 | Acros Organics |
| gibberellic acid | AC41091-0010 | Acros Organics |
| glucose | AC24192-2500 | Acros Organics |
| glycerol | G31-1 | ThermoFischer |
| gossypol | 219521083 | MP Biomedicals Inc |
| GSK-3 inhibitor 13 | 361555 | EMD Chemicals Inc. |
| Halopamide | Sigma Aldrich | H3041 |
| Halopemide | H3041 | Sigma Aldrich |
| HDSF | 373250 | EMD Chemicals Inc. |

TABLE 10-continued

| Molecule | Catalog # | Vendor |
|---|---|---|
| hepoxilin A (empty) | 375425 | EMD Chemicals Inc. |
| Ibuprofen | AC33320-0010 | Acros Organics |
| Indole acetic acid (IAA) | AC122160100 | Acros Organics |
| indole-3-butyric acid | ICN10204301 | MP Biomedicals Inc. |
| indomethacin | A19910-06 | Alfa Aesar Inc |
| indomethacin ester, 4-methoxyphenyl | 405271 | EMD Chemicals Inc. |
| jasmonic acid | 50213381 | Research Products International Corp |
| JZL 184 Hydrate | J3455 | Sigma Aldrich |
| K-252a (100 UG) | NC9265013 | Enzo Life Sciences |
| Kenpaullone | NC9448126 | Enzo Life Sciences |
| ketoconazole | BP2734-50 | Fisher Bioreagents |
| Kinetin | AC22650-0010 | Acros Organics |
| lactic acid | BP26615 | Fisher Bioreagents |
| SB 202190 | 50-810-911 | Tocris Cookson |
| MEG, hydrochloride | 444600 | EMD Chemicals Inc. |
| Melatonin | 80057-004 | EMD Millipore |
| methyl jasmonate | M1068-5G | TCI America |
| MJ33 | 475865 | EMD Chemicals Inc. |
| MMP-2/MMP-3 Inhibitor II | 444240 | EMD Chemicals Inc. |
| N,N''-Di-sec-butyl-p-phenylenediamine | TCD2268 | TCI America |
| Naproxen | ICN19024705 | MP Biomedicals Inc. |
| napththyl acid phosphate | 479775-5GM | EMD Chemicals Inc. |
| Olomoucine | PRV2373 | Promega Corp |
| Orlistat (lipase inhibitor, THL) | 437701 | EMD Chemicals Inc. |
| Oxindole 1 | 499600 | EMD Chemicals Inc. |
| paclobutrazol | NC9369428 | Chem Service Inc |
| Palmityl trifluoromethylketone | P8727 | Sigma Aldrich |
| PD 156273 | 513032 | EMD Chemicals Inc. |
| pd98059 mek1 inhibitor | NC9920928 | Cell Signalling technologies |
| PFMRK inhibitor | 528140 | EMD Chemicals Inc. |
| Phenylarsine oxide | 521000 | EMD Chemicals Inc. |
| Phloretin | AC307651000 | Acros Organics |
| Phorbol 12-Myristate 13-Acetate | NC9325685 | LC Laboratories |
| piceatannol | 527948-1MG | EMD Chemicals Inc. |
| PP2-4-Amino-5-(4-chlorophenyl)-7-(t-butyl) pyrazolo[3,4-d]pyrimidine | 529573 | Andwin Scientific |
| Propyl Gallate | AC131581000 | Acros Organics |
| PTP Inhibitor II | 540205-25MG | EMD4Biosciences Inc. |
| quercetin | AC17407-0100 | Acros Organics |
| quinacrine | ICN15200425 | MP Biomedicals Inc. |
| quinazoline | B24094-03 | Alfa Aesar Inc |
| Rapamycin | NC9362949 | LC Laboratories |
| resveratrol | 80057-450 | EMD Millipore |
| RHC 80267 | R2028 | Sigma Aldrich |
| Roscovitine | 557360 | Andwin Scientific |
| Salicylic acid | ICN10257780 | MP Biomedicals Inc |
| SCH-202676 | 565645 | EMD Chemicals Inc. |
| SMC prolif. Inhibitor 2W | 573117 | EMD Chemicals Inc. |
| Sodium Orthovanadate | ICN15966410 | MP Biomedicals Inc. |
| Staurosporine | BP2541100 | Fisher Bioreagents |
| SU9516 | 572650 | EMD Chemicals Inc. |
| T113242 | 575307 | EMD Chemicals Inc. |
| Tetrahydrolipstatin (orlistat) | O4139 | Sigma Aldrich |
| Theobromine | AC258821000 | Acros Organics |
| thiamine | 148990100 | Acros Organics |
| Thidiazuron | NC9071755 | Chem Service Inc |
| Trans-HR22C16 | 385861 | EMD Chemicals Inc. |
| Tyrene CR4 | 655230 | EMD Chemicals Inc. |
| U-74389G | 662046 | EMD Chemicals Inc. |
| U0125 | 662008 | EMD Chemicals Inc. |
| URB602 | 10007457 | Cayman Chemical Inc. |
| virstatin | 677520 | EMD4Bioscience Inc. |
| Vitamin E | AAAL09231-18 | Lab Source Inc. |
| Zeatin | AC26429-0100 | Acros Organics |

High Throughput Assay Part 3: Assay Procedure

Media was made specific to algae species as dictated by the culture center (CCMP or UTEX). Assay plates were filled with algae cells in 150 µL of media (Microflo Select, Biotek, Vermont, USA), and grown in Parafilm-sealed microplates (Corning 3370) for the entire growth period to prevent evaporation. Biotek Gen 5 (Biotek, Vermont, USA) software was used to collect data. For some species, supplemental sodium bicarbonate was added to maintain standard growth levels, based on preliminary studies in plates. Controls consisted in each plate as all the wells in Column 1, consisting of only DMSO. For each algae species, growth experiments were first performed with varying levels of sodium bicarbonate to determine if the supplemental carbon is required for optimal microplate growth. Microplate growth experiments were performed with a gradient of sodium bicarbonate (0.16-1.2 g/L)

in media, and tested both with and without the addition of 1 µL (0.4%) of DMSO. Based on analysis of these growth experiments, it was determined that an overall well concentration of 1.2 g/L sodium bicarbonate was to be added as a supplement for the growth of *P. tricornutum* and *N. salina* in F/2 media. No supplemental sodium bicarbonate was added to *N. oculata* and *Nannochloris* sp. in Erdschrieber's media.

All materials for assay experiments were autoclaved before each use to maintain axenic algae cultures. Algae species were checked for homogeneity using a TS-100 light microscope (Nikon, Japan). For each microplate, 10 mL of diluted algae stock was prepared by diluting a stationary phase culture to 0.075 absorbance units with appropriate media without sodium bicarbonate supplementation. Diluted stock solutions were made immediately prior to use for consistency and optimal plate growth. Cell density was measured on a Thermo Scientific Genesys 10S Vis Spectrophotometer (ThermoFisher, San Jose), using a 1 mL cuvette at 680 nm.

Plates were originally run in triplicate, before replicates were increased to quadruplicate, along with a separate control plate to compare growth. Due to extensive evaporation in exterior wells over time, our unique algae plate layout was designed to use the 60 interior wells out of 96 wells for the experiment. The 36 outer wells were filled with Millipore water and media to prevent evaporation and edge effects in the inner algae wells, as well as serve as blanks. The 60 wells with algae contained a total volume of 251 µL (100 µL of media+ DMSO compound stock +150 µL dilute algae stock). For 20 µM and 200 nM assay plates, 10 mM compound stock in DMSO is diluted into plate maps of 5 mM and 50 µM assay stocks, respectively. The DMSO stock solution was added first to the microplate so that the exothermic reaction of DMSO and water does not negatively affect algae growth. Control wells had 1 µL DMSO added. Plates were parafilmed during growth to limit the amount of evaporation that can occur. Plates were numbered, and numerically ordered to ensure they got the same shaker space.

Subsequent screening of compounds also involved water based compound solutions to rule out DMSO effects.

The plates were grown under full spectrum incident uniform lighting at a 16:8 hour light/dark cycle with 90-150 µM photons/m$^2$/s (High Efficiency T-5 Grow Lights—Gardeners Supply Co, Vermont). The shakers are kept at a constant shaking of 150 rpm. Ambient temperature is 22±3° C. Absorbance (680 nm and 600 nm) and fluorescence (excitation at 430 nm→emission at 630 nm) was taken every day on the Synergy HT Plate Reader (Biotek, Vermont, USA), in order to monitor cell density and chlorophyll production in algae over the growth cycle.

The algae were grown to stationary phase, as indicated by a plateau in the growth rate over 1-4 days. The growth plateau should occur for more than one day to allow for appropriate lipid levels to accumulate; 3 days in stationary phase is typical of the assay. The assay plates of *N. salina*, *P. tricornutum*, and *N. oculata* are grown for 14 days and then analyzed with Nile Red by the method outlined below. *Nannochloris* sp. takes 21 days to reach stationary phase. The algae lipid levels can be analyzed at any stage in the growth cycle by the Nile Red Method outlined below.

Preparation of Lipid Analysis for Chemical Genetics Screen in Microplates

The Nile Red protocol was used to analyze intracellular lipids in microalgae grown in 96-well clear round flat bottom microplates (Costar 3370). Clear microplates were used to give maximum light exposure for growth of microalgae during the assay. Microalgae growth rate was monitored daily by measuring absorbance ($OD_{680}$) and chlorophyll fluorescence (excitation and emission wavelength of 360 and 645 nm) using the Biotek Synergy HT. Intracellular lipid levels were analyzed using the Nile Red protocol at approximately 3 days at stationary phase to allow for lipid accumulation.

Method A—Rapid Lipid Analysis of Green Microalgae

To a microplate containing algae (in media) grown to stationary phase, 25 µL of 1:1 (v/v) DMSO/media was added manually using a multichannel pipet and the microplate was vortexed with an IKA® MS 3 Digital plate shaker for 1 minute. Then, 25 µL of Nile red dye (1 mg/mL solution in acetone) was added manually to the microplate using a multichannel pipet. Immediately after Nile Red dye was added to all wells, the microplate was vortexed for ~30 seconds and inserted into the Biotek Synergy HT Multi-mode Microplate Reader, which had been preheated to 40° C. The microplate was allowed to sit inside the instrument avoiding ambient light for 10 minutes of staining time before analysis. Then fluorescence data was acquired at 40° C. using a 20-minute kinetic read with continuous shaking at intervals of 52 sec, automatically set by the instrument. Fluorescence was acquired with an excitation and emission wavelength of 530 and 590 nm, respectively. Fluorescence data selected for analysis/comparison is based on the maximum intensity from the kinetic read. A related Nile red procedure has been reported for analysis of whole cell microalgae suspension from a concentrated microalgae pellet.[22]

Method B—Modification to Method A for More Rapid Lipid Analysis

A modified procedure was developed for a more rapid lipid analysis by omitting the 10-minute staining time, reducing heating temperature to 35° C., and using an automated dispensing of Nile red dye. In the case of Diatoms, the heating was omitted. Nile Red fluorescence data is acquired immediately after dispensing Nile Red using a microplate dispenser (Biotek Microflo Select), which minimizes dispensing time and gives a more even dye exposure.

To a microplate containing algae (in media) grown to stationary phase, 25 µL of 1:1 (v/v) DMSO/media was added manually using a multichannel pipet and the microplate was vortexed with an IKA® MS 3 Digital plate shaker for 1 minute. Then, 25 µL of Nile red dye (1 mg/mL solution in acetone) was added to the microplate using a microplate dispenser (Biotek Microflo Select). After Nile Red dye was added to all wells, the microplate was vortexed for ~30 seconds and then immediately analyzed using the Biotek Synergy HT Spectrophotometer, which had been preheated to 35° C. Fluorescence data was acquired at 35° C. using a 20-minute kinetic read with continuous shaking at intervals of 52 sec. Fluorescence was acquired with an excitation wavelength of 530 nm and an emission wavelength of 590 nm. Fluorescence data selected for analysis is based on the maximum intensity from the kinetic read.

All intracellular lipid analysis of diatoms was also performed without the 10 minute staining time and at room temperature.

Post-HTS Analysis—Follow Up Assays—Batch Cultures

Scale up from microplate wells to 500 mL batch cultures were the next step in compound efficacy validation. Batch cultures were grown in 500 mL Pyrex media bottles with stirring and air bubbling (homemade manifold with Petco air pump, 2-4% $CO_2$). Incoming air was sterile filtered by Polyvent 4 disposable filters (Whatman, Kent, UK). The culture suspensions were maintained with continuous air sparging, continuous elliptical mixing at 100-110 rpm, temperature was maintained at 23±2° C., and full spectrum incident uniform lighting (High Efficiency T-5 Grow Lights—Gardeners Supply Co, Vermont) at a 16:8 hour light/dark cycle with 60-120 μM photons/m$^2$/s. To minimize bacterial contamination, all equipment and materials were autoclaved and media was added to flask in a Purifier Vertical Clean bench (Labconco, Kansas City, Mo.). Batch cultures began with microalgae cultures diluted to 0.075 absorbance. The amount of DMSO is standardized for all experiments to 0.4%.

For all compound cultures, the 2 mL DMSO stock solution was added to media (without algae) first and mixed well. Control cultures were grown without DMSO. DMSO controls consisted of 0.04-1.0% DMSO. After the addition of algae and media, the container was plugged with a bug stopper vented closure cap and mixed thoroughly. Absorbance is measured immediately for Day 0 analysis. Afterward, absorbance was measured every 1-2 days with a cuvette (1 mL volume) on the Thermo Scientific Genesys 10S V is Spectrophotometer (ThermoFisher, San Jose) at 680 nm.

Results

Screening Collection and Chemical Genetic Assay Results

We have designed a high-throughput microplate assay to identify compounds that modulate growth and lipid levels in microalgae. The oleaginous species evaluated in this assay were *Phaeodactylum tricornutum*, *Nannochloropsis salina*, *Nannochloropsis oculata*, and *Nannochloris* sp. The microplate assays utilized sodium bicarbonate or soil extract as supplemental carbon sources because air or $CO_2$-bubbling is not feasible and limited air exchange occurs. Adding an external inorganic carbon source also ensures more consistent growth conditions and allows comparative studies resulting from compound treatment. Culture growth is monitored in microplates using optical cell density and chlorophyll fluorescence measurements throughout the growth phases. Nile Red is used as a lipophilic dye to detect intracellular lipids. Once stationary phase is reached, Nile Red analysis is performed using an optimized procedure for high throughput semi-quantitative measurement of intracellular lipids directly in microplates. Other lipophilic dyes and assays for lipid detection were also investigated and proved less reliable and difficult to adapt to a whole-cell high-throughput format.

Figure 2:
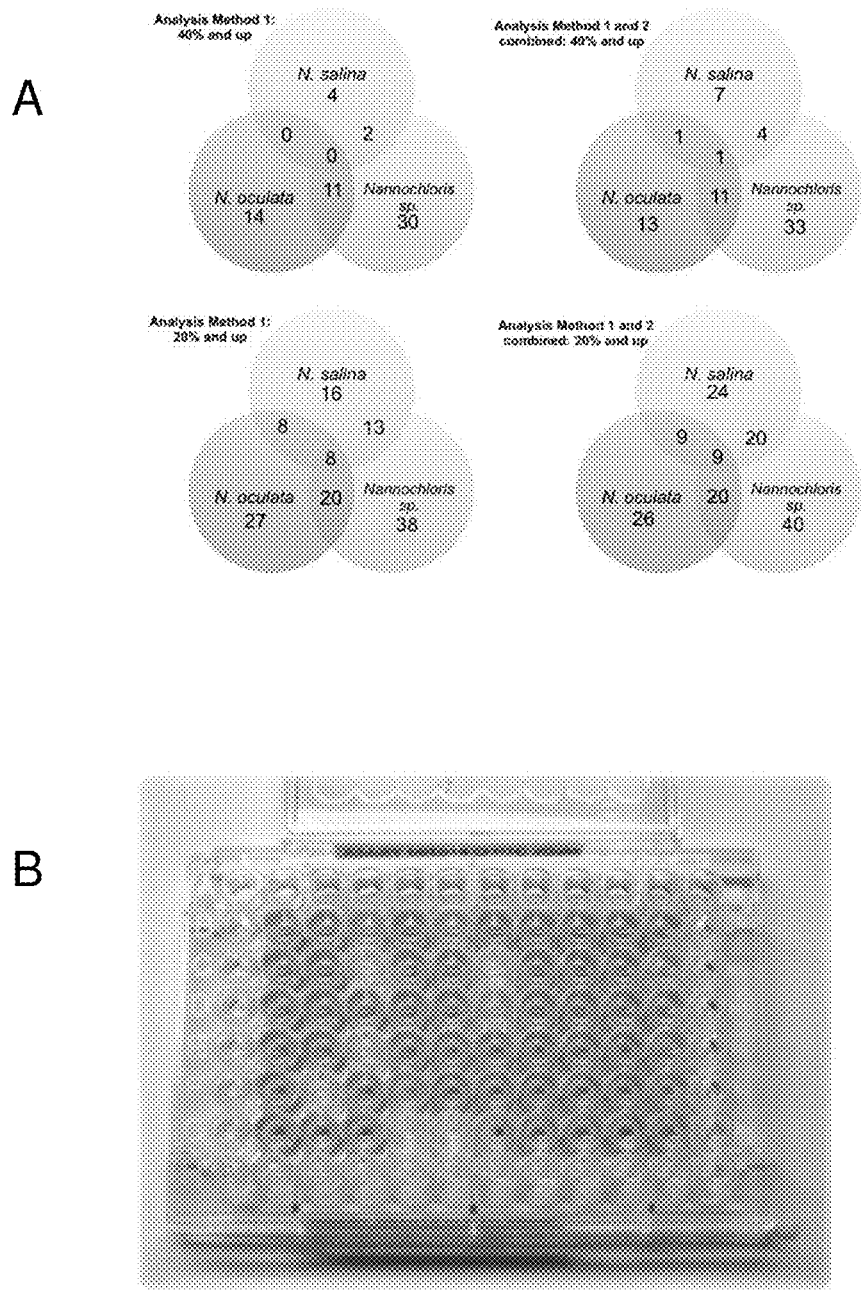
FIG. 2 depicts a summary of a high-throughput 54-compound screen results.
Figure 3:
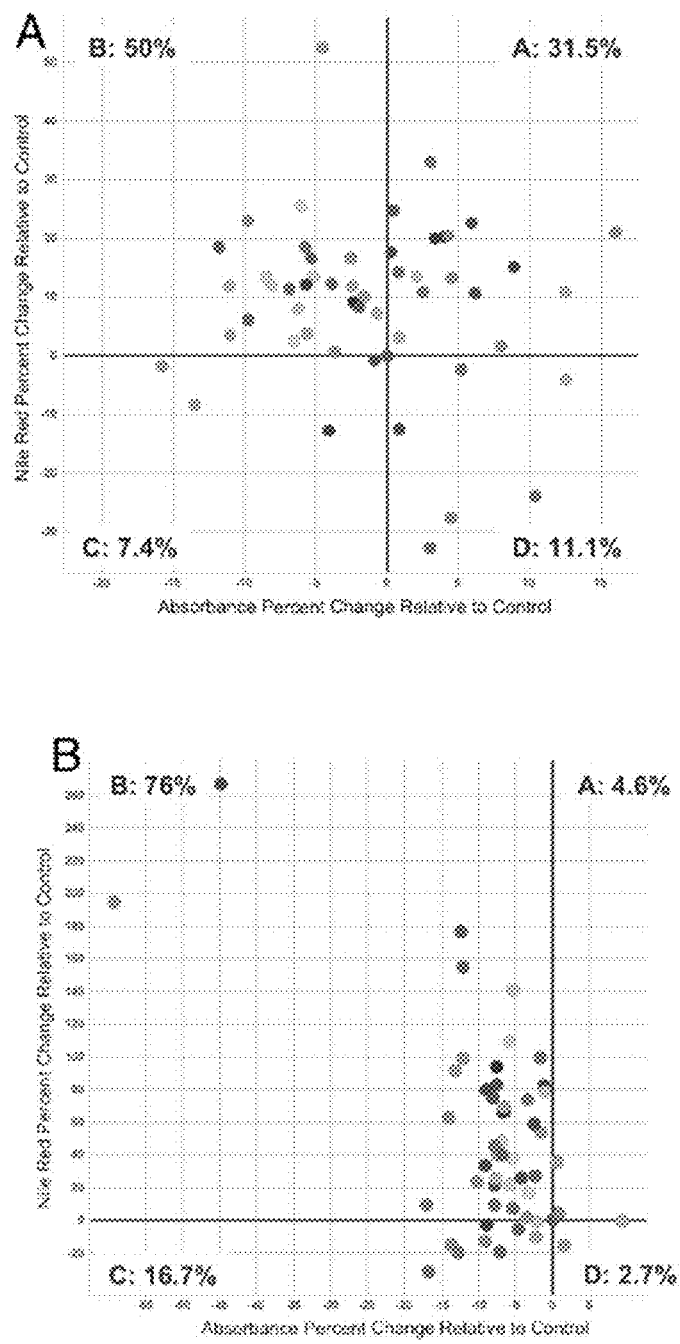
FIG. 3A depicts a 54-compound assay results for *N. oculata* plotted with absorbance on the x-axis and lipid production on the y-axis (as percent relative to control).
FIG. 3B depicts a 54-compound assay results for *Nannochloris* sp. plotted with absorbance on the x-axis and lipid production on the y-axis (as percent relative to control).
Figure 5:
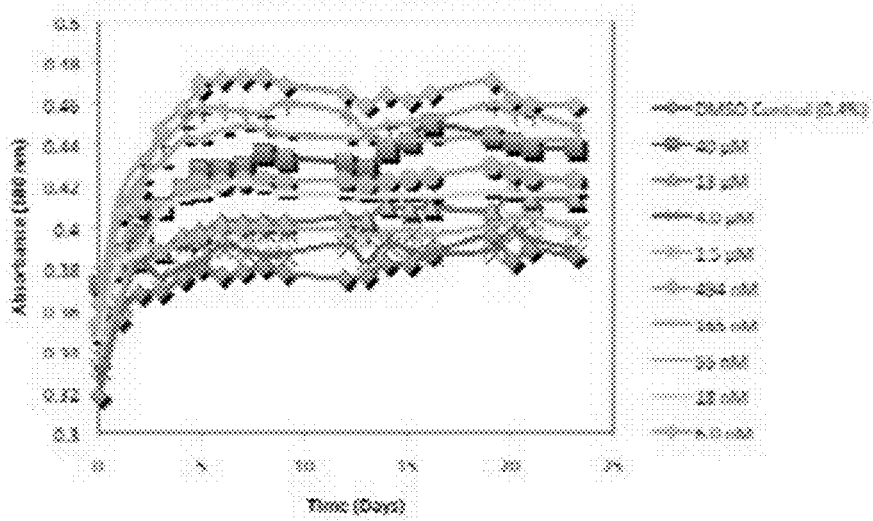
FIG. 5A depicts growth of *P. tricornutum* with varying concentrations of curcumin, a lipoxygenase inhibitor, using 96-well microplate. Compound wells contain 100 μL media+150 μL algae+Curcumin diluted in 1 μL of DMSO. Control wells contain 0.4% DMSO.
FIG. 5B depicts percent increase for absorbance and Nile red lipid measurement is relative to the DMSO control, based on day 16. Similar lipid increase was observed for *N. oculata* and *N. salina*.
Figure 6:
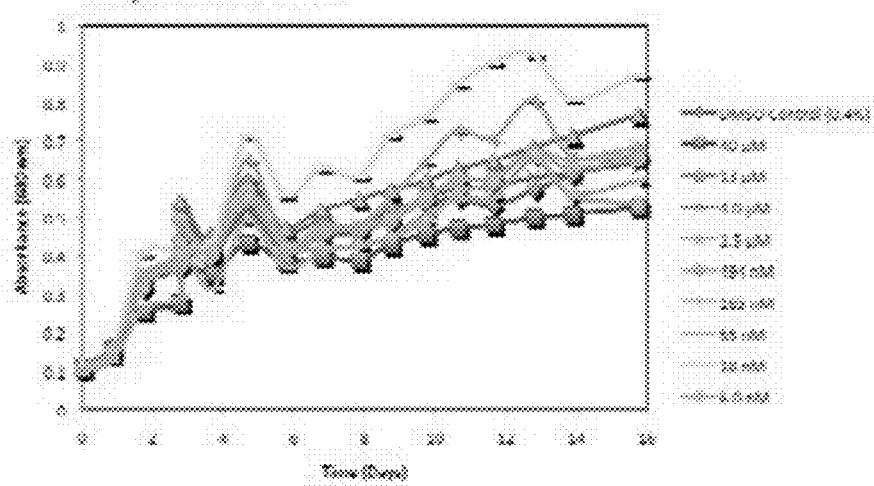
FIG. 6A depicts growth of *Nannochloris* sp. with varying concentrations of genistein, a protein kinase inhibitor, using 96-well microplate. Compound wells contain 100 μL media+150 μL algae+Curcumin diluted in 1 μL of DMSO. Control wells contain 0.4% DMSO.
FIG. 6B depicts percent increase for absorbance and Nile red lipid measurement is relative to the DMSO control, based on day 16.
Figure 7:
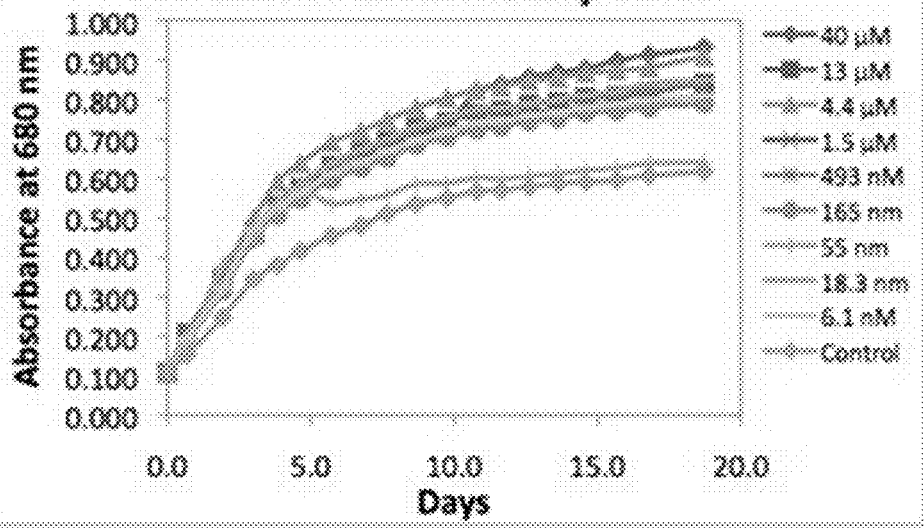
FIG. 7A depicts growth of *P. tricornutum* in 96-well plates tracked by absorbance with varying concentrations of glycerol. Compound wells contain 100 μL media+150 μL algae+glycerol diluted in 1 μL of DMSO. Control wells contain 0.4% DMSO.
FIG. 7B depicts percent increase for absorbance and Nile red lipid measurement is relative to the DMSO control, based on day 16.
Figure 8:
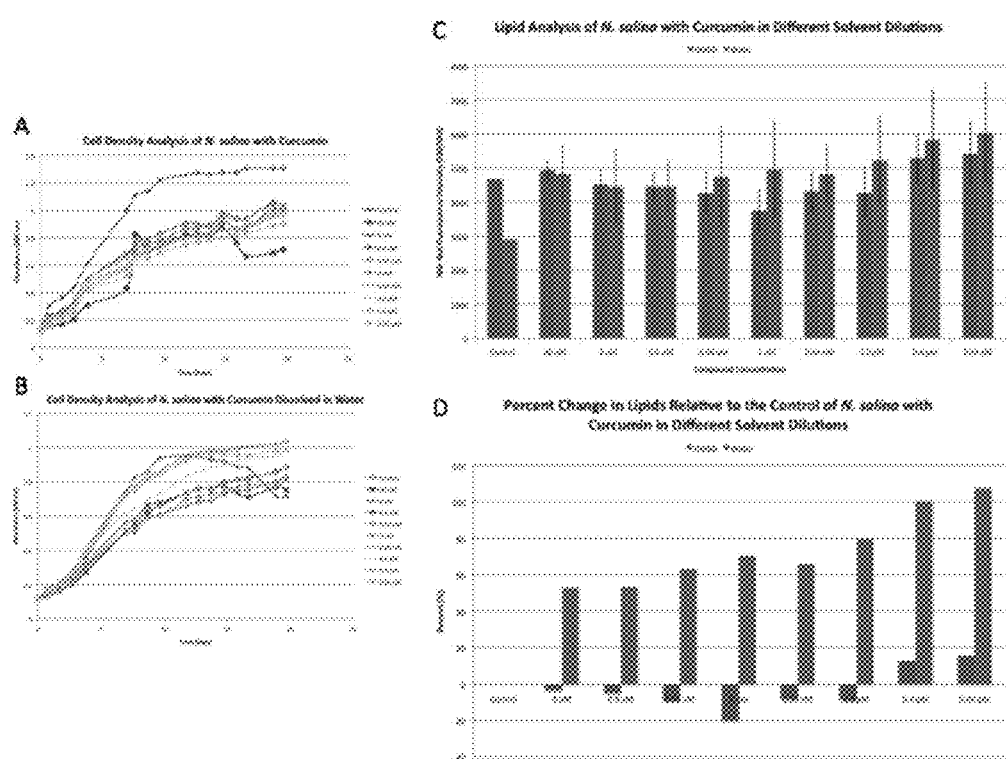
FIG. 8A depicts algae growth rate based on cell density for *N. salina* treated with curcumin dissolved in DMSO.
FIG. 8B depicts algae growth rate based on cell density for *N. salina* treated with curcumin dissolved in water.
FIG. 8C depicts the maximum Nile Red fluorescence intensity from three replicates with error bars compared between water and DMSO.
FIG. 8D depicts the average percent change relative to the control wells in the same plate compared between water and DMSO. Control wells have ~$10^{-5}$ standard deviation and error bars are not visible. The cell density curves correlate with the chlorophyll production in both solvent dilutions.
Figure 9:
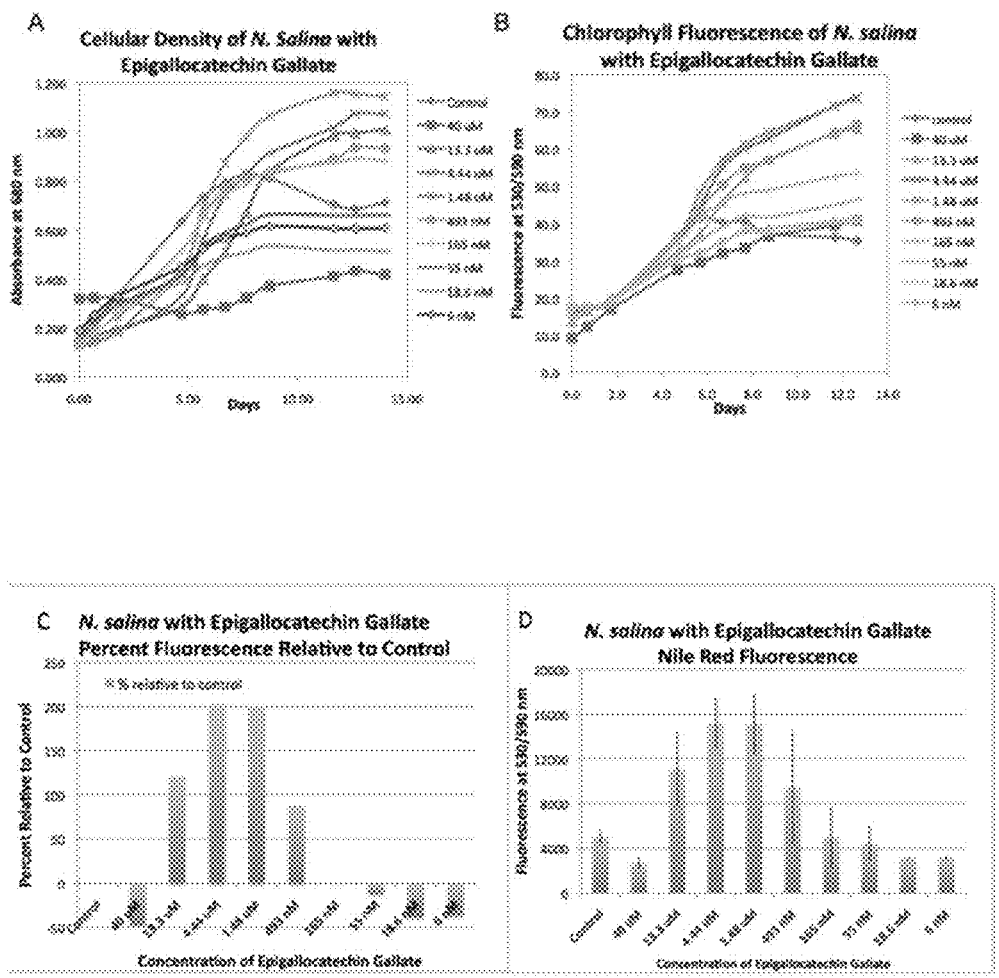
FIG. 9 depicts screening results for *N. Salina* with epigallocatechin gallate at a concentration range of 40 μM to 6 nM, with six replicates.
Figure 10:
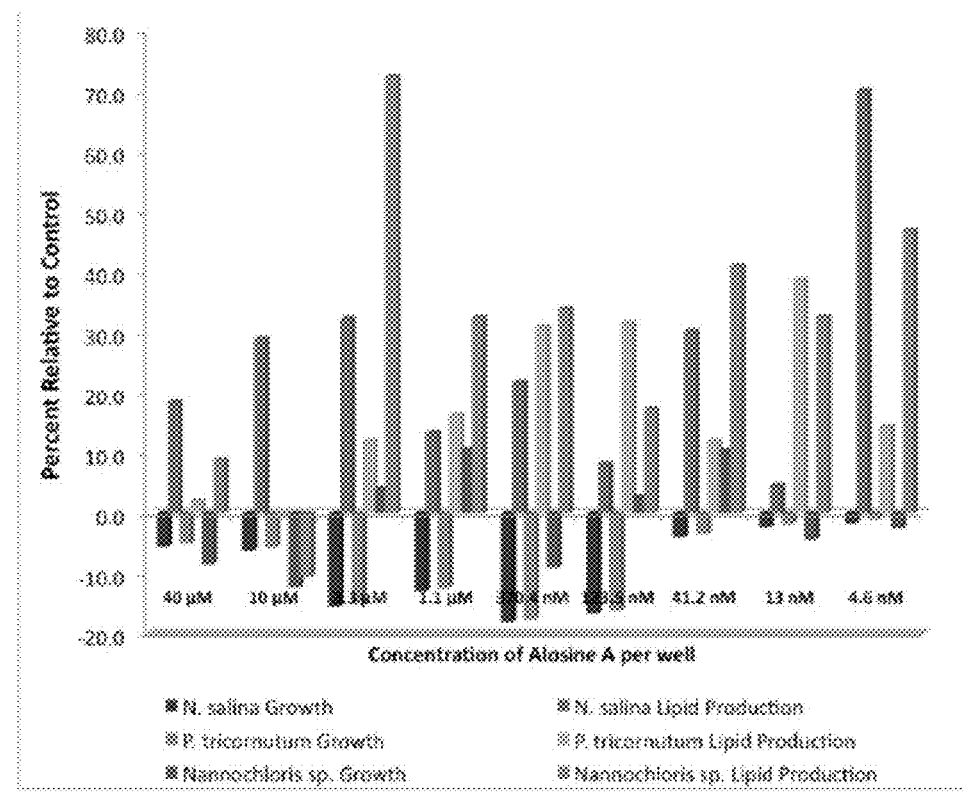
FIG. 10 depicts the effects of varying concentrations Aloisine A on three different algae strains. Compound wells contain 100 μL media+150 μL algae+Aloisine A diluted in 1 μL of DMSO. Control wells contain 0.4% DMSO. Lipid production is shown in the lighter colors, while growth is shown in correspondingly darker colors, with each species represented by a different color. Deviations are based on the average of the six replicates. Control is 0.4% DMSO, consistent with DMSO concentrations in compound wells. Algae growth was measure for 14 days, and then lipid production was measured with Nile Red.
Figure 11:
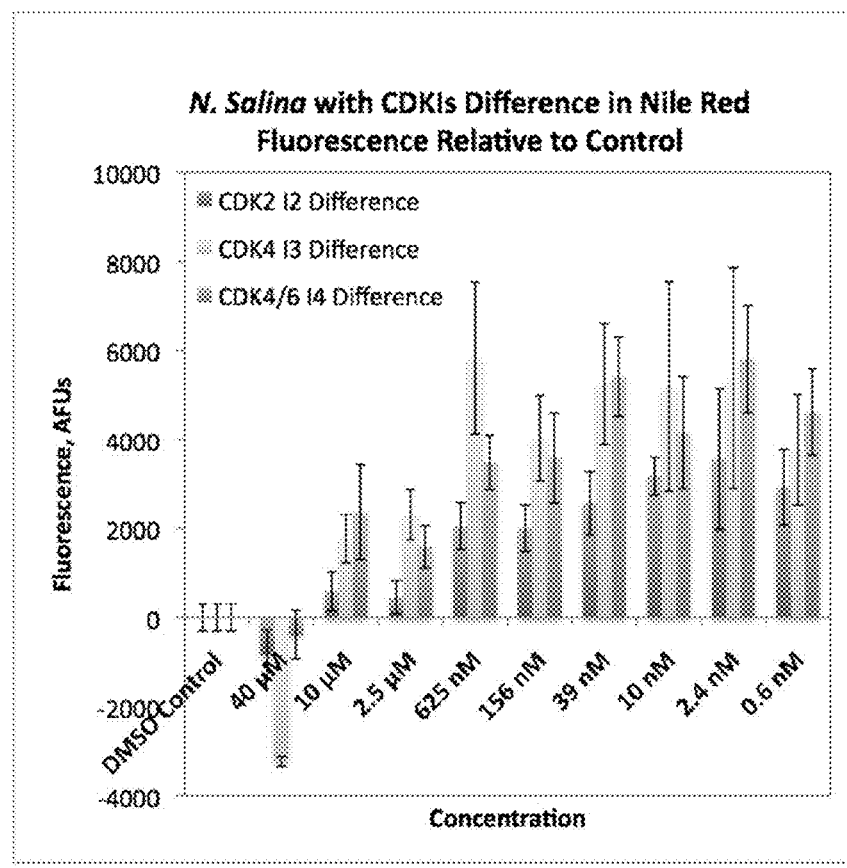
FIG. 11 depicts screening results for *N. Salina* with three CDK inhibitors at a concentration range of 40 μM to 0.6 nM, with four replicates comparing Nile Red fluorescence intensity relative to the control, which is set to zero. Compound wells contain 100 μL media+150 μL algae+compound diluted in 1 μL of DMSO. Control wells contain 0.4% DMSO.
Figure 13:
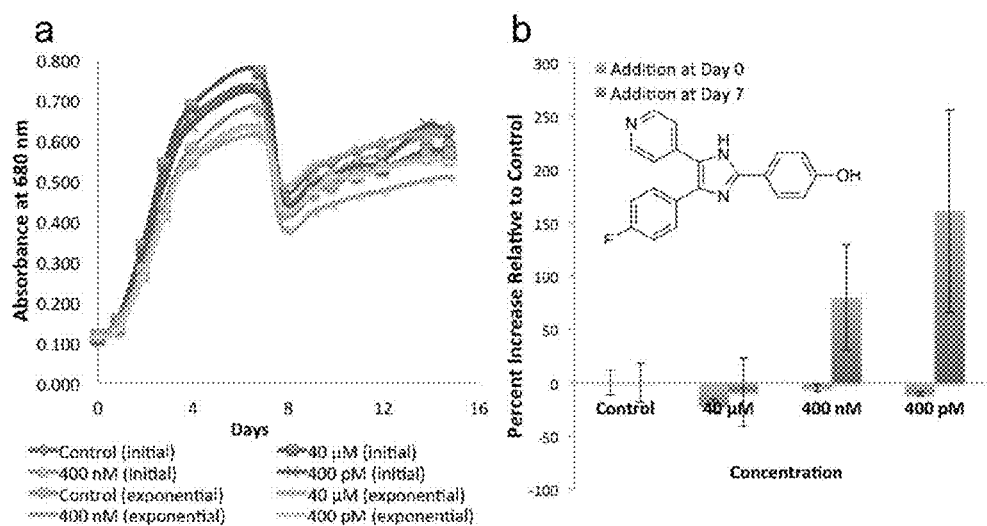
FIG. 13A depicts growth for *P. Tricornutum* in 96-well plates tracked by absorbance and fluorescence with varying concentrations of cycloheximide, with a temporal comparison between addition of compound during the initial (t=0 days) and exponential (t=7 days) phase of growth. Compound wells contain 100 μL media+150 μL algae+cycloheximide diluted in 1 μL of DMSO. Control wells contain 0.4% DMSO.
FIG. 13B depicts percent increase for Nile Red lipid measurement is relative to the DMSO control.

A small molecule screening was performed with a collection of bioactive molecules at two concentrations in four algae strains (FIGS. 2 and 3). The compound collection was screened in all four algae strains at concentrations of 20 μM and 200 nM diluted in DMSO (0.4%). Our preliminary screening collection evaluated 208 commercially available diverse bioactive small molecules with well-characterized activities representing important target classes, such as kinase inhibitors, lipoxygenase inhibitors, fatty acid synthase (FAS) inhibitors, lipase inhibitors, plant hormones, cyclin-dependent kinase (CDK) inhibitors, and antioxidants. Although the development of chemical probes of lipid production is valuable, the majority of compounds selected were non-toxic to enhance long-term commercial potential for use in large-scale algae pond production. FIG. 4 shows a summary of the 200 nM screening data for the four algae strains.

We have observed five outcomes based on growth and lipid phenotypes, depending on both the compound structure and concentration: 1) no effect in growth rate or lipid production; 2) increase both growth rate and lipid levels; 3) decrease both growth rate and lipid levels; 4) decrease growth rate but increase lipid levels; 5) increase growth rate but decrease lipid levels (FIG. 3). The second and fourth outcomes were the focus of this study, although the third outcome is particularly relevant for other research goals related to algae ecology. Based on 800 microplate cultures per species, an average Nile Red standard deviation was calculated to be 40% with a standard error of 20% overall. Based on this error analysis, assay results with a lipid increase >20% percent (regardless of growth rate) were considered to be positive results (i.e., hits) for the assay. A summary of results is provided in FIG. 2 and Table 11. Compounds that showed lipid increases in all four algae strains as well as compounds promoting >40% lipid increase relative to the control were pursued for additional screening. Based on these criteria, 24 compounds were identified from our initial collection as lead compounds to continue investigating for concentration-dependent activity. Table 11 summarizes compounds that result in a 50% or greater effect on intracellular lipid levels using Nile Red analysis Method 2. Only compounds that did not decrease growth effects more than 20% (based on absorbance values) are listed. For *N. oculata*, none of the compounds at 200 nM resulted in an over 50% increase in lipid levels.

TABLE 11

| Algae species | Compound | Absorbance (percent increase) | Nile Red percent increase |
|---|---|---|---|
| *P. tricorntum* | CDK2 I2 (40 μM) | −14.6% | 150.6 |
|  | Ethyl 3,4-dephostatin (40 μM) | −2.4% | 115.0 |
|  | SB202190 (40 μM) | +4.26% | 112.4 |
| *P. tricorntum* | Benzylaminopurine (200 nM) | −14.6% | 105.9 |
|  | Forskolin (200 nM) | −1.2% | 103.6 |
|  | Abscisic acid (200 nM) | −1.2% | 87.0 |
|  | CDKI2 (200 nM) | −7.9% | 50.3 |
| *N. salina* | PTP I2 (20 μM) | +14.0% | 57.6 |
|  | Bohemine (20 μM) | +6.7% | 50.9 |
| *N. salina* | BPDQ (200 nM) | −6.7% | 54.9 |
| *Nannochloris* sp. | EGCG (20 μM) | +1.9% | 92.5 |
|  | Aloisine A (20 μM) | −12.6% | 84.1 |
|  | Arctigenin (20 μM) | −5.4% | 79.0 |
|  | Ethyl palmitate (20 μM) | −8.5% | 65.9 |
|  | Apigenin (20 μM) | −7.3% | 59.9 |
| *Nannochloris* sp. | Cycloheximide (200 nM) | −12.4% | 178.1 |
|  | Bohemine (200 nM) | −12.1% | 150.4 |
|  | Aloisine A (200 nM) | −5.4% | 125.9 |

TABLE 11-continued

| Algae species | Compound | Absorbance (percent increase) | Nile Red percent increase |
|---|---|---|---|
| Nannochloris sp. | Thiamine (200 nM) | −12.1% | 122.6 |
| | Rapamycin (200 nM) | −5.9% | 107.9 |
| | CDKI2 (200 nM) | −14.0% | 103.2 |
| | Cerulenin (200 nM) | −13.2% | 94.6 |
| | EGCG (200 nM) | −1.0% | 92.1 |
| | Erbstatin analog (200 nM) | −7.6% | 90.7 |
| | Jasmonic acid (200 nM) | −7.6% | 87.5 |
| | Atrazane (200 nM) | −1.7% | 86.2 |
| | Kenpaullone (200 nM) | −8.1% | 77.5 |
| | BPDQ (200 nM) | −6.5% | 75.8 |
| | Kinetin (200 nM) | −9.0% | 72.4 |
| | Giberellic acid (200 nM) | −1.1% | 70.4 |
| | Acetaminophen (200 nM) | −6.7% | 68.9 |
| | Arctigenin (200 nM) | −3.4% | 66.0 |
| | Canthardin (200 nM) | −6.5% | 64.5 |
| | Quercetin (200 nM) | −1.6% | 63.5 |
| | Abscisic acid (200 nM) | −2.6% | 61.6 |
| | Forskolin (200 nM) | −5.5% | 60.6 |
| | Caffeine (200 nM) | −7.5% | 60.4 |
| | Citric acid (200 nM) | −6.5% | 55.41 |
| N. oculata | Forskolin (20 µM) | −17.3 | 50.4 |

Additionally, FIGS. 5-8 show results for *P. tricorntum* treated with curcumin, *Nannochloris* sp. treated with genistein, and *P. tricorntum* and *N. oculata* treated with glycerol.

Several classes of molecules were identified as having a consistent effect to increase lipid levels, including molecules known to function as antioxidants, inhibit or activate kinases to promote growth or lipid levels, and inhibit enzymes in lipid metabolism pathways. Several strains of green microalgae respond similarly to certain compounds (e.g., cAMP, forskolin, and quinacrine), suggesting that there are conserved metabolic targets among different strains. However, other compounds (e.g., EGCG, PTP inhibitor II, and cycloheximide) afford varied responses based on the algae strain, which could indicate that regulation of some biological pathways occurs by different mechanisms in different strains. It was generally noted that *Nannochloris* sp. exhibited more positive increases in lipid levels, while *N. oculata* exhibited fewer positive results. Bioactive molecules identified as chemical triggers for increasing lipid levels in *P. tricornutum* were generally distinct from molecules identified for green microalgae strains.

Dose-Response Screening of Lead Compounds in Microplates

Based on the 24 lead compounds selected for their preliminary activity to increase lipid levels in the Nile Red microplate assay, 18 additional compounds were selected with similar biological activity or within the same compound class for further focused screening. This focused collection of compounds was selected based on known functions related to lipoxygenase or lipase inhibition,[27-31] plant hormone activity, protein kinase activation/inhibition, and antioxidant activity.[32-36] These 42 compounds were screened in four algae strains at nine concentrations (ranging from 40 µM to 0.002 nM) to investigate dose-dependent activity and to further characterize the ability of these chemical triggers to increase lipid levels at low compound concentrations. For compounds exhibiting potent activity (growth or lipid increase) at low nM concentrations, additional lower concentration ranges or more narrow ranges were evaluated to determine optimal concentration effects. The purpose of these screening experiments was to identify the most promising compounds and concentrations for testing in larger batch cultures. From these focused screening results, the following conclusions were made: 1) the majority of molecules that afford increases in lipid levels demonstrate activity at nanomolar concentrations; 2) epigallocatechin gallate shows lipid increases at higher concentrations; 3) several different antioxidants show positive lipid increases in algae; 4) an increase in lipid levels frequently correlates with increases in the growth rate and overall cell density relative to the control; 5) some molecules increase the growth rate and overall biomass weight in addition to increasing lipids compared to the control. A summary of lead compound results and concentration effects is provided in Table 11. As a result of this microplate screening, we have identified numerous compounds that increase lipid levels over 100% with optimized concentrations, with some compounds showing activity up to 400%. Table 12 highlights the results for top ranked compounds (with Nile Red percent increase greater than 96%.

TABLE 12

| Algae species | Compound | Concentration | Nile Red percent increase |
|---|---|---|---|
| P. tricorntum | CDK I2 | 40, 10, 2.5 µM | 380, 140, 160 |
| | CDK4 I1 | 40 µM | 129 |
| | Gossypol | 0.0757 nM | 111 |
| | Baicalein | 0.0252 nM | 105 |
| Nannochloris sp. | EGCG | 6, 18.6, 55 nM | 436, 199, 107 |
| | CDK I2 | 40 nM-40 µM | 110-210 |
| | SB202190 | 123-457 pM | 103-175 |
| Nannochloris sp. | Forskolin | 13, 41.2 nM | 121, 118 |
| | cAMP | 4.6-41.2 nM | 105-115 |
| | Quinazoline | 0.00610 µM | 101 |
| N. salina | CDK I2 | 40, 10 µM | 271, 121 |
| | EGCG | 1.48-40 µM | 217-118 |
| | Piceatannol | 40 µM | 195 |
| | CDK4 I4 | 40 µM | 144 |
| | Indomethacin | 55 nM | 118 |
| | Caffeic acid | 0.076-681 nM (H$_2$O) | 96-117 |
| | PTP I2 | 0.681-6.13 nM | 94-113 |
| | Quinacrine | 55 nM | 103 |
| N. oculata | Forskolin | 610 pM-625 nM | 206-110 |
| | Quinacrine | 976 pM-15.6 nM | 161-102 |
| | Cycloheximide | 4.6-41.2 nM | 87-96 |

FIGS. 9-13 show several specific results for compounds epigallocatechin gallate (EGCG), aloisine A, gossypol, PTP Inhibitor II, and cycloheximide.

PTP Inhibitor II is a protein tyrosine phosphatase inhibitor that was selected due to its favorable activity in the 54-compound screen. Due to its potency in cell growth, we chose a lower concentration range of 0.0252-165.6 nM for analysis. FIG. 12 shows the absorbance and percent increases in Nile Red fluorescence for N. salina treated with PTP Inhibitor II. The results show that PTP Inhibitor II significantly increased lipid production at all concentration ranges.

Figure 14:
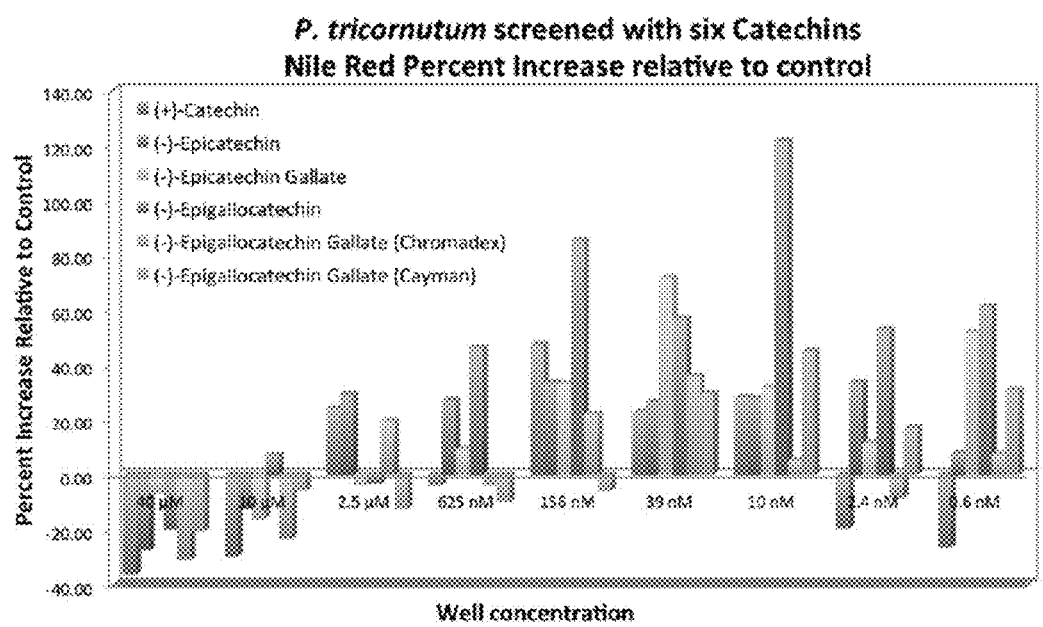
FIG. 14 depicts Nile Red analysis for *P. tricornutum* in microplates with varying concentrations of catechin molecules. Values represent an average of four plate replicates. Algae growth was measured at 680 nm for ~14 days and lipid levels were measured using Nile Red fluorescence at 530 nm on the last day. Compound wells contain 100 μL media+150 μL algae+compound diluted in 1 μL of DMSO. Control wells contain 0.4% DMSO.

It was notable that many compounds showed activity at nanomolar concentrations in multiple algae strains. For example, forskolin, a molecule known to increase intracellular levels of camp, showed activity (lipid increases 100+% greater than the control) in *Nannochloris* sp. and *N. oculata*, and increases near 40% in *N. salina* and *P. tricornutum* (FIG. 14). Furthermore, screening with cAMP also afforded an increase in lipid levels in all four algae strains, with up to 100% in *Nannochloris* sp. Antioxidants such as (−)-epigallocatechin gallate (EGCG) also showed lipid increases of >100% at higher concentrations (>400 nM) in three algae strains (but not *N. oculata*).

The use of DMSO as a compound delivery vehicle was determined to be important for some compounds effects, most notably in the green algae strains, which are known to have thick cell walls. While all preliminary compound screening was performed with DMSO stock solutions (with a final volume of 0.4% per culture), lead compounds were also screened with water as a delivery vehicle to determine if the DMSO was contributing to the observed effects. In the green algae strains, using water as a delivery agent led to minimal effects (<40% increase) of the compounds on the lipid levels, indicating that the DMSO is essential to facilitate the entry of the compound into the cell, or to enhance the effect of the chemical trigger. With the diatom *P. tricornutum*, the use of water instead of DMSO as a delivery agent afforded an increase in the potency of several compounds. For example, SB202190 afforded a 99% increase in lipid levels with water while only a 26% increase was observed with DMSO, at higher concentrations. DMSO was screened at different concentrations to determine the effect on growth (supporting information). DMSO was also independently screened to determine if the vehicle affected algae growth or lipid levels. Minimal effect (within 10% of control growth) was observed at 0.4% v/v DMSO. However, at concentrations of ≥1% v/v DMSO, detrimental growth effects were observed.

Additionally, we investigated temporal effects by adding compounds at different stages of the cell cycle, a chemical genetic option that is not typically available when gene function is disrupted. Comparing compound treatment at various growth phases can also help characterize the target and mechanism of action for a compound. Initial compound screening was performed with compounds added to the microplate wells before the start of the assay (i.e. at t=day 0). A second round of screening was performed where cultures were treated with lead compounds during the exponential phase of growth (t=day 7) to evaluate potential temporal effects. Molecules that demonstrated growth-inhibitory properties when added at t=0 were of particular interest for testing temporal effects because it was envisioned that these compounds could trigger lipid increases without having detrimental growth effects when introduced later in the growth cycle. When the temporal effects for the addition of cycloheximide were investigated, effects on both cell growth and lipid levels were observed. When algae cells were treated with cycloheximide in the initial phase at concentrations <1 µM, an inhibitory effect on cell growth was observed (low absorbance compared to control in all four species) and only minimal increase in lipid levels. However, when cycloheximide was added during the exponential growth phase, an increase in lipid levels (100-200%) was observed over a greater concentration range for *P. tricornutum*. The addition of SB202190 in exponential growth phase (Day 7) was also investigated, and these conditions also afford a greater increase in lipid levels in *N. oculata* (doubling the lipid levels from 45% to 95% at lower concentrations).

Lipoxygenase Inhibitors

We also tested a focused collection of lipoxygenase inhibitors, comparing both DMSO and water delivery for increase of lipid production with *N. oculata, N. salina*, and *P. tricornutum*. These lipoxygenase inhibitory compounds included curcumin, esculetin, baicalein, caffeic acid, and gossypol. Due to potent effects in the first round of screening, the lipoxygenase compound screen was repeated at lower concentrations, down to 0.025 nM. The algal strains *N. salina* and *P. tricornutum* showed the best response in lipid production with lipoxygenase inhibitors compared to other algal strains. Results for *N. salina* indicated that caffeic acid had optimal effective concentration in the range of 0.22-0.68 nM, while gossypol had an optimal effective concentration of 6 nM. The microplate analysis of these compounds showed that caffeic acid, diluted in water, increased lipid production more than 100%, while <20% lipid increase was observed with DMSO. Similar to epigallocatechin gallate, caffeic acid is a highly polar, water-soluble compound and this may account for the stronger effects in water compared to DMSO. Although caffeic acid diluted in water did not increase lipid production in *N. salina*, compounds such as gossypol had the inverse effect, which indicates that in some cases DMSO helps in compound delivery to the cell. Since not all compounds are soluble in water, the stock solution in DMSO was further diluted with water to ensure compound availability. These results indicate that water may not always be a better alternative. Furthermore, the results showed that lipoxygenase inhibitors interact differently in different algal types and strains. Gossypol in DMSO was also shown to increase lipid in the diatom *P. tricornutum*, while no increase in lipids were observed in other green algal strain such as *N. oculata*. Results for *P. tricornutum* with DMSO delivery indicated that caffeic acid had a minimal effect on lipid production, while gossypol had an optimal effective concentration of 0.0757 nM with >250% increase in lipid production. Table 13 summarizes the results with lipoxygenase inhibitors.

TABLE 13

| Compound | Inhibitor | Concentration Range | Algae Species | % increase |
|---|---|---|---|---|
| Curcumin | LOX | 18 nM-13 µM | N. salina | 18-69 |
|  |  | 0.0252 nM-0.227 nM |  | 5-9 (H$_2$O) |
|  |  | (H2O) |  |  |
| Caffeic Acid | LOX | 0.0252 nM-165.6 nM | N. salina | 1-40 |
|  |  | 0.0252-0.681 nM (H2O) |  | 62-110 (H$_2$O) |
| Baicalein | LOX | 0.0252-55.2 nM | N. salina | 3-28 |
|  |  | 0.0252-165.6 nM (H2O) |  | 6-30 (H$_2$O) |

TABLE 13-continued

| Compound | Inhibitor | Concentration Range | Algae Species | % increase |
|---|---|---|---|---|
| Esculetin | LOX | 0.0757-55.2 nM | N. salina | 1-30 |
| | | 0.0252-6.13 nM (H2O) | | 5-31 (H$_2$O) |
| Gossypol | LOX | 0.0757-55.2 nM | N. salina | 8-81 |
| | | 0.0757-6.13 nM (H2O) | | 1-27(H$_2$O) |
| Curcumin | LOX | 6-494 nM | P. tricornutum | 7-30 |
| Caffeic Acid | LOX | 6-165 nM | P. tricornutum | 13-205 |
| Baicalein | LOX | 0.0252-55.2 nM | P. tricornutum | 5-94 |
| Esculetin | LOX | 0.0252-18.4 nM | P. tricornutum | 3-79 |
| Gossypol | LOX | 0.0252-165.6 nM | P. tricornutum | 5-283 |
| Curcumin | LOX | 0.0252-0.0757 nM | N. oculata | 4-10 |
| Caffeic Acid | LOX | 0.681 nM | N. oculata | 5 |
| Baicalein | LOX | 0.0252 nM | N. oculata | 25 |

Protein Tyrosine Kinase Inhibitors

We also tested a collection of protein tyrosine kinase inhibitors for increase of lipid production with *N. salina*, and *P. tricornutum*. These protein tyrosine kinase inhibitory compounds included BPDQ, genistein, butein, emodin, piceatannol, and quinazoline. The results are summarized in Table 14.

TABLE 14

| Compound | Inhibitor | Concentration Range | Algae Species | % increase |
|---|---|---|---|---|
| BPDQ | PTK | 6.1 nM-4.44 µM | N. salina | 30-120 |
| Genistein | PTK | 6.1 nM-40 µM | N. salina | 11-85 |
| Butein | PTK | 0.494 µM-40 µM | N. salina | 2-29 |
| Emodin | PTK | 6.1 nM-13.3 µM | N. salina | 7-62 |
| Piceatannol | PTK | 55-40 µM | N. salina | 0.3-148 |
| Quinazoline | PTK | 6.1 nM-40 µM (none) | N. salina | |
| BPDQ | PTK | 1.4-4.4 µM (H$_2$O) | P. tricornutum | 5-53 |
| Genistein | PTK | 54 nM-40 µM (H$_2$O) | P. tricornutum | 16-70 |

TABLE 14-continued

| Compound | Inhibitor | Concentration Range | Algae Species | % increase |
|---|---|---|---|---|
| Butein | PTK | 40 µM | P. tricornutum | 14 |
| | | 54 nM-40 µM (H$_2$O) | | 1-116 (H$_2$O) |
| Emodin | PTK | 0.49-13.3 µM (H$_2$O) | P. tricornutum | 1-30 (H$_2$O) |
| Piceatannol | PTK | 4-40 µM (H$_2$O) | P. tricornutum | 7-41 (H$_2$O) |
| Quinazoline | PTK | 4-40 µM (H$_2$O) | P. tricornutum | 15-26 (H$_2$O) |

Protein Tyrosine Phosphatase Inhibitors

We also tested a collection of protein tyrosine phosphatase inhibitors for increase of lipid production with *N. salina, P. tricornutum*, and *N. oculata*. These protein tyrosine phosphatase inhibitory compounds included PTP Inhibitor II, ethyl 3,4-dephostatin, cantharidin, napthyl acid phosphate, dephostatin, and 3,4-dephostatin. The results are summarized in Table 15.

TABLE 15

| Compound | Inhibitor | Concentration Range | Algae Species | % increase |
|---|---|---|---|---|
| PTP Inhibitor II | PTP | 0.025 nM-165 nM | N. salina | 4-118 |
| | | 0.025-2 nM (H$_2$O) | | 0.4-50 (H$_2$O) |
| Ethyl 3,4-dephostatin | PTP | 0.0252-165.6 nM (both) | N. salina | 8-20 |
| | | | | 8-61 (H$_2$O) |
| Cantharidin | PTP | 0.0252-0.681 nM | N. salina | 1-15 |
| | | 0.0252-165 nM (H$_2$O) | | 7-87 (H$_2$O) |
| Napthyl acid phosphate | PTP | 0.0252-18.4 nM | N. salina | 1-51 |
| | | 0.0252-165.6 nM (H$_2$O) | | 15-61 (H$_2$O) |
| Dephostatin | PTP | 0.0252-165.6 nM (both) | N. salina | 0.1-40 |
| | | | | 7-94 (H$_2$O) |
| 3,4-dephostatin | PTP | 0.0252-55.2 nM | N. salina | 8-40 |
| | | 0.0252-165.6 nM (H$_2$O) | | 14-72 (H$_2$O) |
| PTP Inhibitor II | PTP | 6.13-55.2 nM (H$_2$O) | P. tricornutum | N/A |
| Ethyl 3,4-dephostatin | PTP | 2-18.4 nM | P. tricornutum | 3-67 |
| | | 0.0252-165.6 nM (H$_2$O) | | 8-106 (H$_2$O) |
| Cantharidin | PTP | 0.0252-0.0757 nM | P. tricornutum | 9-35 |
| | | 0.0252-165.6 nM | | 0.17-168.19 (H$_2$O) |
| Napthyl acid phosphate | PTP | 18.4 nM | P. tricornutum | 4 |
| | | 0.0252-165.6 nM | | 1-60 (H$_2$O) |
| Dephostatin | PTP | 0.0252-165.6 nM | P. tricornutum | 0.6-44 |
| | | 165.6 nM (H$_2$O) | | 24 (H$_2$O) |
| 3,4-dephostatin | PTP | 0.0252-165.6 (both) | P. tricornutum | 12-33 |
| | | | | 5-46 (H$_2$O) |
| PTP Inhibitor II | PTP | 0.0252-165.6 (none) | N. oculata | N/A |
| Ethyl 3,4-dephostatin | PTP | 0.0252-165.6 (none) | N. oculata | N/A |
| Cantharidin | PTP | 55.2-165.6 nM | N. oculata | 11-54 |
| Napthyl acid phosphate | PTP | 165.5 nM | N. oculata | 18 |

TABLE 15-continued

| Compound | Inhibitor | Concentration Range | Algae Species | % increase |
|---|---|---|---|---|
| Dephostatin | PTP | 0.0252-165.6 (none) | N. oculata | N/A |
| 3,4-dephostatin | PTP | 0.07-2.04 nM ($H_2O$) | N. oculata | 6-76 ($H_2O$) |

Lipase Inhibitors

We also tested a collection of lipase inhibitors for increase of lipid production with N. salina, P. tricornutum, and N. oculata. These lipase inhibitory compounds included Rhc80267, orlistat, JZL 184 hydrate, halopemide, PTFK, and ET-18-OCH3. The results are summarized in Table 16.

TABLE 16

| Compound | Inhibitor | Algae species | Conc. | % change in abs | % in NR fl |
|---|---|---|---|---|---|
| RHC 80267 | Diacylglycerol lipase inhibitor | P. tricornutum | 4.6 nM | −6.46 | 45.19 |
| RHC 80267 | Diacylglycerol lipase inhibitor | N. salina | 40 μM | −42.09 | 71.52 |
| RHC 80267 | Diacylglycerol lipase inhibitor | N. salina | 3.3 μM | −14.83 | 68.33 |
| RHC 80267 | Diacylglycerol lipase inhibitor | N. oculata | 4.6 nM | 12.83 | 49.41 |
| Orlistat | Lipase inhibitor | N. salina | 40 μM | −31.92 | 61.76 |
| Orlistat | Lipase inhibitor | N. oculata | 13 nM | 0.83 | 63.67 |
| JZL 184 hydrate | Monoacylglycerol lipase inhibitor | P. tricornutum | 4.6 nM | −2.26 | 58.66 |
| JZL 184 hydrate | Monoacylglycerol lipase inhibitor | N. salina | 40 μM | 0.61 | 118.99 |
| JZL 184 hydrate | Monoacylglycerol lipase inhibitor | N. salina | 3.3 μM | −12.15 | 95.70 |
| JZL 184 hydrate | Monoacylglycerol lipase inhibitor | N. salina | 10 μM | 13.75 | 86.72 |
| Halopemide | Phospholipase inhibitor | P. tricornutum | 4.6 nM | 8.83 | 128.13 |
| PTFK | Phospholipase inhibitor | P. tricornutum | 4.6 nM | 9.75 | 79.36 |
| Halopemide | Phospholipase inhibitor | P. tricornutum | 10 μM | −31.22 | 73.94 |
| PTFK | Phospholipase inhibitor | P. tricornutum | 13 nM | 3.22 | 70.44 |
| PTFK | Phospholipase inhibitor | P. tricornutum | 41.2 nM | 5.05 | 67.59 |
| ET-18-OCH3 | Phospholipase inhibitor | N. oculata | 4.6 nM | −18.13 | 79.34 |
| ET-18-OCH3 | Phospholipase inhibitor | N. oculata | 40 μM | −5.90 | 57.25 |
| Halopemide | Phospholipase inhibitor | N. oculata | 40 μM | −2.02 | 55.13 |
| ET-18-OCH3 | Phospholipase inhibitor | N. oculata | 10 μM | 5.73 | 50.05 |

Further Compounds

We also tested a collection with more antioxidants, kinase inhibitors, and further compounds for increase of lipid production with N. salina, P. tricornutum, N. oculata, and Nannochloropsis sp. The results are summarized in Table 17.

TABLE 17

| Compound | Target | Algae Species | Best Conc. | % Inc |
|---|---|---|---|---|
| BHA | Antioxidant, Food Preservative | N. salina | 10 nM | 290.14 |
| Resveratrol | Antioxidant, Anticancer, anti-inflammatory | N. salina | 10 nM | 272.72 |
| Propyl Gallate | Antioxidant, Food Additive | N. salina | 10 nM | 264.42 |
| (−)-Epigallocatechin | Antioxidant, Cannabinoid Receptor Agonist | N. salina | 39 nM | 216.15 |
| CDK2 I2 | Cyclin Dependent Kinase 2 | P. tricornutum | 2.5 μM | 163.88 |
| (−)-Epicatechin | MAO-B inhibitor, Stroke Brain Protection Factor | N. salina | 2.4 nM | 147.90 |

TABLE 17-continued

| Compound | Target | Algae Species | Best Conc. | % Inc |
|---|---|---|---|---|
| CDK4 I4 | Cyclin Dependent Kinase 4 | N. salina | 40 μM | 144.22 |
| Benzylamino Purine | Plant Respiratory Kinase | P. tricornutum | 40 μM | 120.94 |
| CDK4 I3 | Cyclin Dependent Kinase 4 | N. salina | 39 nM | 116.30 |
| CDK4/6 I4 | Cyclin Dependent Kinases 4/6 | N. salina | 2.4 nM | 115.84 |
| Apigenin | Benzodiazepine Ligand, Plant Hormone, CYP2C9 inhibitor, Reverses Cyclosporin Damage | N. salina | 39 nM | 90.17 |
| (+)-Catechin | Histidine Decarboxylase Inhibitor, MAO-B inhibitor, Antioxidant | N. salina | 39 nM | 84.21 |
| (−)-Epicatechin Gallate | Antioxidant | P. tricornutum | 156 nM | 77.89 |
| Kinetin | Plant Hormone that Promotes Cell Division | P. tricornutum | 39 nM | 76.29 |
| CDK4 I1 | Cyclin Dependent Kinase 4 | P. tricornutum | 10 μM | 68.76 |
| Naproxen | NSAID | N. salina | 156 nM | 67.44 |
| Quercitin | Polar Auxin Transport Inhibitor, Anti-inflammatory, MAO Inhibitor | N. oculata | 2.5 μM | 67.10 |
| Ascorbic Acid | Antioxidant, Vitamin, Dietary Micronutrient | P. tricornutum | 10 nM | 57.28 |
| Melatonin | Hormone, Antioxidant | P. tricornutum | 40 μM | 47.80 |
| (−)-Epigallocatechin Gallate | Antioxidant | P. tricornutum | 10 nM | 45.03 |
| N,N'-di-sec-butyl-p-phenylenediamine | Antioxidant, | P. tricornutum | 156 nM | 39.51 |
| Tocopherol | Antioxidant, Vitamin | Nannochloropsis sp. | 2.4 nM | 31.44 |
| Acetaminophen | Analgesic | Nannochloropsis sp. | 2.4 nM | 13.11 |

Error Analysis

Error analysis was performed based on replicates for absorbance (cell density) and Nile Red fluorescence measurements relative to the control, with all measurements in clear microplates. Nile Red analysis was performed on the third day of stationary phase with fluorescence readings performed from the top position. Assays were repeated in triplicate, and both absorbance and Nile Red fluorescence measurements were compared to control wells, including both in-plate and external controls (a minimum of 78 controls per screen). Two analysis methods were compared for Nile Red fluorescence measurements that differ based on whether the maximum fluorescence intensity is selected before or after averaging the replicates. In the first method, all Nile Red fluorescence intensities are averaged from the three replicate plates, and then the maximum fluorescence is taken from the averaged values. These are then compared to the control to approximate the percent increase in lipids per well. The minimum number of replicates per compound concentration is three, and the minimum number of control wells is 18. In a second method, the maximum Nile Red fluorescence intensity is selected for each well, and then an average is obtained based on three replicate wells. For the second method, the maximum fluorescence intensity with P. tricornutum is selected starting after four minutes to allow sufficient time for the dye to enter the cells.

Nile Red error analysis for the microplate data showed an error of approximately 20%. The standard deviation was greater than 30% in all species, with a percent error of around ~20% for all species. These results are all based on over 800 data points per species, and each data point is an average of the maximum of three or more replicates. The minimum number of controls for all data analyzed was 18. Sources of error for Nile Red analysis are attributed to the variation in the amount of time from dye addition to plate reader analysis, and the slight variations in dye concentration due to solvent evaporation or different dye batches.

Batch Culture Screening Results

Based on microplate screening and dose response, 36 candidate compounds were selected for screening in 500 mL batch cultures to confirm activity of the compounds on larger scale and to perform secondary assays to analyze lipid composition. Selection was based on increases in lipid levels that were over 50% to 100% based on Nile Red fluorescence relative to control, consistency in screening results, and/or if positive results occurred in more than one species. Batch cultures were also repeated in triplicate and compared to a control culture grown at the same time. Algae were harvested and lipids were extracted for gravimetric analysis.

Figure 19:
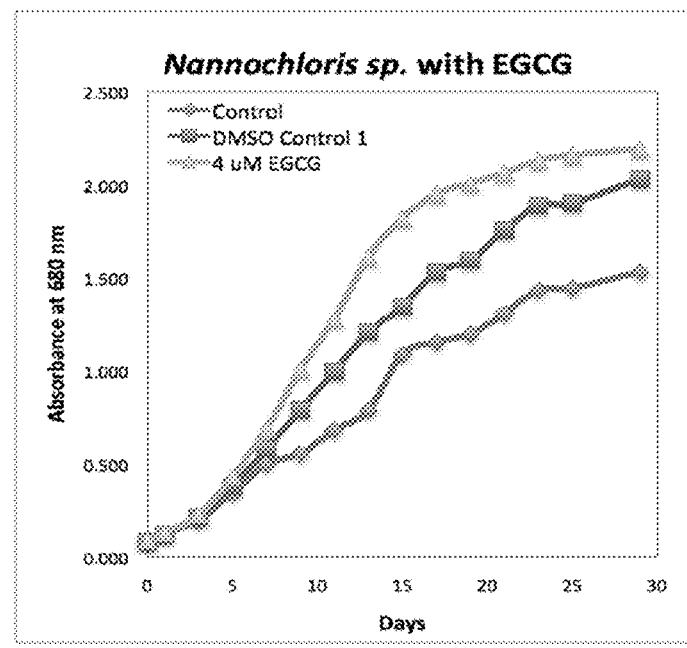
FIG. 19 depicts results for 500 mL cultures of media and algae, comparing DMSO and EGCG added in 2 mL of DMSO. The air bubbling and stirring for all cultures was started at day 0. The control is without the addition of DMSO. Cultures were harvested 6 days into stationary phase.

Epigallocatechin gallate (EGCG), the most abundant catechin found in green tea, resulted in a consistent increase of >40% lipids by dry weight (FIG. 19). In batch cultures, we observed that EGCG regularly increased growth and lipid levels in N. salina and Nannochloris sp. relative to control (Table 18 and FIG. 19). When combined with sodium bicarbonate addition, EGCG increases lipid levels in N. oculata significantly. Various biological effects have been reported for EGCG, ranging from the inhibition of fatty acid synthase to the inhibition of MAP kinase mediated signaling pathways.[37,38] Furthermore, the antioxidant action of EGCG can protect cells from lipid peroxidation,[39] which would enhance photosynthetic efficiency.

Table 18 shows a comparison of dry weight and lipid levels for 500 mL algae cultures treated with EGCG vs. control cultures with and without DMSO. Cultures were harvested at day 6 in stationary phase. Cultures were pelleted, lyophilized, and extracted side-by-side. The experiment was performed in triplicate.

TABLE 18

| N. salina | Control | DMSO Control (0.4% by volume) | 40 μM EGCG |
|---|---|---|---|
| Absorbance at harvest | 1.19 ± 0.15 | 1.50 ± 0.13 | 1.41 ± 0.08 |
| Number of Cells | 1.73E+09 ± 1.45E+08 | 1.44E+09 ± 0.28E+08 | 1.36E+09 ± 7.27E+07 |
| Dry Weight (mg) | 236.93 ± 54.99 | 429.90 ± 109.74 | 337.40 ± 62.55 |
| Recovered Weight (mg) | 233.70 ± 23.48 | 393.17 ± 112.84 | 330.03 ± 78.14 |
| Extract Weight (mg) | 60.78 ± 13.94 | 92.83 ± 6.37 | 94.77 ± 9.47 |

During batch culture screening, it was noted that lipid levels increased upon treatment of microalgae with DMSO, an effect that was more pronounced in certain strains. Upon comparison of control experiments with DMSO, we observed that DMSO at 0.4% afforded increased growth and lipid levels with N. oculata and N. salina (Tables 19 and 20). No significant changes were observed with P. tricornutum and Nannochloris sp. DMSO in this quantity did not show a toxic or detrimental effect on the growth rate. In a microplate screen with N. oculata, the addition of 0.4% DMSO increased cell density by 57% and lipid levels by 75%. While 0.4% DMSO had relatively minimal effects in batch cultures, the addition of 1.0% DMSO also increased lipid levels by 78% relative to control without DMSO. Upon analysis of the lipid extracts, it was determined that the overall lipid profile remained consistent when DMSO was added. The addition of DMSO also afforded increased growth and lipid levels in other green algae strains, with lipid levels in N. salina increasing up to 50% in batch culture (Table 18). However, in P. tricornutum, DMSO showed a decrease in growth and lipid production compared to the control. DMSO is known to be a versatile molecule with diverse applications as a solvent, delivery vehicle for organic molecules,[40] cryoprotectant,[41] and antioxidant.[42] In a previous study by De La Vega and co-workers, the addition of 1.0% DMSO has been shown to enhance lipid synthesis and secretion with increased levels of cellular triglycerides, phospholipids, and cholesterol observed in rat hepatocytes.[43] DMSO is naturally occurring in algae[44] and originates from the enzymatic cleavage product of DMSP, DMS. In algae species such as *Thalassiosira pseudonana*, DMSP serves as an antioxidant and cryoprotectant.[45] Without wishing to be bound by theory, it is also believed that DMSO promotes the permeation of solutes.[47] Table 19 shows 500 mL cultures were harvested on day 6 of stationary phase. Cultures were pelleted, lyophilized, and extracted side-by-side.

TABLE 20

| N. oculata | Average | DMSO Average | 4 nM Forskolin | 40 nM cAMP |
|---|---|---|---|---|
| Absorbance at harvest | 1.92 ± 0.14 | 1.83 ± 0.20 | 2.10 ± 0.18 | 2.04 ± 0.16 |
| Number of Cells | 2.43E+09 ± 1.82E+08 | 2.32E+09 ± 2.58E+08 | 2.46E+09 ± 5.42E+08 | 2.58E+09 ± 1.97E+08 |
| Dry Weight (mg) | 307.93 ± 90.87 | 283.27 ± 62.40 | 353.57 ± 79.09 | 253.32 ± 259.41 |
| Recovered Weight (mg) | 290.93 ± 90.28 | 267.27 ± 50.80 | 344.90 ± 76.75 | 377.90 ± 1.24.32 |
| Extract Weight (mg) | 41.20 ± 8.77 | 56.83 ± 18.42 | 88.67 ± 23.8 | 57.30 ± 19.37 |

Chemical Genetic Assay Results with antioxidants

Figure 15:
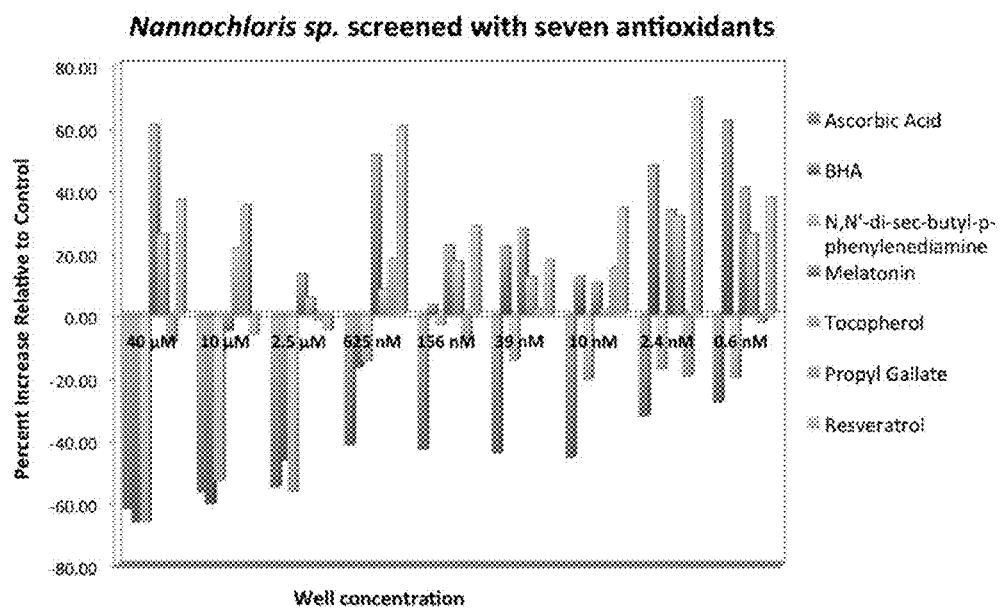
FIG. 15 depicts Nile Red analysis and comparison of varying concentrations antioxidants for *Nannochloris* sp. in microplates. Values represent an average of four plate replicates. Algae growth was measured at 680 nm for ~21 days and lipid levels were measured using Nile Red fluorescence at 530 nm on the last day. Compound wells contain 100 μL media+150 μL algae+compound diluted in 1 μL of DMSO. Control wells contain 0.4% DMSO.

Based on the positive results with epigallocatechin gallate, we screened the effects of additional members of the catechin class of molecules. The molecules included (+)-catechin, (−)-epicatechin, (−)-epicatechin gallate, (−)-epigallocatechin, and catechin mixtures isolated from green tea extract. These molecules were screened in a microplate assay with the four standard algae strains N. salina, N. oculata, P. tricornutum, and Nannochloris sp. The results showed that lipid production increased in all species treated with (−)-epicatechin, (−)-epigallocatechin gallate, and (−)-epicatechin gallate. Different species responded either adversely or positively to (+)-catechin dosing, and a reduction in lipids was found in all species treated with (−)-epigallocatechin. Exemplary results for P. tricornutum are shown in FIG. 15. The highest lipid increase in P. tricornutum was seen with (−)-epicatechin gallate at 39-56 nM concentration (FIG. 14).

Related to the potential mechanism of action of epigallocatechin gallate (and other members of this compound family) as an antioxidant, we also screened several common commercial/industrial antioxidants used in food and fuel preservation (FIG. 15). These antioxidants include ascorbic

TABLE 19

| N. oculata | Control | DMSO (0.4%) | DMSO (1%) | NaHCO₃ (0.6 g/L) | DMSO (0.4%) + NaHCO₃ (0.6 g/L) | DMSO (1%) + NaHCO₃ (0.6 g/L) | 400 nM EGCG | DMSO (0.4%) + EGCG (400 nM) + NaHCO₃ (0.6 g/L) |
|---|---|---|---|---|---|---|---|---|
| n | 5 | 3 | 2 | 3 | 2 | 1 | 4 | 3 |
| Absorbance at harvest | 1.900 ± 0.106 | 1.776 ± 0.060 | 1.827 ± 0.288 | 2.373 ± 0.217 | 2.021 ± 0.045 | 2.286 | 1.855 ± 0.142 | 2.149 ± 0.444 |
| Dry weight | 349.5 ± 139.7 | 409.2 ± 105.6 | 280.4 ± 88.0 | 371 ± 117.8 | 894.6 ± 609.2 | 380.9 | 290.7 ± 34.5 | 379.3 ± 70.4 |
| Extract Weight | 48.2 ± 11.9 | 67.2 ± 7.8 | 47.2 ± 11.0 | 93.5 ± 34.0 | 69.8 ± 30.7 | 30.7 | 62.3 ± 21.6 | 63.4 ± 13.3 |

Forskolin is another small molecule that was shown to increase growth and lipid production in algae. Forskolin is a natural product, known to stimulate adenylate cyclase activity and activate protein kinase A. After confirming forskolin's positive results in the initial screening, both forskolin and cAMP were tested in parallel in dose-response microplate screen; positive growth and lipid increases were observed. In batch cultures, forskolin induced increases in lipid production in N. oculata (Table 19) as well as Nannochloris sp. and N. salina. cAMP also increased lipid levels, but not to the same extent as forskolin. It was particularly notable that cAMP can affect saturation levels across several species. Table 20 shows 500 mL cultures were harvested on day 6 of stationary phase. Cultures were pelleted, lyophilized, and extracted side-by-side (n=3).

acid, BHA, tocopherol, melatonin, N,N'-di-sec-butyl-p-phenylenediamine, resveratrol, and propyl gallate. These molecules were tested in N. salina, N. oculata, P. tricornutum, and Nannochloris sp. to determine if the effect observed for (−)-epigallocatechin gallate is based on its mechanism as an antioxidant. Of the antioxidants screened, the three compounds that demonstrated the most consistent lipid increase were propyl gallate, resveratrol, and BHA, which showed consistent effects in various algae.

Figure 17:
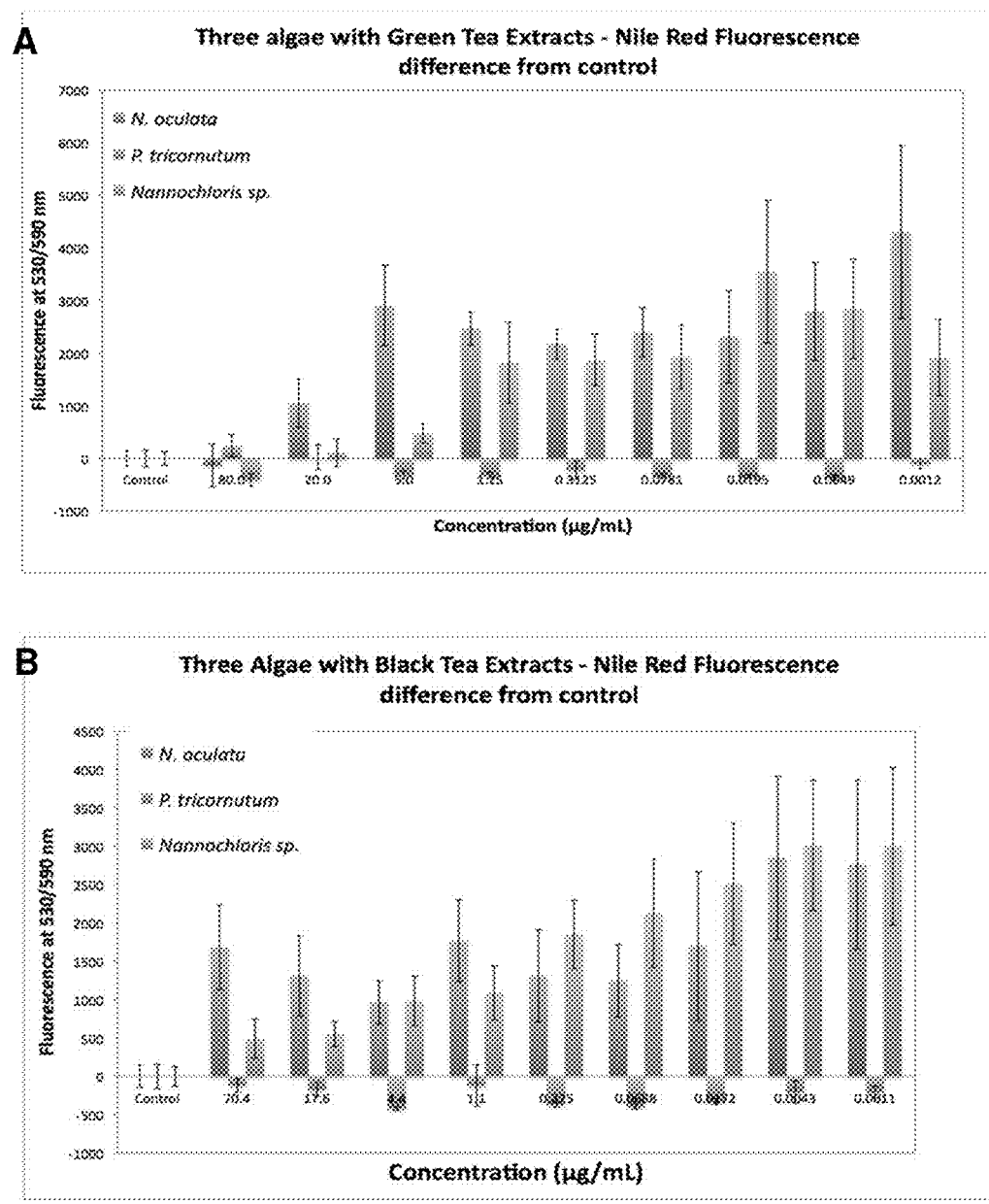
FIGS. 17A and 17B depict Nile Red analysis and comparison of varying concentrations of tea antioxidant extract in microplates.

Crude extracts of antioxidants from green tea and black tea, green tea, and grape pomace were also screened using the microplate assay to test multiple concentrations (FIG. 17). Using isopropyl alcohol extracts, these crude extracts of antioxidants were screened in N. salina, N. oculata, P. tricornutum, and Nannochloris sp. These extracts displayed varying effects on lipid production. While a decrease in lipid levels was observed with grape pomace at all concentrations, black green and black tea extracts provided an increase in lipid levels of over 100% (FIG. 17, final concentrations based on diluted stock in culture). Green tea and black tea showed increases in lipid content in *N. oculata* and *Nannochloris* sp.; however the addition of these extracts did not result in an increase in lipid production in *P. tricornutum* or *N. salina*. This is a specific effect based on the algae strain.

Figure 16:
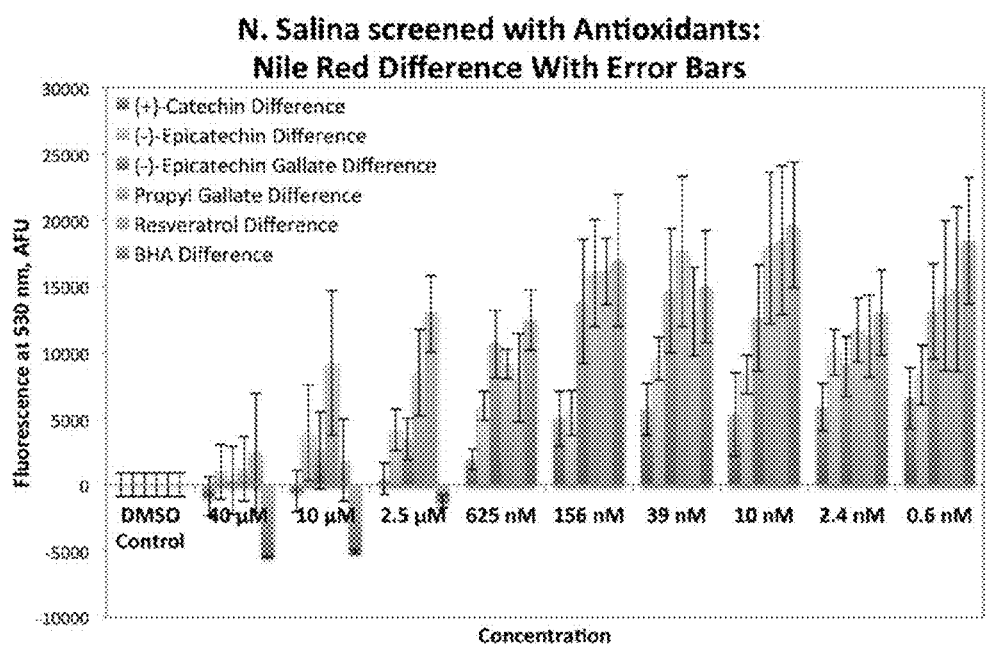
FIG. 16 depicts *N. salina* microplate results for the screening of antioxidants in microplates. Fluorescence results are the difference from the control. Lower concentrations seem to have a more positive effect on lipid production, with the best range between 156 nM and 10 nM. Screen is performed with four replicates. Compound wells contain 100 μL media+150 μL algae+compound diluted in 1 μL of DMSO. Control wells contain 0.4% DMSO.

The compounds (+)-catechin, (−)-epicatechin, (−)-epicatechin gallate, propyl gallate, resveratrol, and butylated hydroxyanisole (BHA) were screened at concentrations from 0.6 nM to 40 µM in *Nannochloropsis* sp. and *N. salina*. The antioxidants compounds all showed consistently positive results in *N. salina* at several lower concentrations (FIG. 16).

Example 2

The following Example relates to the chemical triggers that alter lipid composition in microalgae.

Materials and Methods

Lipid Extraction and Sample Preparation

The nonpolar algal extracts were harvested from 500 mL cultures when indicated on growth curves, a minimum of 3 days into stationary phase. Cells were pelleted by centrifugation at 6000×g at 0° C. for 20 minutes (Thermo Scientific RC-6 Plus, rotor SLA-3000, Waltham, Mass., USA), washed with Millipore water, re-pelleted and then lyophilized (Labconco Freezone 6, Kansas City, Mo.) to dryness (1-2 days). Cells were crushed and nonpolar lipids were extracted by sonication (Fisher Scientific Model 120 Sonic Dismembrator, ThermoFisher, San Jose) for 1 minute in chloroform, followed by chloroform-methanol extractions, washed with PBS butter, and dried under vacuum.[55-60] The crude nonpolar algae extracts were then analyzed by $^1$H Nuclear Magnetic Resonance ($^1$H NMR) for verification of TAG presence and examination of the purity of the extract (determination of level of chlorophyll). The extracts were then divided for analysis; one part for transesterification, one part to save as crude extract, and one part for SPE separation and MALDI-TOF analysis of TAGs.

Triacylglycerols can be isolated by solid-phase extraction (SPE) with 500 mg silica SPE cartridges (Silicycle, Quebec). The nonpolar extract is dissolved in 300 µL hexanes, and loaded on the SPE cartridge primed with hexanes. A mixture of 80:20:1 hexanes/diethyl ether/acetic acid was used as mobile phase to elute the TAGs.[61] SPE removes any chlorophyll in this process. Residual polar fraction containing polar lipids and chlorophyll was obtained by elution with acetone. All extracts and TAG fractions were dried under vacuum and stored under argon in amber vials at −20° C. before spectroscopic analysis. After SPE, the purified TAG fraction was reanalyzed with $^1$H NMR spectroscopy for TAG characterization.

MALDI-MS Analysis of Algal Lipid Extracts

All MALDI-TOF spectra were acquired on the 4700 MALDI-TOF-TOF (Applied Biosystems, Foster City, Calif.) with internal MALDI source, a 355-nm pulsed Nd:YAG laser, and was operated in positive ionization mode for analysis. The TOF was in Reflectron mode with laser intensity from 5500-6500 Volts. Each acquisition consisted of 2500 shots with a focus mass of 900 Da, and a scan range of m/z 400-1100. Multiple acquisition scans were performed at different laser intensities to determine optimal conditions. Samples for the MALDI-TOF were diluted to 5 mg/mL in hexane, and spotted in the fast-evaporation method in a 1:2 ratio with DHB (2,5-dihydroxybenzoic acid) as the matrix. Re-spotting with methanol allowed for the matrix and sample to mix without hexane interactions, and allowed for better crystal formation. All samples on MALDI plate were allowed to dry before MS analysis. Data was normalized to base peak in all cases.

ESI-MS Analysis of Lipid Extracts

The ESI-LTQ-Orbitrap (ThermoFisher, San Jose, Calif.) was used for direct-inject electrospray analysis of the algal extracts. Samples for the LTQ-Orbitrap were diluted to 2 mg/mL extracts in hexanes, and then diluted to 2 µM in acetone. Salt solutions of lithium and sodium acetate (100 mM starting concentration) were doped into the acetone solution to a concentration of 20 µM prior to injection. The ESI-LTQ-Orbitrap was operated in positive electrospray ionization mode with an electrospray voltage of 5 kV. The sample was direct injected, and sprayed into the mass spectrometer with the sheath, auxiliary and sweep gas set at 8, 0, and 0 units, respectively, and desolvation was further aided by an ion transfer tube temperature of 250° C. An isolation width of 2 amu was used with either 30% or 35% normalized collision energy (CID) for $MS_n$ experiments. All scan events were detected in the FT detector to give accurate mass data. The methods were verified using positive controls, such as triolein [Sigma Aldrich, St. Louis] and commercial oils (olive oil, ACROS Organics, New Jersey).

Transesterification of TAGs to Fatty Acid Methyl Esters (FAMEs) and GCMS

After the initial weight was recorded, the nonpolar extract set aside for transesterification was dissolved in 3.0 mL of 0.6 M sulfuric acid in methanol and stirred vigorously at 60° C. for 45 minutes. After cooling to room temperature, the reaction was neutralized (saturated aqueous sodium bicarbonate), extracted (hexanes), and the organic layer was isolated and concentrated in vacuo, yielding FAMEs and unreacted lipids. The aqueous layer was discarded. Reaction completion was determined by $^1$H NMR spectroscopy by the presence of methyl ester proton signal at 3.67 ppm.

The sample was concentrated and reconstituted in methanol for Gas Chromatography Mass Spectrometry (GC/MS) analysis to a final concentration of 2.5 mg/mL. 5 µL of sample was injected via split-less injection. Initial GC/MS temperature was 50° C. and end was 200° C. over at a one hour period for optimal FAME peak separation.

$^1$H NMR Spectroscopy of Algal Lipid Extracts

For crude and purified NMR spectroscopy analysis, the dried lipid extract was dissolved in 650 µL of deuterated chloroform (CDCl$_3$) with the addition of ~5 mg of 3,4,5-trichloropyridine (AlfaAzar, Ward Hill, Mass.) as an internal standard, and then transferred to a 5 mm NMR tube. $^1$H NMR spectra were acquired at 283 K on a 300, 400 or 600 MHz NMR spectrometer (Varian, Palo Alto, Calif.) with a relaxation delay of 1 s, pulse angle of 45 degrees, and line broadening of 0.2 Hz. Samples were referenced to tetramethylsilane at 0 ppm and 3,4,5-trichloropyridine at 8.53 ppm (singlet). Figures were processed using MestReNova software. Peak assignment of fatty acids and their derivatives are based on NMR spectroscopic studies of previously reported algal lipid extracts[9] and comparison to standards such as olive oil (ACROS) and fatty acid mixtures.

Results

We developed a quick and robust method to screen if the screened compound effect fatty acid saturation levels using $^1$H NMR spectroscopy. The amount of saturated fatty acids (SFA), monounsaturated fatty acids (MUFAs), and polyunsaturated fatty acids (PUFAs) was determined using peak area ratios. Table 21 displays the variation in microalgae along with a comparison to two yeast strains. While yeast and algae contain similar levels of SFA, yeast contain distinctively higher levels of MUFAs whereas microalgae contain higher levels of PUFAs.

TABLE 21

| n | Name | Organism (condition) | SFAs (%) | MUFAs (%) | PUFAs (%) | n3 PUFAs (%) |
|---|---|---|---|---|---|---|
| 2 | Rhodotorula mucilaginosa | yeast (normal) | 22 ± 3 | 71 ± 3 | 7 ± 0 | 0 ± 0 |
| 3 | Cryptococcus victoriae | yeast (normal) | 17 ± 4 | 80 ± 5 | 3 ± 3 | 0 ± 0 |
| 3 | P. tricornutum | microalgae (normal) | 21 ± 1 | 33 ± 2 | 45 ± 3 | 11 ± 1 |
| 3 | N. salina | microalgae (normal) | 31 ± 6 | 36 ± 2 | 33 ± 7 | 8 ± 1 |
| 3 | N. oculata | microalgae (normal) | 0 ± 1 | 4 ± 7 | 96 ± 7 | 28 ± 4 |
| 1 | Dunaliella tertiolecta | microalgae (normal) | 0 | 32 | 68 | 52 |
| 1 | Cyclotella cryptica | microalgae (normal) | 31 | 0 | 69 | 14 |
| 1 | Cyclotella cryptica | microalgae (nitrogen deficient) | 29 | 17 | 54 | 13 |
| 1 | B. braunii | microalgae (normal) | 0 | 70 | 30 | 12 |
| 1 | C. reinhardtii | microalgae (nitrogen deficient) | 15 | 10 | 75 | 22 |

Assays for analysis of lipid composition showed changes in triacylglycerol (TAG) composition with some compounds and algae strains. A consistent decrease in PUFAs was observed with N. oculata when treated with cAMP (Table 22).

TABLE 22

| Condition | Concentration | SFAs (% of total lipids) | UFAs (% of total lipids) | All other PUFAs and MUFAs (% of UFAs) | n3 PUFAs (% of UFAs) |
|---|---|---|---|---|---|
| Normal | | 24 | 76 | 63 | 37 |
| Cycloheximide (exponential) | 40 nM | 39 | 61 | 67 | 33 |
| Glycerol | 11 mM | 39 | 61 | 84 | 16 |
| DMSO + bicarbonate | 0.4% + 7 mM | 49 | 51 | 63 | 37 |
| Quinacrine | 4 nM | 53 | 47 | 55 | 45 |
| cAMP | 40 nM | 55 | 45 | 49 | 51 |
| EGCG | 4 μM | 57 | 43 | 35 | 65 |
| Forskolin | 40 nM | 59 | 41 | 39 | 61 |

Table 22 includes PUFAs with >5% difference relative to the control. Calculated based on $^1$H NMR integral ratios for the proton signals for the methyl group of PUFA components vs. the methyl groups of monounsaturated and saturated components.

The results summarized in Table 22 also show that sodium bicarbonate increases PUFA levels in P. tricornutum.

We also observed changes in the fatty acid profiles of microalgae in batch culture upon addition of screened compounds from Example 1. We examined the effect of growth conditions on the PUFA levels using $^1$H NMR spectroscopy to analyze lipid extracts. The PUFA ratios were determined and indicate the effect of each compound on the saturation levels of algae TAGs (Table 23). A more pronounced effect was observed with N. oculata (Table 23). Notably, cAMP consistently showed an effect across species with a PUFA ratio up to 52:48 (400 nM, Nannochloris sp.).

TABLE 23

| Algae | Condition | n3-PUFA Ratio |
|---|---|---|
| N. salina (110409) | Control | 13:87 |
| | Indole acetic acid (40 μM) | 18:82 |
| | Orlistat (10 μM) | 18:82 |

TABLE 23-continued

| Algae | Condition | n3-PUFA Ratio |
|---|---|---|
| N. oculata | Control | 27:73 |
| | PTPI2 (4 nM) | 20:80 |
| | Orlistat (40 nM) | 16:84 |
| | 1% DMSO | 17:83 |
| | cAMP (400 nM) | 22:78 |
| | Cycloheximide (40 nM) | 20:80 |
| | Quinicrine (4 or 40 nM) | 20:80 |
| | Glycerol (11 mM) | 10:90 |
| | Fructose (28 mM) | 9:91 |
| N. oculata | Control | 38:62 |
| | Forskolin (4 nM) | 24:76 |
| | cAMP (40 nM or 4 μM) | 23:77 |
| | Epigallocatechin gallate (40 nM) | 23:77 |
| | Quinacrine (4 nM) | 21:79 |
| | 0.4% DMSO + Sodium Bicarbonate (0.6 g/L) | 19:81 |
| Nannochloris sp. | Control | 41:59 |
| | Epigallocatechin gallate (4 nM) | 49:51 |
| Nannochloris sp. | Control | 38:62 |
| | cAMP (400 nM) | 52:48 |
| | cAMP (40 nM) | 45:55 |
| | Bisindolemaleimide (400 nM) | 44:56 |
| N. oculata | Control | 33:67 |
| | Forskolin (40 nM) | 27:83 |
| | cAMP (400 nM) | 26:84 |
| | Epigallocatechin gallate (400 nM) | 26:84 |
| | Quinacrine (40 nM) | 26:84 |
| P. tricornutum | Control | 12:82 |
| | Sodium Bicarbonate (0.6 g/L) | 22:82 |

Figure 18:
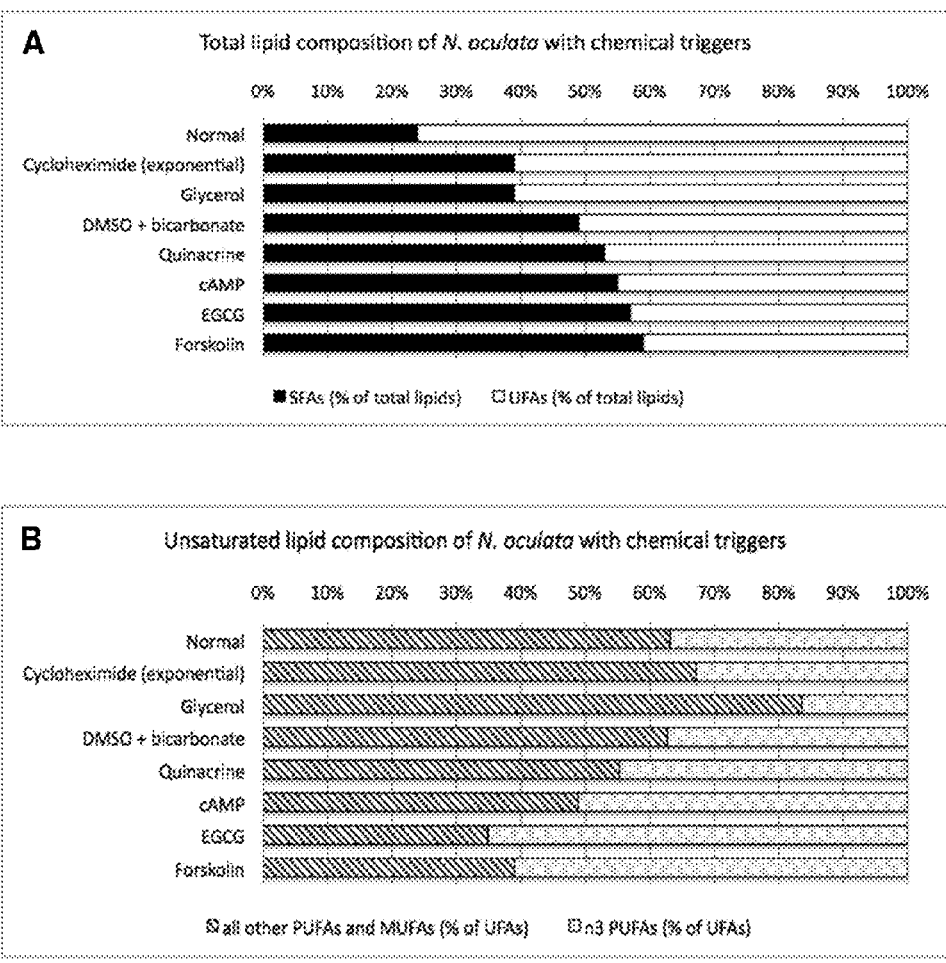
FIG. 18A depicts a comparison of the total fatty acid saturation profile of *N. oculata* with cycloheximide, glycerol, DMSO and bicarbonate, quinacrine, cAMP, EGCG, and forskolin.
FIG. 18B depicts unsaturated fatty acid profile of *N. oculata* with cycloheximide, glycerol, DMSO and bicarbonate, quinacrine, cAMP, EGCG, and forskolin. 500 mL cultures of media and algae, with compounds added in 2 mL of DMSO. The air bubbling and stirring for all cultures was started at day 0. Controls are without the addition of DMSO. Cultures were harvested 6 days into stationary phase. The cultures are extracted and then analyzed using $^1$H NMR spectroscopy.

The most pronounced effect observed was with *N. oculata* upon addition of quinacrine, cAMP, and EGCG, and also adding sodium bicarbonate (FIG. 18 and Table 24). Other algae, such as *N. salina* and *P. tricornutum*, which under normal conditions already contain a lower amount of PUFAs, are minimally affected by compound treatment.

TABLE 24

| n | Condition | SFAs (%) | MUFAs (%) | PUFAs (%) | n3 PUFAs (%) |
|---|---|---|---|---|---|
| 3 | Normal | 0 ± 1 | 4 ± 7 | 96 ± 7 | 28 ± 4 |
| 1 | Glycerol (1 g/L) | 30 | 33 | 38 | 10 |
| 1 | Orlistat (40 nM) | 3 | 29 | 68 | 16 |
| 1 | Quinacrine (400 nM) | 3 | 12 | 76 | 17 |
| 1 | cAMP (40 µM) | 19 | 14 | 67 | 17 |
| 1 | DMSO (1%) | 7 | 32 | 61 | 17 |
| 1 | EGCG (400 nM) + Bicarbonate (0.6 g/L) | 14 | 10 | 76 | 19 |
| 1 | EGCG (400 nM) | 10 | 5 | 85 | 20 |
| 1 | Bicarbonate (0.6 g/L) | 0 | 13 | 87 | 20 |

These results indicate that various compounds are able to alter lipid composition and levels of unsaturation in microalgae, as determined by NMR spectroscopy. Such compounds may be useful for tailoring the lipid product for the production of a better biofuel composition[53].

Example 3

The following Example relates to the identification and characterization of chemical modulators of lipid productivity in oleaginous microalgae. This example describes phenotypic screening with microalgae to study lipid metabolism and to discover organic small molecules as chemical triggers that increase growth and lipid production. A microplate assay was developed for analysis of intracellular lipids using Nile Red fluorescence in order to screen a collection of diverse bioactive organic molecules (e.g., kinase inhibitors) with four strains of oleaginous microalgae (*Nannochloropsis salina, Nannochloropsis oculata, Nannochloris* sp., and *Phaeodactylum tricornutum*). Several small molecules identified in microplate screening increased lipid productivity by over 200% without decreasing growth and biomass production. Selected compounds were further investigated in the context of larger batch culture experiments (e.g., 500 mL) and demonstrated to increase lipid levels up to 84%, while maintaining or increasing the specific growth rate. Bioactive molecules such as forskolin and quinacrine were also identified as probes of microalgae lipid pathways. Additionally, common antioxidants, such as epigallocatechin gallate and butylated hydroxyanisole (BHA), were identified that increase lipid productivity. It is believed that these common antioxidants represent new probes of oxidative signaling pathways for photooxidative protection.

Materials and Methods

Microalgae Strains and Maintenance

*Phaeodactylum tricornutum* (UTEX B2089), *Nannochloropsis oculata* (UTEX LB2164), and *Nannochloris* sp. (UTEX LB2055) were purchased from the UTEX Culture Collection of Algae at the University of Texas. *Nannochloropsis salina* (CCMP 537) was purchased from the Provasoli-Guillard National Center for Marine Algae and Microbiota (NCMA) [formerly, the Center for the Culture of Marine Phytoplankton at the Bigelow Laboratory for Ocean Sciences (CCMP)]. *P. tricornutum* and *N. salina* were cultured in F/2 medium and *N. oculata* and *Nannochloris* sp. were cultured in Erdschreiber's medium. Microalgae were maintained at 22° C. on a 16:8 h light/dark cycle and aerated by stirring with bubbling filtered air or by orbital shaking.

Microalgae Stock Cultures

All materials for assay experiments were autoclaved before each use to maintain axenic microalgae cultures for screening. Microalgae species are verified for axenicity using a Nikon Eclipse TS-100 light microscope (Nikon, Japan) before each experiment. For each microplate, 10 mL of diluted microalgae stock was prepared by diluting a . . . stationary phase culture to 0.075 absorbance units with appropriate media without sodium bicarbonate supplementation. Diluted stock solutions are made immediately prior to use for consistency and optimal plate growth. Cell density was measured on a Thermo Scientific Genesys 10S V is Spectrophotometer (ThermoFisher, San Jose), using a 1-mL cuvette at 680 nm.

Microalgae Growth Conditions for Microplate Assay

All wells in a parafilmed-sealed clear 96-well microplate contained 100 µL microalgae cells suspension diluted in 150 µL of appropriate media to obtain a final absorbance of 0.075 (680 nm). *P. tricornutum* and *N. salina* were cultivated by supplementing 1.2 g/L of sodium bicarbonate to the growth media as a carbon source. Control wells in microplates contained microalgae with 0.4% v/v DMSO. Perimeter wells contained no microalgae but were filled with 100 µL water and 150 µL media to prevent edge effects and used for background subtraction.

Addition of Small Molecules for Microplate Assay

Compounds were diluted by serial dilution to desired concentrations starting from a 10 mM compound stock dissolved in DMSO or water. Growth media and 1 µL of compound were dispensed to all wells before the addition of microalgae suspension to minimize the effect of exothermic reaction of DMSO and media. Compounds were assigned randomly within a microplate but each plate replicate had identical compound position per well.

Compound Selection and Preparation of Stock Solutions

Compounds were selected based on examples of previously reported biological activity (e.g., for yeast and mammalian cells) and were ordered from the following vendors: Fisher BioReagents, Sigma Aldrich, Cayman Chemicals, ChromaDex, Promega, MP Biomedicals, EMD Millipore Chemicals, Tocris Cookson, Axxora LLC, Acros Organics, Cell Signaling Technology, Andwin Scientific, LC Laboratories, Research Products International Corp, Enzo Life Sciences, TCI America, Alfa Aesar, and Supelco (Table 25). Compounds were stored under advised conditions after purchasing from the manufacturer to ensure quality retention. Stock solutions at 10 mM in DMSO were prepared in amber glass vials and stored in the dark at −20° C. To prevent cross contamination during screening, individual compounds were added to separate wells in a PCR plate and organized using a pre-made plate map. Serial dilutions used in the secondary screening were diluted by rows within the same PCR plates. Dilutions and compounds were transferred manually using a multi-channel pipet. All plates were sealed with aluminum plate seals and stored at −20° C. A plate map was used to keep track of each compound in the microplate well based on molecule name, collection number, and CAS number. Table 25 lists the compounds, vendors, known biological activity.

TABLE 25

| Molecule | Compound class and bioactivity | Catalog # | Vendor |
|---|---|---|---|
| Abscisic acid | Plant growth hormone (agonist of antioxidant response element at 37.6 μM) | 190673 | MP Biomedicals |
| Acetaminophen | Analgesic, inhibitor of COX (arachidonate 15-LO, $IC_{50}$ = 28.38 μM) | A5000 | Sigma Aldrich |
| AG 82 | Inhibitor of protein tryrosine kinase (EGFR tyrosine kinase, $IC_{50}$ = 3 μM) | 658400 | EMD Millipore Chemicals |
| AICAR | Activator of AMPK, inhibitor of fatty acid and sterol synthesis (0.5 mM), inactivates HMG-CoA reductase in rat hepatocytes, inhibitor of insulin-stimulated glucose uptake (0.5 mM), and inhibitor of NFκB and C/EBP pathways | A9978 | Cayman Chemical |
| Aloisine A | Inhibitor of CDKs ($IC_{50}$ = 150 nM, 120 nM, 400 nM, and 200 nM for Cdk1/cyclin B, Cdk2/cyclin A, Cdk2/cyclin E, and Cdk5/p25, respectively, GSK (GSK-3, $IC_{50}$ = 500 nM and 1.5 μM for GSK-3α, GSK-3β, respectively), and c-Jun N-terminal kinase ($IC_{50}$ = ~3-10 μM) | 128125 | EMD Millipore Chemicals |
| Apigenin | Inhibitor of MAPK activity, PKC-like activity | 178278 | EMD Millipore Chemicals |
| Arctigenin | Plant lignan, antiviral and antitumor activity | 50810264 | Tocris Cookson |
| Atrazine | Herbicide | 49085 | Supelco |
| Baicalein | Anti-inflammatory, anti-thrombotic, anti-proliferative and anti-mitogenic activity, inhibitor of 12-LO ($IC_{50}$ = 0.64 μM) and 15-LO (IC50 = 1.6 μM) | BML-EI106 | Axxora |
| 6-Benzylaminopurine | Cytokinin, plant growth regulator | 22641 | Acros Organics |
| Bisindolylmaleimide | Inhibitor of kinases (PKC, $K_i$ = 10 nM; PKA, $K_i$ = 2 μM) | 270-049-M001 | Axxora |
| Bohemine | Inhibitor of CDK ($IC_{50}$ = 1 μM) | 203600 | EMD Millipore Chemicals |
| BPDQ (4-[(3-bromophenyl)amino]-6,7-diaminoquinazoline) | Inhibitor of the tyrosine kinase activity of the EGFR ($IC_{50}$ = 120 pM) | 203697 | EMD Millipore Chemicals |
| BPIQ-II | Inhibitor of the tyrosine kinase activity of the EGFR ($IC_{50}$ = 8 pM) | 203704 | EMD Millipore Chemicals |
| Butein | Plant polyphenol, inhibitor of the tyrosine kinase activity of the EGFR ($IC_{50}$ = 65 μM) | 203987 | EMD Millipore Chemicals |
| BHA (Butylated hydroxyaniaole) | Antioxidant, DPPH free radical scavenging activity ($IC_{50}$ = 43 μM) | 2101159 | MP Biomedicals |
| Caffeic acid | Plant phenolic compound with anti-tumor, antiviral, antioxidant and anti-inflammatory activity, inhibitor of 5- and 12-LO (5-LO, $IC_{50}$ = 3.7 μM) | 270-231 | Axxora |
| cAMP | Activator of kinases | 22580 | Acros Organics |
| Cantharidin | Inhibitor of protein phosphatase 2A ($IC_{50}$ = 40 nM) | 210155 | EMD Millipore Chemicals |
| (+)-Catechin | Natural flavonoid with antioxidant, chemopreventative, and antitumor properties | ASB-00003310 | ChromaDex |
| CDC25 phosphatase inhibitor I | Inhibitor of CDC25 phosphatase family ($IC_{50}$ = 2.4, 3.9, 6.3, 5.4, and 4.6 μM for 25A, 25B2, 25B3, 25C, and 25C-cat, respectively) | 217691 | EMD Millipore Chemicals |
| CDK2 inhibitor II | Inhibitor of CDK2 ($IC_{50}$ = 60 nM) | 219445 | EMD Millipore Chemicals |
| CDK4 Inhibitor II NSC | Inhibitor of CDK4/cyclin D1 ($IC_{50}$ = 200 nM) | 219477 | EMD Millipore Chemicals |
| CDK4 Inhibitor III | Inhibitor of CDK4 ($IC_{50}$ = 6.0 μM for CDK4/D1 and >200 μM for CDK2/A) | 219478 | EMD Millipore Chemicals |
| CDK4/6 inhibitor IV | Inhibitor of CDK4 and CDK6 ($IC_{50}$ = 1.5 and 5.6 μM, respectively) | 219492 | EMD Millipore Chemicals |
| Cerulenin | Antifungal, inhibitor of FAS | ICN19509801 | MP Biomedicals |
| Citric acid monohydrate | Phosphofructokinase inhibitor, glycolysis regulator | 12491 | Acros Organics |
| Curcumin | Anti-inflammatory, inhibitor of LO | 21858 | Acros Organics |

TABLE 25-continued

| Molecule | Compound class and bioactivity | Catalog # | Vendor |
|---|---|---|---|
| Cycloheximide | Antiobiotic, inhibitor of protein synthesis | 35742 | Acros Organics |
| D-Glucosamine hydrochloride | Component of chitosan, used to treat osteoarthritis | 11990 | Acros Organics |
| Eicosapentaenoic acid | Fatty acid, inhibitor of COX | NC9297605 | Cell Signaling Technology |
| (−)-Epicatechin | Antioxidant, natural product from green tea | ASB-00005125 | ChromaDex |
| (−)-Epicatechin gallate | Antioxidant, natural product from green tea, inhibitor of protease (FAB1 inhibitor, $IC_{50}$ = 0.2 μM) | ASB-00005135 | ChromaDex |
| (−)-Epigallocatechin | Antioxidant, natural product from green tea | ASB-00005145 | ChromaDex |
| (−)-Epigallocatechin gallate | Polyphenol catechin antioxidant found in green tea, antitumor, antioxidant, anticarcinogenic, antimutagenic, anti-inflammatory, and neuroprotective activity, inhibitor of iNOS (NOS II), MAP kinase mediated signalling pathways, telomerase and DNA methyltransferase, and FABI ($IC_{50}$ = 0.2 μM) | ALX-270263 | Axxora (or ChromaDex) |
| D,L-Epinephrine | Hormone, inhibitor of adrenergic receptors | 2151064 | MP Biomedicals |
| Erbstatin analog | Inhibitor of the EGFR associated tyrosine kinase1 and histone lysine methyltransferase G9a ($IC_{50}$ = 2.818 μM) | 2158813 | MP Biomedicals |
| Esculetin | Inhibitor of LO and activator of MAPK | E0386 | TCI America |
| ET-18-OCH3 | Cytotoxic agent that shows selective cytocidal activity against neoplastic cells and virally transformed cells, inhibitor of phosphatidylinositol-specific phospholipase C (PI-PLC, $IC_{50}$ = 9.6 μM) | 341207 | EMD Millipore Chemicals |
| Ethyl 3,4-dephostatin | Inhibitor of PTP1b ($IC_{50}$ = 3.2 μM) | 263203 | EMD Millipore Chemicals |
| Ethyl palmitate | Fatty acid, anti-inflammatory activity | —[b] | Acros Organics |
| FAAH Inhibitor I | Inhibior of fatty acid amide hydrolase ($IC_{50}$ = 396 nM) | 341248 | EMD Millipore Chemicals |
| FAAH Inhibitor II | Inhibitor of fatty acid amide hydrolase ($IC_{50}$ = 4.6 nM) | 341249 | EMD Millipore Chemicals |
| Forskolin | Inhibitor of MAPK, stimulates cAMP, activator of PKA, activator of adenylate cyclase | BP25201 | Fisher BioReagents (or AK Scientific) |
| Genistein | Isoflavone, antioxidant, inhibitor of tyrosine kinase, inhibitor of PPAR, inhibitor of topoisomerase | 32827 | Acros Organics |
| Gibberellic acid | Plant hormone, stimulates seed germination | 41091 | Acros Organics |
| Glycerol | Triacylglycerol precursor | BP229 | Fisher BioReagents |
| Gossypol | Plant phenol, inhibitor of PKC | 195210 | MP Biomedicals |
| Halopemide | Antagonist of dopamine receptor, inhibitor of phospholipase D2 | H3041 | Sigma Aldrich |
| Ibuprofen | Inhibitor of COX | 25861 | Acros Organics |
| Indole acetic acid (IAA) | Auxin plant hormone | 12216 | Acros Organics |
| Indole-3-butyric acid | Plant growth hormone | ICN10204301 | MP Biomedicals |
| Indomethacin | Inhibitor of COX | A19910 | Alfa Aesar |
| Jasmonic acid | Plant growth regulator | 50213381 | Research Products International |
| JZL184 hydrate | Inhibitor of monoacylglycerol lipase ($IC_{50}$ = 6 nM) | J3455 | Sigma Aldrich |
| K-252a | Inhibitor of PKC (Ki = 25 nM), trk tyrosine kinase family members (gp140trk, $IC_{50}$ = 3 nM) and cGMP-dependent protein kinase | BML-EI152 | Enzo Life Sciences |
| Kenpaullone | Inhibitor of CDK1/cyclin B ($IC_{50}$ = 400 nM), CDK2/cyclin A (IC50 = 680 nM), CDK5 ($IC_{50}$ = 850 nM), GSK-3β inhibitor ($IC_{50}$ = 23 nM). | BML-EI310 | Enzo Life Sciences |
| Ketoconazole | Inhibitor of cytochrome P450 (progesterone 15-alpha hydroxylase, $IC_{50}$ = 0.369 nM) and 14-alpha-demethylase, antifungal agent ($IC_{50}$ = 0.01 μM) against *Trichophyton rubrum* | BP2734 | Fisher BioReagents |

TABLE 25-continued

| Molecule | Compound class and bioactivity | Catalog # | Vendor |
|---|---|---|---|
| Kinetin | Plant growth regulator, activator of cAMP, inhibitor of Rho kinase 2 | 22650 | Acros Organics |
| Lactic acid | Intermediate in the fermentation of sugar | BP26615 | Fisher BioReagents |
| SB202190 | Inhibitor of p38 MAPK (p38α and β isoforms, $IC_{50}$ = 50 and 100 nM at SAPK2a/p38 and SAPK2b/p38β2, respectively) | 50-810-911 | Tocris Cookson |
| Methyl jasmonate | Plant hormone and defense compound | M1068 | TCI America |
| Naproxen | Inhibitor of COX | 2190247 | MP Biomedicals |
| Naphthyl acid phosphate, monosodium salt | Broad-spectrum inhibitor of PTP | 479775 | EMD Millipore Chemicals |
| Olomoucine | Inhibitor of CDC2 protein kinase ($IC_{50}$ = 6 μM), CDK1 ($IC_{50}$ = 4.6 μM), and CDK2 ($IC_{50}$ = 7 μM) | V2372 | Promega |
| Orlistat (tetrahydrolipstatin) | Diacylglycerol lipase inhibitor ($IC_{50}$ = 1 μM) | O4139 | Sigma Aldrich |
| PD98059 | Inhibitor of cytochrome 9450, MEK1 activation and the MAPK cascade | 9900 | Cell Signaling Technology |
| Phorbol 12-myristate 13-acetate | Inhibitor of PKC | P-1680 | LC Laboratories |
| Piceatannol | Plant metabolite, inhibitor of PKA (rat liver catalytic subunit; $IC_{50}$ = 3 μM), PKC ($IC_{50}$ = 8 μM), and MLCK ($IC_{50}$ = 12 μM) | 527948 | EMD Millipore Chemicals |
| PP2 | Inhibitor of Src family of protein tyrosine kinases. Inhibits p56lck p59fynT & Hck | 529573 | Andwin Scientific |
| Propyl gallate | Antioxidant, inhibitor of microsomal lipid peroxidation ($IC_{50}$ = 4.5 μM) | 13158 | Acros Organics |
| Palmityl trifluoromethyl ketone | Inhibitor of calcium-dependent phospholipase A2 ($IC_{50}$ = 3.8 μM) | P8727 | Sigma-Aldrich |
| PTP Inhibitor II | Inhibitor of PTP ($K_i$ = 128 μM) | 540205 | EMD Millipore Chemicals |
| Quinacrine | Inhibitor of PLA2 and MAO | 551850 | EMD Millipore Chemicals |
| Rapamycin | Immunosuppressant, blocks signaling that leads to p70 S6 kinase activation ($IC_{50}$ = 50 pM) | R-5000 | LC Laboratories |
| Resveratrol | Phenolic with antifungal, antitumor, and antioxidative properties Inhibitor of COX-1 ($ED_{50}$ = 15 μM) | 554325 | EMD Millipore Chemicals |
| RHC 80267 | Diacylglycerol lipase inhibitor, important second messenger in signal transduction pathways | R2028 | Sigma Aldrich |
| Roscovitine | Inhibitor of CDKs (p34cdk1/cyclin B, $IC_{50}$ = 650 nM) | 557360 | EMD Millipore Chemicals |
| Salicylic acid | Anti-infective, antifungal, and keratolytic agent, inhibitor of human carbonic anhydrase 2 ($K_i$ = 7.1 μM) | 41922 | Acros Organics |
| Staurosporine | Indolocarbazole, inhibitor of PKC which enhances cAMP-mediated responses, inhibitor of the ERK signaling pathway (EGFR, $IC_{50}$ = 0.4467 μM) | BP2541100 | Fisher BioReagents |
| SU9516 | Inhibitor of CDKs ($IC_{50}$ = 22 nM) | 572650 | EMD Millipore Chemicals |
| Vitamin E | Plant tocopherol, antioxidant | —[b] | Alfa Aesar |
| Theobromine | Plant alkaloid, inhibitor of ERK signaling pathway (potency = 0.004 μM) | 25882 | Acros Organics |

TABLE 25-continued

| Molecule | Compound class and bioactivity | Catalog # | Vendor |
|---|---|---|---|
| Zeatin | Cytokinin, plant growth regulator | 26429 | Acros Organics | aWhen readily available, biological activity is listed based on information obtained from vendor website, PubChem, or the internet.
bItem is no longer available from vendor.
Abbreviations are as follows:
EGFR = epidermal growth factor receptor,
CDK = cyclin dependent kinase,
ERK = extracellular signal regulated kinase,
GSK = glycogen synthase kinase,
MAPK = mitogen-activated protein kinase,
PKC = protein kinase C,
AMP = adenosine monophosphate,
CDC = cell division cycle,
PLA = phospholipase A,
PTP = protein tyrosine phosphatase,
PPAR = peroxisome proliferator-activated receptor,
FAS = fatty acid synthesis,
FAB = fatty acid biosynthesis,
MLCK = myosin light chain kinase,
MAO = monoamine oxidase,
COX = cyclooxygenase,
LO = lipoxygenase,
iNOS = inducible nitric oxide synthase, and
AMPK = AMP-activated protein kinase.

Microplate Assay

Sodium bicarbonate supplementation for assay preparation. Assay plates contained 100 µL of microalgae cell suspension in 150 µL of appropriate media that was dispensed using an automated plate dispenser (Microflo Select, Biotek, Vermont, USA). Microalgae were grown in a 96-well microplate (Corning 3370) covered with a clear lid and sealed with parafilm along the edges to minimize evaporation. For $N.$ $salina$ and $P.$ $tricornutum$, supplemental sodium bicarbonate (1.2 g/L concentration) was added to media to provide optimal growth conditions, based on our preliminary studies of microalgae growth levels in microplates.

To establish if supplemental carbon was required for optimal growth of each microalgae strain in microplates, growth experiments were first performed for all algae species using a gradient of sodium bicarbonate (2× dilution ranging from 0.3-1.2 g/L) in media, and investigated with and without the addition of 0.4% DMSO. From these experiments, it was determined that a concentration of 1.2 g/L sodium bicarbonate produced the optimal growth based on cell density (i.e., absorbance) in both $P.$ $tricornutum$ and $N.$ $salina$, thus 1.2 g/L was utilized for microplate assays with these strains. Low concentrations or no addition of sodium bicarbonate was determined to be more optimal for growth of $N.$ $oculata$ and $Nannochloris$ sp. in microplates, thus no supplemental sodium bicarbonate was utilized for microplate assays with these strains.

Preparations of compounds and microalgae in microplates. Microplate assays were investigated with either three or four replicates along with a separate microplate containing only control wells to compare growth. Due to extensive evaporation in exterior wells over time due to edge effects, our unique algae plate layout was designed to use the 60 interior wells out of 96 wells for the experiment. The 36 outer wells were filled with millipore-filtered water and media to prevent evaporation and edge effects in the inner algae wells, as well as serve as blanks. The 60 wells in the center contain a total volume of 251 µL (100 µL of media+1 µL DMSO compound stock +150 µL dilute algae stock). All dilutions started from 10 mM compound stock in DMSO. DMSO stock solution is added first to the microplate containing media only so that the exothermic reaction of DMSO and media does not negatively affect algae growth. To each control wells, 1 µL of DMSO was added. Microplates resume the same shaker position after each analysis. Compounds investigated with water delivery (in place of DMSO) were added to microplates before the addition of microalgae.

Microalgae growth conditions in microplates. Microalgae were grown in 96-well clear, round, flat-bottom microplates (Costar 3370). Clear microplates were necessary in order to give maximum light exposure for optimal growth of microalgae during the assay. The plates were grown under full spectrum incident uniform lighting at a 16:8 hour light/dark cycle with 90-150 µM photons/m$^2$/s (High Efficiency T-5 Grow Lights—Gardeners Supply Co, Vermont). The shakers were kept at a constant orbital shaking of 150 rpm. Ambient temperature is 22±3° C. Absorbance (680 nm) and chlorophyll fluorescence (excitation at 360 nm and emission at 645 nm) analyses were taken every day on the Synergy HT Multimode Plate Reader (Biotek, Vermont, USA), in order to monitor cell density and chlorophyll production in algae over the growth cycle.

Screening for Intracellular Lipids in Microalgae

Microalgae growth was measured based on cell density, which was monitored daily with a multimode UV-Vis spectrophotometer and spectrofluorimeter plate reader at absorbance of 680 nm and chlorophyll fluorescence at excitation/emission wavelength of 360/645 nm, respectively. Analysis of intracellular lipids in microalgae was performed using Nile Red fluorescence (530/590 nm) intensity, as described below, after microalgae has grown 3 days in stationary phase, which occurred on Day 14 for $N.$ $salina$, $P.$ $tricornutum$, and $N.$ $oculata$ and Day 21 for $Nannochloris$ sp. Nile Red fluorescence intensity values are reported as the difference relative to the DMSO control.

Nile Red Optimized Procedure for Microplate Assay

Intracellular lipid analysis for $P.$ $tricornutum$ involved the addition of 25 µL of 1 mg/mL Nile Red dissolved in acetone followed by a 20-minute kinetic fluorescence analysis using a multimode plate reader at excitation and emission wavelength of 530/40 nm and 590/40 nm, respectively. Intracellular lipid analysis in $N.$ $oculata$, $Nannochloris$ sp. and $N.$ $salina$ require the addition of a 25 µL mixture of 1:1 (v/v) DMSO:media before the addition of Nile Red and analysis was performed at 35° C. This microplate method was optimized for this study based on the procedure by Chen et al. (30). The average maximum Nile Red fluorescence intensity from each well was used to compare lipid levels. Background fluorescence intensity of wells was subtracted. Data analysis was acquired with Gen5. Two methods of lipid analysis were attempted based on comparison with the controls within the same plate and other plate replicates.

Statistical Analysis for Microplate Screening

Reported means, standard deviations, standard errors, and p-values were calculated for each compound based on three replicates (one compound per microplate). Error analysis for controls included six well replicates per plate all in the same row in addition to an external plate of 54 control wells. In microplates, compounds that caused Nile red fluorescence intensity readings to significantly deviate from the control ($p<0.01$) were considered a "hit" (Tables 26 and 27). T-test analysis was based on a two-sided analysis using unequal variance.

Table 26 lists the number of compounds identified with positive effects in microplate screening with p-values $<0.05$ and $<0.01$. In Table 26, microalgae were screened with three plate replicates analyzed simultaneously ($n=3$). The maximum Nile Red fluorescence intensities of each well were used for calculating p-values using an independent, two-tailed t-test with unequal variance.

TABLE 26

| Algae species | Concentration | # of hits[x] | # of hits with increase relative to control[x] | # of hits[y] | # of hits with increase relative to control[y] |
|---|---|---|---|---|---|
| P. tricornutum | 40 µM | 22 | 2 | 21 | 2 |
|  | 200 nM | 11 | 3 | 9 | 2 |
| Nannochloris sp. | 20 µM | 8 | 0 | 7 | 0 |
|  | 200 nM | 11 | 10 | 1 | 0 |
| N. salina | 20 µM | 17 | 11 | 12 | 6 |
|  | 200 nM | 2 | 0 | 1 | 0 |
| N. oculata | 20 µM | 26 | 24 | 18 | 17 |
|  | 200 nM | 11 | 10 | 6 | 5 |

[x] $p < 0.05$ and
[y] $p < 0.01$.

Table 27 lists a summary of compounds indicate a positive effect (>20% increase) for intracellular lipid levels based on Nile Red fluorescence intensity in the initial microplate screening. In Table 27, the listed compounds show an increase in Nile Red fluorescence intensity compared to the control. The initial screening involves a microplate assay with six controls in each plate for four different microalgae strains. A separate control plate contained 54 control wells with DMSO to factor in controls in different wells in the plate. The assay was investigated at two concentrations per algae strain, three replicates per compound, one compound per plate. Nile Red fluorescence was analyzed utilizing Nile Red method A described above. Compounds listed show an increase in intracellular lipid levels and are all statistically significant ($p<0.05$).

TABLE 27

| Algae | Molecule | Nile Red Fluorescence % Increase | P value |
|---|---|---|---|
| P. tricornutum (compounds tested at 40 µM) | CDK2 inhibitor II | 150.6 | 9.56E−11 |
|  | SB 202190 | 115.0 | 7.04E−03 |

TABLE 27-continued

| Algae | Molecule | Nile Red Fluorescence % Increase | P value |
|---|---|---|---|
| P. tricornutum (compounds tested at 200 nM) | Benzylaminopurine | 105.9 | 4.67E−02 |
|  | CDK2 inhibitor II | 50.3 | 1.53E−05 |
|  | Kinetin | 25.2 | 4.47E−03 |
| N. oculata (compounds tested at 200 nM) | Abscisic acid | 87.0 | 1.96E−05 |
|  | Epigallocatechin gallate | 207.5 | 4.52E−02 |
|  | Zeatin | 157.1 | 3.23E−02 |
|  | Arctigenin | 152.2 | 4.91E−02 |
|  | AG82 | 144.5 | 2.14E−02 |
|  | Rapamycin | 141.6 | 2.25E−02 |
|  | Cycloheximide | 137.9 | 4.88E−02 |
|  | Epinephrine | 129.3 | 1.96E−02 |
|  | Lactic Acid | 128.8 | 3.74E−02 |
|  | Resveratrol | 120.4 | 4.43E−02 |
|  | Aloisine A | 117.7 | 3.67E−02 |
| N. salina (compounds tested at 20 µM) | PTP Inhibitor II | 87.2 | 4.57E−02 |
|  | Bohemine | 61.0 | 1.50E−02 |
|  | Ibuprofen | 59.0 | 5.07E−08 |
|  | Baicalein | 37.3 | 6.46E−03 |
|  | Kenpaullone | 34.8 | 1.05E−11 |
|  | Abscisic acid | 34.5 | 3.96E−03 |
|  | Apigenin | 34.3 | 3.64E−02 |
|  | Ketoconazole | 32.0 | 3.31E−02 |
|  | Salicylic acid | 25.5 | 1.83E−06 |
| Nannochloris sp. (compounds tested at 20 µM) | Epigallocatechin gallate | 214.9 | 2.18E−02 |
|  | Apigenin | 136.7 | 9.14E−05 |
|  | CDC25 | 130.9 | 5.21E−10 |
|  | Bohemine | 122.0 | 1.68E−02 |
|  | Rapamycin | 117.3 | 3.13E−04 |
|  | Kenpaullone | 97.7 | 3.25E−02 |
|  | Indole acetic acid | 95.4 | 1.24E−03 |
|  | Acetaminophen | 89.7 | 2.11E−04 |
|  | Ibuprofen | 80.2 | 5.35E−11 |
|  | SB 202190 | 54.6 | 2.32E−02 |
|  | AG82 | 54.2 | 5.56E−03 |
|  | Resveratrol | 53.3 | 1.28E−03 |
|  | Forskolin | 45.3 | 7.33E−03 |
|  | Epinephrine | 44.9 | 7.79E−10 |
|  | Erbstatin analog | 40.5 | 2.42E−03 |
|  | Salicylic acid | 32.3 | 1.92E−03 |
|  | Lactic Acid | 30.9 | 3.68E−02 |
|  | Roscovitine | 30.8 | 3.46E−04 |
|  | SB 202190 | 28.8 | 1.55E−02 |
|  | PTP Inhibitor II | 27.8 | 2.96E−02 |
|  | Cantharidin | 22.9 | 8.39E−05 |
| Nannochloris sp. (compounds tested at 200 nM) | Ketoconazole | 258.9 | 7.13E−05 |
|  | Bohemine | 146.3 | 2.06E−02 |
|  | Cerulenin | 107.9 | 8.07E−04 |
|  | Abscisic acid | 90.8 | 3.42E−02 |
|  | Kenpaulllone | 84.2 | 2.54E−02 |
|  | Jasmonic acid | 80.5 | 3.07E−02 |
|  | Erbstatin analog | 80.2 | 2.92E−12 |
|  | Salicylic acid | 37.0 | 3.16E−02 |
|  | Theobromine | 34.3 | 8.83E−03 |
|  | CDC25 | 28.2 | 4.02E−05 |

Screening of Lead Compounds in 500 mL Batch Culture

Batch cultures were set up following similar procedures as in microplates with media and compound dissolved in DMSO added before the addition of microalgae suspension. 2 mL of compound, dissolved in DMSO to desired concentration, is added to cultures at day t=0 (except where indicated for temporal studies) to obtain a DMSO concentration of 0.4% v/v in 500 mL, similar to the conditions in microplates. Cell density was monitored by measuring absorbance at 680 nm every 1-2 days. For growth comparison with nutrient-limited conditions, nitrogen-deficient media was prepared containing 33% nitrogen compared to that of normal media.

Lipid Extraction 500-mL cultures were harvested 6 days into stationary phase based on absorbance values. Cells were concentrated by centrifugation and lyophilization to remove water. Non-polar lipids were extracted by sonication and solvent (chloroform-methanol and PBS buffer). Chloroform layer was isolated and concentrated by rotary evaporation and further dried under vacuum (56, 57). Changes in lipid levels for batch cultures were determined by crude lipid extract mass. Lipid extracts were further analyzed for the following: 1) triacylglycerol (TAG) presence and purity by $^1$H Nuclear Magnetic Resonance (NMR) spectroscopy; 2) fatty acid composition using gas chromatography mass spectrometry (GC/MS) after TAG transesterification; and 3) composition of TAG using solid-phase extraction and analysis by matrix assisted laser desorption time-of-flight (MALDI-TOF) mass spectrometry. By NMR spectroscopic analysis, no significant amount of compound was observed in the lipid extract, verifying the confidence in the lipid extract mass.

Results

Results of Screening for Modulators of Lipid Production in Microalgae

We designed a three-phase screening process to identify small molecule probes and chemical triggers to increase growth and lipid levels in oleaginous microalgae relevant for biofuel production (FIG. 1). The initial screening phase utilized 96-well microplates to screen a pilot collection of diverse bioactive molecules selected based on characterized target classes (e.g., in plants, yeast or mammalian cells) (Table 25), with multiple industrially-relevant microalgae strains (selected based on high-lipid content). We then initiated screening with a pilot collection of bioactive molecules in order to screen two or more concentrations with four oleaginous microalgae strains. The microalgae species evaluated in this assay were *Phaeodactylum tricornutum, Nannochloropsis salina, Nannochloropsis oculata*, and *Nannochloris* sp., which have been previously described as valuable for commercial biofuel applications. The microplate assay monitors growth using absorbance and chlorophyll fluorescence measurements during all phases, followed by the addition of the lipophilic dye Nile Red (9-diethylamino-5H-benzo[alpha]phenoxazine-5-one) to measure intracellular lipid levels in stationary phase (30). The second phase of screening involved further dose-response screening in order to confirm the activity of lead compounds that were identified in the microplates. The final screening phase tested the activity of lead compounds in larger 500-mL cultures to quantify and compare lipid levels and composition using traditional methods of lipid analysis, such as gravimetric analysis, $^1$H NMR spectroscopy, microscopy, and mass spectrometric analysis (MALDI-TOF of TAGs and GC/MS of FAMEs) (31). These techniques also facilitated the "pre-characterization" of fuel properties in order to attain desired properties of biodiesel (such as volatility and viscosity) where small changes resulting from unsaturation or chain length can have a substantial effect on fuel properties (e.g., cloud point, oxidative stability) (26, 32). Several lead compounds were also selected for screening with water as a delivery vehicle, instead of DMSO, due to the relevance for industrial-scale applications.

The initial small molecule screening tested 432 unique culture conditions using a collection of 54 bioactive molecules screened with all four microalgae strains at 20 μM and 200 nM concentrations. This preliminary screening evaluated commercially-available bioactive small molecules with characterized target classes, such as various kinase inhibitors, fatty acid synthase (FAS) inhibitors, plant hormones, and oxidative signaling molecules (Table 25). Many of the compounds selected were non-toxic to enhance long-term commercial potential for use in large-scale pond production of microalgae. Optimization of the microplate assay required the addition of sodium bicarbonate or soil extract as a supplemental carbon source, because limited air exchange occurs in microplates, and air or $CO_2$-bubbling was not feasible (33, 34). The addition of sodium bicarbonate as an external inorganic carbon source ensured consistent growth conditions in microplates to allow for comparative studies based on compound treatment.

We observed five outcomes based on growth and lipid phenotypes, depending on both the compound structure and concentration: 1) increase in both growth and lipid production; 2) increase in growth but decrease in lipid production; 3) decrease in growth but increase in lipid production; 4) decrease in both growth and lipid production; and 5) no effect on growth or lipid production. The first three outcomes were the focus of this Example.

Statistical analysis was performed on approximately 800 microplate cultures per species. Average and standard error of the mean were used to compare lipid production based on Nile Red fluorescence intensities. Compounds having a Nile Red fluorescence intensity with a $p < 0.05$ in an independent two-tailed t-test were considered statistical significant (Table 26). Based on this error analysis, microplate assay results with a lipid increase >20% (regardless of growth rate) were considered to be positive results (i.e., hits) for the first phase of the assay. A complete summary of molecules with >20% increase of intracellular lipids based on Nile Red fluorescence intensity is shown in Table 27. Control experiments were performed to ensure that there were no false positives based on compound autofluoresence, and also that compounds did not interfere with the quantification of lipid levels (i.e., enhance or quench the fluorescence) using the Nile Red dye.

Several classes of molecules were identified as having a consistent effect on increasing intracellular lipid levels. Several strains of green microalgae responded positively to compounds that included cAMP, forskolin, and quinacrine. Without wishing to be bound by theory, it is believed that this result suggests that there are conserved metabolic targets among different strains. However, compounds such as (−)-epigallocatechin gallate (EGCG), PTP inhibitor II, and cycloheximide afforded varied responses based on the microalgae strain. Without wishing to be bound by theory, it is believed that this result indicates that regulation of some biological pathways occurs by different mechanisms in different strains.

Based on the results shown in Tables 26 and 27, the following conclusions were made: 1) adding supplemental carbon sources (e.g., sodium bicarbonate) is important for microalgae growth in microplates to successfully develop the microplate assay; 2) the Nile Red fluorescent assay is a rapid and effective way to perform chemical genetic screening and compare intracellular lipid content in a microalgae microplate assay; 3) generally, *N. salina* and *Nannochloris* sp. exhibited more positive increases in intracellular lipid levels, while *N. oculata* and *P. tricornutum* exhibited fewer positive results; and 4) identified chemical triggers that increase intracellular lipid levels for *P. tricornutum* were generally distinct from molecules identified for green microalgae strains.

We also identified several molecules with negligible effects on the growth and lipid levels of microalgae. Without wishing to be bound by theory, it believed that this result suggests that microalgae are robust and have adapted to being exposed to contaminating chemicals in their environment.

Results of Dose-Response Screening of Lipid Modulators for Microalgae in Microplates Based on identified compounds promoting >20% intracellular lipid increase based on Nile red fluorescence intensity relative to the control, a series of different compound/strain combinations were identified to test for concentration-dependent activity. Additional related compounds were also selected based on the target classes or known functions of these lead compounds, such as modulators of lipoxygenase activity, lipase activity, plant hormone activity, protein kinase activity, and oxidative signaling activity (35-37). In total, 42 compounds were evaluated in dose-response screening in four microalgae strains at nine concentrations (ranging from 40 µM to 2 pM) to further characterize the activity of these chemical triggers to effect growth and intracellular lipid levels.

Figure 20:
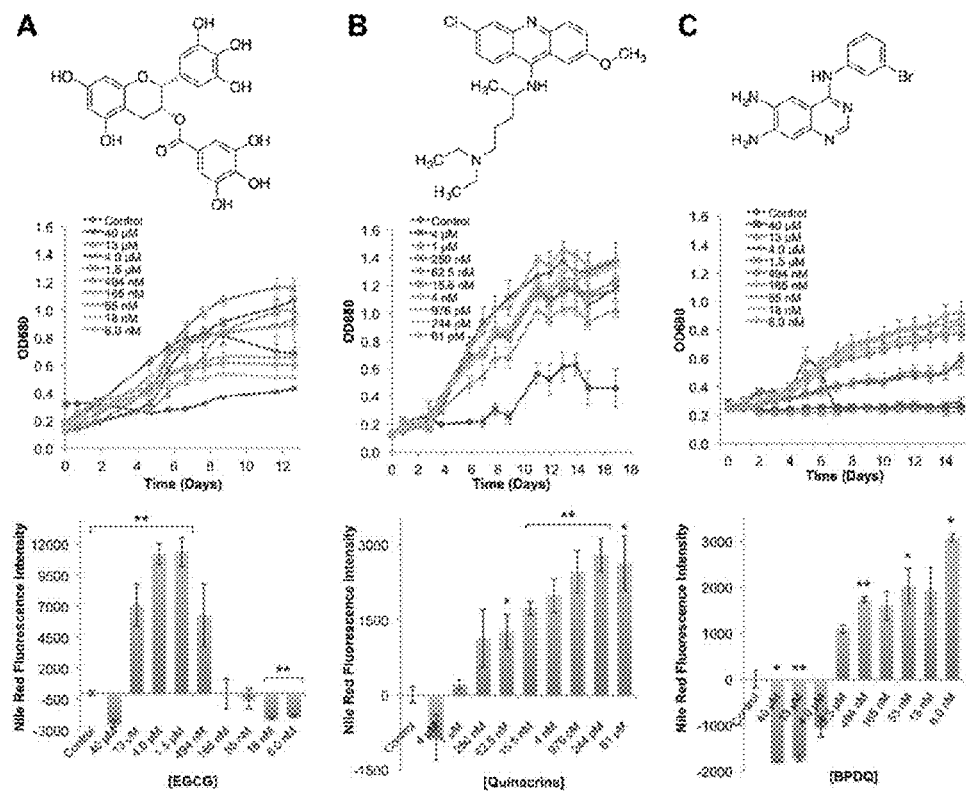
FIG. 20 depicts dose-response effects for microalgae biomass concentration and intracellular lipid levels in microplates. Intracellular lipid levels measured by Nile Red fluorescence on day 3 of stationary phase, which differs for each microalgae strain.
Figure 21:
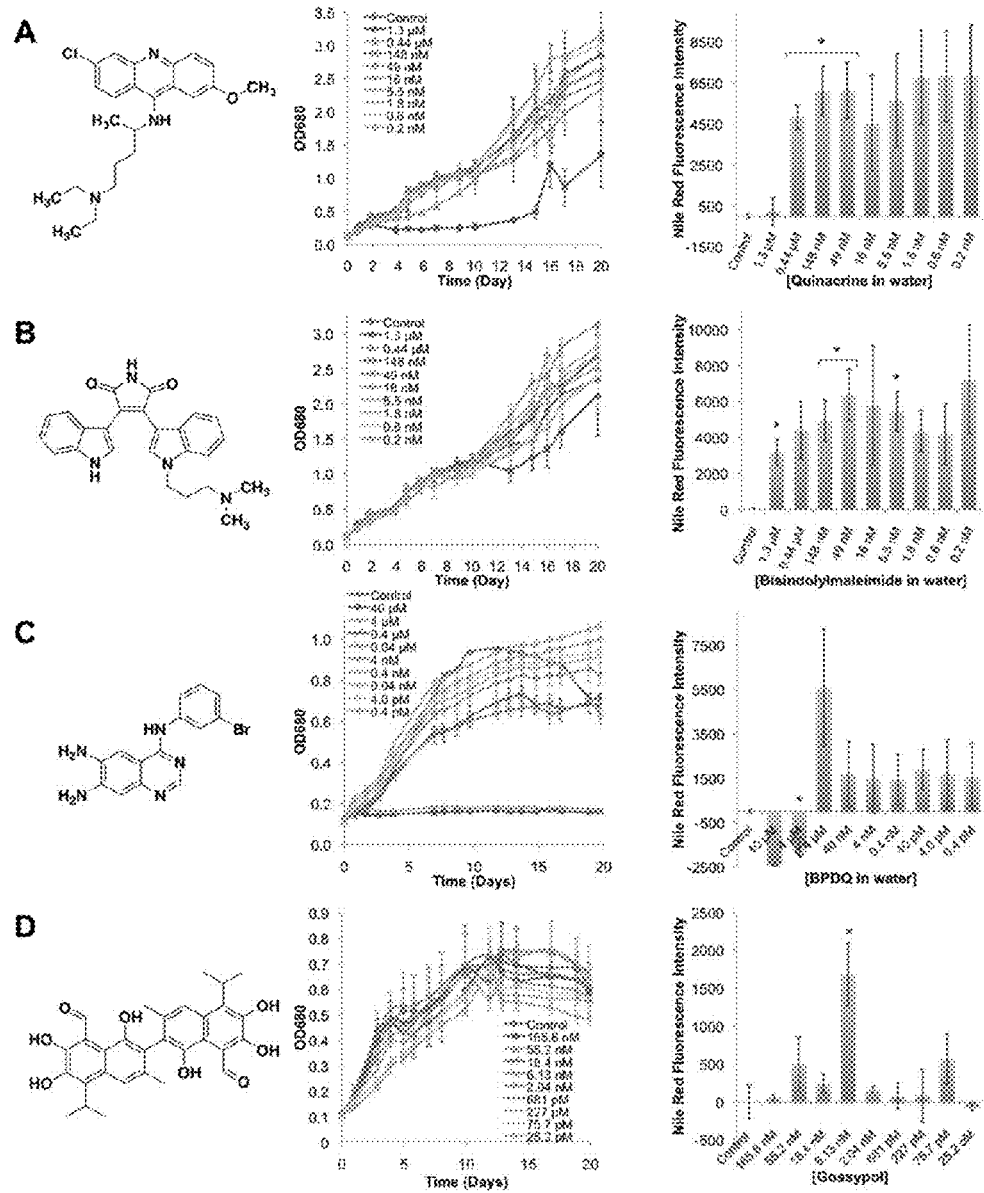
FIG. 21 depicts the dose-response effects for growth rate and intracellular lipid levels in microalgae.

From this dose-response microplate screening based on Nile red fluorescence intensity, we identified twelve compound/strain combinations that increased intracellular lipid levels by more than 100%, with epigallocatechin gallate, CDK2 inhibitor 2, and cycloheximide resulting in an increase in intracellular lipids of 200-400% (Table 28). Many compounds showed activity in microalgae at nanomolar concentrations and several showed activity in multiple microalgae strains (Table 28). For example, quinacrine, an NF-κB inhibitor and p53 activator, increased intracellular lipids by over 100% compared to the control (based on Nile red fluorescence intensity) in N. oculata and Nannochloris sp. (in water). Additionally, (−)-epigallocatechin gallate (EGCG), a catechin found in green tea, also showed intracellular lipid increases of over 100% at several concentrations. FIG. 20 shows examples of dose-response screening results for cell growth and intracellular lipid measurements for (−)-epigallocatechin gallate, quinacrine, and BPDQ, in N. salina, N. oculata and N. salina, respectively. FIG. 21 shows additional examples of dose-response screening results for cell growth and intracellular lipid measurements for quinacrine in water, bisindolylmaleimide in water, BPDQ in water, and gossypol. In cases where compounds exhibited nanomolar activity for effects on growth or intracellular lipid levels, additional concentration ranges were evaluated to determine the most promising concentrations for testing in larger batch culture experiments. A summary of microalgae species and concentrations of lead compounds exhibiting the greatest effect on lipid levels is provided in Tables 28 and 29. The basic trends observed for dose-response screening followed the examples shown in FIGS. 20 and 21. Table 28 shows a summary of compounds affording >50% increase of intracellular lipid levels in microplate dose-response screening relative to DMSO control ($p<0.05$).

TABLE 28

| Microalgae | Compound[b] | Concentration | % Lipid increase based on Nile red fluorescence intensity |
|---|---|---|---|
| N. oculata | Baicalein | 25.2 pM | 52 |
| | Baicalein (water) | 40 µM | 76 |
| | Curcumin | 75.7 pM | 49 |
| | Quinacrine | 244 nM | 106 |
| | SB202190[c] | 400 fM | 95 |
| N. salina | Arctigenin | 370.4 nM | 64 |
| | Atrazine | 4.6 nM | 53 |
| | BPDQ | 6.0 | 130 |
| | CDK4 inhibitor I | 40 µM | 49 |
| | Epigallocatechin gallate | 1.48 µM | 217 |
| | Esculetin | 6.13 nM | 62 |
| | Forskolin | 4.6 nM | 66 |
| | Gossypol | 6.13 nM | 103 |
| | Indomethacin | 123.5 nM | 61 |
| | JZL 184 hydrate | 40 µM | 119 |
| | Methyl jasmonate | 13 nM | 85 |
| | PTP inhibitor II | 22.7 pM | 54 |
| | Zeatin | 4.6 nM | 64 |
| Nannochloris sp. | Bisindolylmaleimide (water) | 49 nM | 141 |
| | FAAH inhibitor I (water) | 0.6 nM | 189 |
| | FAAH inhibitor II (water) | 0.6 nM | 182 |
| | Indomethacin (water) | 5.5 nM | 95 |
| | Ketoconazole (water) | 148 nM | 94 |
| | Piceatannol | 6.10 nM | 71 |
| | Quinacrine (water) | 49 nM | 136 |
| P. tricornutum | Arctigenin | 41.2 nM | 61 |
| | BPDQ (water) | 400 fM | 63 |
| | Caffeic acid (water) | 4 µM | 94 |
| | cAMP | 370.4 nM | 66 |
| | CDK2 inhibitor 2 | 40 µM | 347 |
| | CDK4/6 I4 | 10 µM | 50 |
| | Cycloheximide[c] | 400 nM | 408 |
| | Naphthyl acid phosphate (water) | 681 pM | 51 |
| | Resveratrol | 10 nM | 61 |
| | Zeatin | 4.6 nM | 114 |

In Table 28, "a" refers to increases in Nile Red fluorescence intensity were based on three or more replicates with $p \leq 0.05$. Depending on the experiment, replicates were tested in different 96-well microplates or within the same microplate. The p-values were calculated utilizing a two-tailed independent t-test. In Table 28, "b" refers to Solutions of DMSO are used for compound delivery, except for cases where water is indicated in parenthesis. Compounds were added at the start of analysis on t=day 0. In Table 28, "c" indicates a compound that was added at exponential phase, t=day 7.

Table 29 lists compounds from the dose-response microplate screening that exhibit Nile Red fluorescence increases approximately ≥50% ($p<0.05$). In Table 29, increases in Nile Red fluorescence intensity were based on three replicates with $p<0.05$ and were analyzed in three different 96-well microplates with the exception of the few compounds. P-values were calculated utilizing a two-tailed test. A lower p-value cutoff was observed for compounds noted by * exhibiting $p<0.001$,  $p<0.0001$, and * $p<0.00001$. Compounds with water listed in parenthesis indicate that the compound was dissolved in water for delivery, instead of DMSO. All compounds were added initially (t=day 0). In Table 29, "a" refers to analysis of four replicates within the same plate; "b"

refers to analysis of four replicates within different plates; "c" refers to analysis of six replicates within the same plates; and "d" refers to compounds that were added during exponential phase, at approximately eight days

TABLE 29

| Microalgae Strain | Compound | Concentration | % Increase based on Nile Red Fluorescence Intensity |
|---|---|---|---|
| N. oculata | Quinacrine[a] | 244 pM | 106 |
| | Quinacrine[a] | 61 pM | 100 |
| | Sb202190[d] | 400 fM | 95 |
| | Quinacrine[a] | 976 pM | 93 |
| | Baicalein (water)*** | 40 μM | 76 |
| | Quinacrine[a] | 4 nM | 75 |
| | Quinacrine*[a] | 15.6 nM | 66 |
| | Baicalein | 25.2 pM | 52 |
| | Curcumin | 75.7 pM | 49 |
| N. salina | Epigallocatechin gallate*[c] | 1.48 μM | 217 |
| | Epigallocatechin gallate**[c] | 4.44 μM | 214 |
| | Epigallocatechin gallate[c] | 13.3 μM | 136 |
| | BPDQ | 6.0 nM | 130 |
| | JZL 184 hydrate[b] | 40 μM | 119 |
| | Gossypol | 6.13 nM | 103 |
| | Epigallocatechin gallate[c] | 493 nM | 87 |
| | BPDQ | 55 nM | 86 |
| | Methyl jasmonate | 13 nM | 85 |
| | BPDQ | 494 nM | 73 |
| | Forskolin | 4.6 nM | 66 |
| | Zeatin*** | 4.6 nM | 64 |
| | Arctigenin** | 370.4 nM | 64 |
| | BPDQ | 6.10 nM | 63 |
| | Arctigenin* | 4.6 nM | 63 |
| | Esculetin | 6.13 nM | 62 |
| | Indomethacin | 123.5 nM | 61 |
| | Arctigenin | 13 nM | 59 |
| | PTP Inhibitor II | 227 pM | 54 |
| | Atrazine | 4.6 nM | 53 |
| | Zeatin | 13 nM | 50 |
| | Esculetin | 681 pM | 50 |
| | CDK4 inhibitor 1 | 40 μM | 49 |
| | Kinetin* | 4.6 nM | 48 |
| Nannochloris sp. | FAAH inhibitor I (water) | 0.6 nM | 189 |
| | FAAH inhibitor I (water) | 5.5 nM | 188 |
| | FAAH inhibitor I (water) | 1.8 nM | 187 |
| | FAAH inhibitor II (water) | 0.6 nM | 182 |
| | FAAH inhibitor II (water) | 148 nM | 167 |
| | FAAH inhibitor I (water) | 440 nM | 161 |
| | FAAH inhibitor I (water) | 49 nM | 160 |
| | FAAH inhibitor II (water) | 49 nM | 154 |
| | FAAH inhibitor I (water) | 1.3 μM | 152 |
| | FAAH inhibitor II (water) | 0.2 nM | 145 |
| | FAAH inhibitor II (water) | 1.3 μM | 144 |
| | Bisindolylmaleimide (water) | 49 nM | 141 |
| | Quinacrine (water) | 49 nM | 136 |
| | Quinacrine (water) | 49 nM | 136 |
| | Quinacrine (water) | 148 nM | 135 |
| | Quinacrine (water) | 148 nM | 135 |
| | Bisindolylmaleimide (water) | 5.5 nM | 121 |
| | Bisindolylmaleimide (water) | 148 nM | 109 |
| | Quinacrine (water) | 440 nM | 106 |
| | Quinacrine (water) | 440 nM | 106 |
| | Indomethacin (water) | 5.5 nM | 95 |
| | Ketoconazole (water) | 148 nM | 94 |
| | Indomethacin (water) | 49 nM | 81 |
| | Piceatannol | 6.1 nM | 71 |
| | Bisindolylmaleimide (water) | 1.3 μM | 70 |
| P. tricornutum | Cycloheximide[d] | 400 nM | 408 |
| | CDK2 inhibitor 2 | 40 μM | 347 |
| | Zeatin | 4.6 nM | 114 |
| | Caffeic acid (water) | 4 μM | 94 |
| | CDK2 inhibitor 2*** | 10 μM | 86 |
| | cAMP | 370.4 nM | 66 |
| | BPDQ (water) | 400 fM | 63 |
| | Resveratrol | 10 nM | 61 |
| | Arctigenin | 41.2 nM | 61 |
| | Naphthyl acid phosphate (water) | 681 pM | 51 |
| | CDK4/6 inhibitor 4*** | 10 μM | 50 |

We also demonstrated the importance of temporal effects for small molecule screening by adding compounds at different microalgae growth phases (e.g., initial vs. exponential phase), an option that is not typically available when gene function is disrupted using classical genetic manipulation. Initial compound screening was performed with compounds added to the microplate before the start of the assay (i.e., at t=0). A second round of microplate screening was performed where microalgae cultures were treated with lead compounds during the exponential phase of growth (t=day 7) to evaluate potential temporal effects. Small molecules that demonstrated growth-inhibitory properties when added at t=0 were of particular interest to evaluate temporal effects, because it was believed that these compounds would mimic nutrient-limiting stress conditions and shift the metabolic pathways to increase lipid levels without having detrimental growth effects as a result of being introduced later in the growth cycle. The results are shown in FIG. 22.

Figure 22:
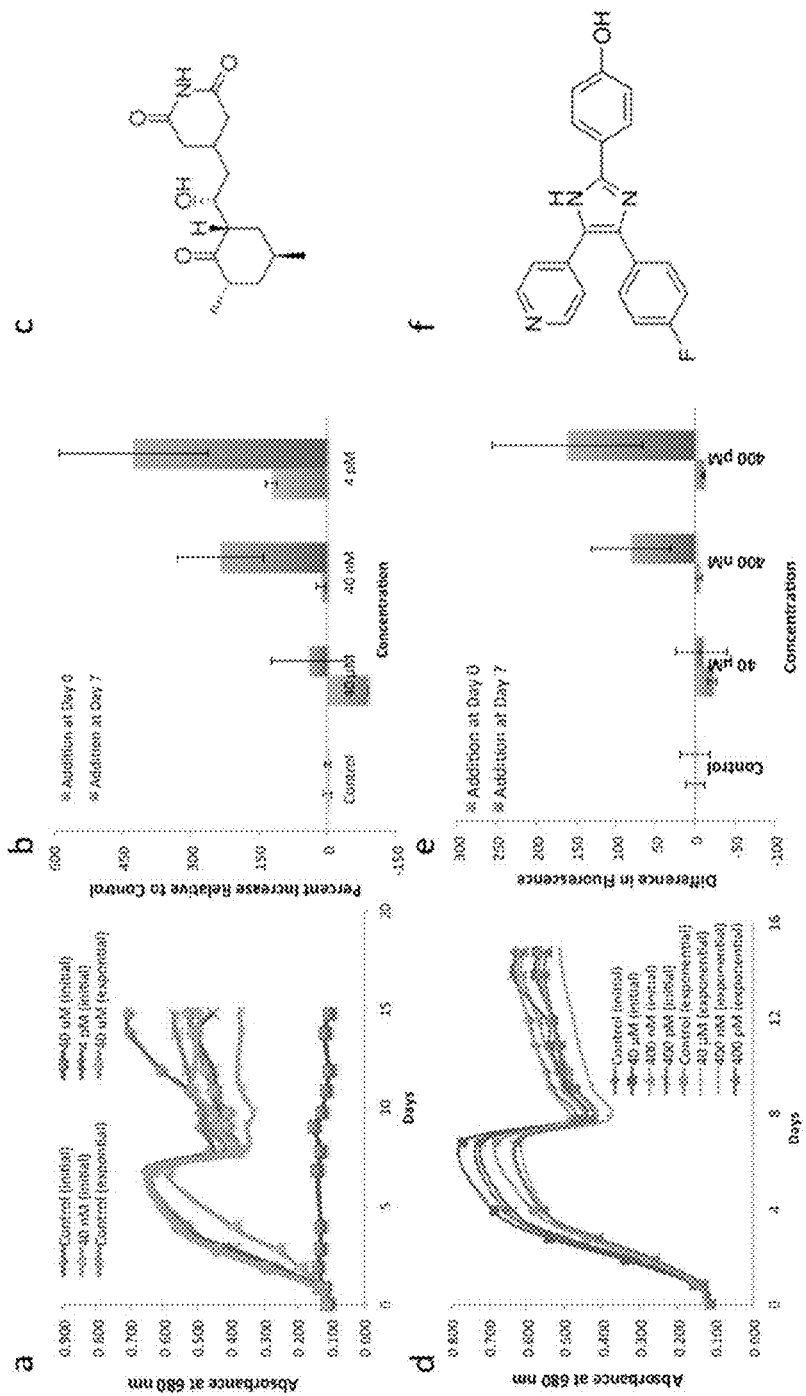
FIG. 22 depicts Examples of temporal effects for cycloheximide and SB202190 screened in *P. tricornutum*.

The temporal effects for cycloheximide, a protein synthesis inhibitor, and SB202190, a MAP38 kinase inhibitor, were particularly noteworthy (FIG. 22). When microalgae cells were treated with cycloheximide in the initial phase at concentrations greater than 1 µM, an inhibitory effect on cell growth was observed (based on low absorbance compared to control in all four species) and only a minimal increase in lipid levels was observed (FIG. 22*a*). However, when cycloheximide was added during the exponential growth phase, an increase in lipid levels up to 400% was observed over a greater concentration range for *P. tricornutum* (FIG. 22*a*). The addition of SB202190 in exponential growth phase also afforded a more significant increase in the intracellular lipid levels for *N. oculata*, where an increase from 45% to 95% was observed based on Nile Red fluorescence intensity at >0.040 nM concentrations (FIG. 22*d*). Without wishing to be bound by theory, it is believed that these results not only highlight the potential impact of performing compound treatment at various growth phases, but also shows that comparing temporal effects may assist in elucidating the mechanism of action for a compound.

Use of Chemical Triggers to Increase Lipid Levels in Larger Cultures

Based on the above dose-response screening results, candidate compound/strain combinations were selected for screening in 500-mL batch cultures to confirm their effectiveness in the context of larger scale microalgae batch cultures where lipid extracts can be quantified using gravimetric analysis. Selection of compound/strain combinations was based on demonstrated increases in lipid levels of over 50% based on Nile Red fluorescence intensity (p-value <0.05) in dose-response screening, or if positive results were observed in more than one microalgae species. With this size culture, secondary assays were also performed to analyze lipid composition using $^1$H NMR spectroscopy, matrix assisted laser desorption ionization time-of-flight mass spectrometry (MALDI-TOF), and GC/MS. Batch culture screening was performed with the four microalgae strains, but the most significant effects of compounds on lipid production were observed in the green microalgae strains, highlighted in Table 30. Compared to microplates, microalgae grown in batch cultures are aerated, mixed, and exposed to light and other contaminating organisms more similarly to bioreactors or outside growth ponds used for industrial microalgae production, which makes them more representative to predict success in industrial applications.

Table 30 lists results of chemical triggers on lipid productivity in microalgae in 500 mL cultures. In Table 30 "a" refers to a comparison of dry weight and lipid extracts for 500-mL microalgae cultures treated with bioactive small molecules vs. control cultures with and without DMSO. All cultures were performed with three or more replicates unless otherwise indicated. In Table 30, "b" refers to specific growth rate that was calculated during mid-exponential growth phase. In Table 30, "c" refers to lipid content that was determined with dried lipid extract and dry biomass. All data indicates the average with the standard deviation denoted. Standard deviation was calculated from within individual batch culture sets. Due to small cell size, *Nannochloris* sp. samples were not fully dried, therefore, the w/w analysis of lipid content was not directly calculated. In Table 30, "d" refers to the change in lipid that was calculated based on gravimetric analysis relative to the averaged control without DMSO. In Table 30, "e" refers to compound treatments where two replicates performed.

TABLE 30

| Microalgae | Compound | Specific Growth Rate (days$^{-1}$)[b] | Lipid content (% w/w)[c] | Lipid productivity (mgL$^{-1}$day$^{-1}$) | Change in Lipids (%)[d] |
|---|---|---|---|---|---|
| *Nannochloris* sp. | Control | 0.17 ± 0.03 | — | 3.0 ± 0.9 | — |
|  | DMSO (0.4%) | 0.21 ± 0.11 | — | 2.6 ± 0.2 | −16 |
|  | 10 µM Forskolin | 0.15 ± 0.05 | — | 4.5 ± 1.7 | 51 |
|  | 400 nM cAMP | 0.17 ± 0.01 | — | 4.8 ± 0.5 | 62 |
|  | 40 nM Quinacrine | 0.18 ± 0.01 | — | 4.2 ± 1.1 | 31 |
|  | 40 nM Orlistat | 0.20 ± 0.01 | — | 5.1 ± 1.5 | 72 |
|  | 40 nM EGCG | 0.17 ± 0.03 | — | 4.3 ± 0.8 | 39 |
|  | 4 nM SB202190 | 0.17 ± 0.02 | — | 3.0 ± 1.7 | 3 |
|  | 4 nM SB202190 (exponential addition) | 0.15 ± 0.08 | — | 4.0 ± 1.6 | 38 |
| *N. oculata* | Control | 0.16 ± 0.04 | 16.1 ± 6.6 | 3.5 ± 0.7 | — |
|  | DMSO (0.4%) | 0.20 ± 0.07 | 18.6 ± 7.8 | 4.8 ± 0.6 | 39 |
|  | 4 nM Forskolin | 0.17 ± 0.02 | 25.6 ± 1.8 | 6.4 ± 1.2 | 84 |
|  | 400 nM cAMP | 0.19 ± 0.03 | 22.3 ± 11.0 | 4.4 ± 1.8 | 51 |
|  | 400 nM Quinacrine | 0.18 ± 0.04 | 16.7 ± 4.9 | 5.2 ± 0.6 | 51 |
|  | 4 µM EGCG | 0.17 ± 0.03 | 20.6 ± 6.9 | 4.9 ± 1.7 | 41 |

TABLE 30-continued

| Microalgae | Compound | Specific Growth Rate (days$^{-1}$)[b] | Lipid content (% w/w)[c] | Lipid productivity (mgL$^{-1}$day$^{-1}$) | Change in Lipids (%)[d] |
|---|---|---|---|---|---|
| N. salina | Control | 0.23 ± 0.06 | 23.6 ± 9.0 | 4.7 ± 1.4 | — |
| | DMSO (0.4%) | 0.26 ± 0.07 | 24.3 ± 7.5 | 6.5 ± 1.7 | 25 |
| | 4 µM cAMP | 0.22 ± 0.03 | 28.6 ± 10.7 | 7.9 ± 3.4 | 46 |
| | 40 nM Quinacrine | 0.25 ± 0.02 | 26.5 ± 3.9 | 4.5 ± 1.0 | 6 |
| | 40 µM EGCG | 0.22 ± 0.06 | 23.1 ± 10.6 | 6.3 ± 2.2 | 18 |
| | 4 µM EGCG (in water)[e] | 0.24 ± 0.01 | 32.4 ± 0.1 | 7.1 ± 1.2 | 46 |
| | 40 nM propyl gallate | 0.23 ± 0.002 | 25.9 ± 11.4 | 8.3 ± 1.7 | 67 |
| | 4 nM BHA | 0.23 ± 0.002 | 28.8 ± 11.4 | 8.1 ± 0.6 | 63 |
| P. tricornutum | Control | 0.27 ± 0.09 | 15.6 ± 6.1 | 3.9 ± 1.7 | — |
| | DMSO (0.4%) | 0.27 ± 0.08 | 21.5 ± 5.9 | 4.1 ± 1.6 | −1 |
| | 76 pM Gossypol | 0.21 ± 0.05 | 24.4 ± 2.7 | 5.6 ± 1.9 | 27 |
| | 40 nM cAMP | 0.26 ± 0.19 | 16.7 ± 0.7 | 5.3 ± 1.0 | 28 |
| | 120 nM AICAR | 0.34 ± 0.04 | 22.7 ± 1.3 | 7.0 ± 0.9 | 45 |
| | 4 µM EGCG (in water)[e] | 0.19 ± 0.02 | 17.2 ± 1.3 | 4.4 ± 2.4 | 6 |

As shown in Table 30, positive increases in growth and lipid levels (based on cell density, biomass and gravimetric analysis on neutral lipids extracts) were identified with bioactive molecules forskolin, cAMP, quinacrine, orlistat, and EGCG. Most compounds were effective when added at the beginning of the culture growth, but SB202190 resulted in a 38% increase in lipid levels in *Nannochloris* sp. batch culture only when added during the exponential growth phase. This result was expected based on the temporal screening experiments in microplates (FIG. 22).

Figure 23:
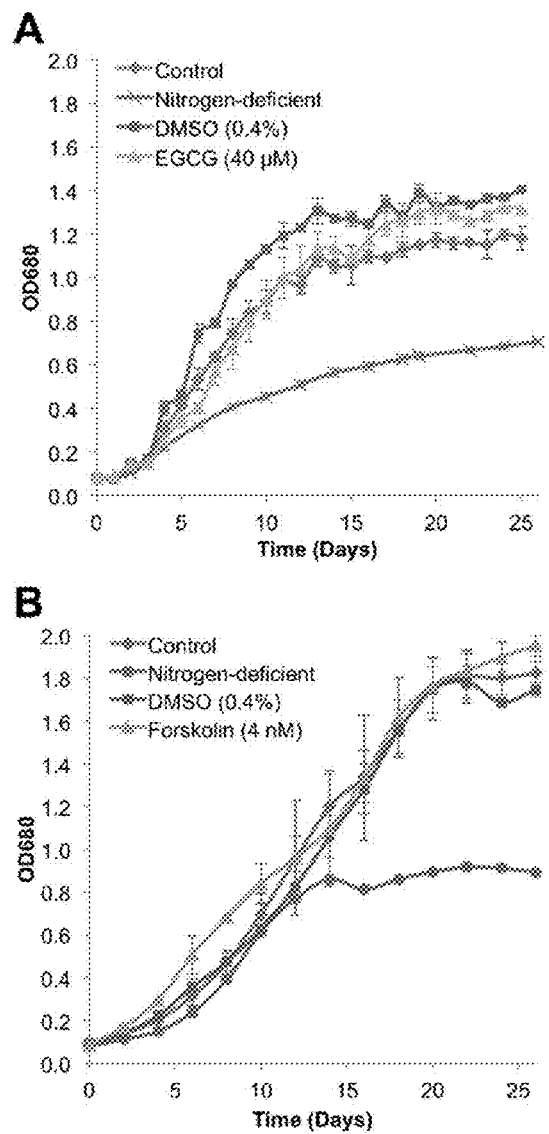
FIG. 23A depicts a comparison of microalgae growth for trigger-induced and nitrogen-deficient conditions in 500-mL batch cultures for *N. salina*.
FIG. 23B depicts a comparison of microalgae growth for trigger-induced and nitrogen-deficient conditions in 500-mL batch cultures for *N. oculata*. Data points represent the mean of replicates with error bars (s.e.m.) For FIG. 23A, the control had 6 replicates, the DMSO (0.4%) had 5 replicates, the EGCG 40 μM had 4 replictes, and the nitrogen deficient condition had 2 replicates. For FIG. 23B, the control had 4 replicates, the DMSO (0.4%) had 3 replicates, the EGCG 40 μM had 4 replictes, the nitrogen deficient condition had 2 replicates, and the forskolin (4 nM) had 2 replicates. Polynomial line fitting applied.

Forskolin and cAMP were selected based on their known activity as protein kinase activators, with forskolin known to increase cAMP levels and cause lipolysis (38). After confirming positive preliminary results for forskolin in the initial microplate screening, both forskolin and cAMP were tested in parallel with batch culture experiments (Table 30). In batch cultures, forskolin led to an 84% increases in lipid levels in *N. oculata*, and a 51% increase in *Nannochloris* sp. (Table 30). cAMP also increased lipid levels by 28-62%, depending on the microalgae strain (Table 30). Quinacrine, a known inhibitor of PLA$_2$ and NF-κB and an activator of p53, showed moderate lipid increase activity in *Nannochloris* sp. (31%) and *N. oculata* (51%). It is notable that these cultures maintain or increase growth (i.e., cell density) while maintaining lipid production (FIG. 23). The fact that growth is maintained in the presence of these chemical triggers is in contrast to the effects observed and reported under nitrogen-deficient conditions, which are often utilized as a model system to study increased lipid productivity (3). Nitrogen-deficient conditions are known to reduce cell division while increasing overall lipid productivity per cell compared to normal growth conditions (5, 8).

As shown in FIG. 23, the chemical triggers EGCG and forskolin achieve the goal of increasing overall levels of lipids without inducing a decrease in cell growth. $^1$H NMR spectroscopy, MALDI-TOF and GC/MS analysis of the lipid composition for compound-treated cultures indicated that there was no significant change in fatty acid profiles. Without wishing to be bound by theory, it is believed that these results indicate that synergistic screening of compounds using nitrogen-deficient growth conditions may provide additional opportunities to increase lipid levels with this small molecule activation strategy. Without wishing to be bound by theory, it is also believed that the synergistic effects of sodium bicarbonate in addition to chemical triggers may partially account for the difference between results observed for microplate and batch culture lipid levels.

Effects of DMSO as Delivery Vehicle

Based on the above results, the use of DMSO as a compound delivery vehicle was generally determined to be important for compound effects, most notably in the green microalgae strains, which are known to have thick cell walls (30). DMSO was utilized based on its ability to promote the permeation of solutes, as well as the solubility of the majority of bioactive compounds in it (39, 40). DMSO is also known to be a versatile molecule with cryoprotective (41), antioxidant (42), and lipid enhancing properties (43). DMSO is known to be naturally occurring in microalgae (44) and originates from the enzymatic cleavage product of dimethylsulfoniopropri-onate (DMSP) and dimethyl sulfide (DMS). In microalgae species such as *Thalassiosira pseudonana*, DMSP serves as an antioxidant and cryoprotectant (45).

While all preliminary compound screening was performed with DMSO stock solutions (with a final volume of 0.4% per culture), lead compounds were also screened with water as a delivery vehicle to determine if the DMSO was contributing to the observed effects. In the green microalgae strains, using water as a delivery agent for compounds often led to minimal effects (<40% increase) on the lipid levels (Tables 28-30). These results indicated that the DMSO is essential to facilitate the entry of the compound into the cell, or to enhance the effect of the chemical trigger. This was not the case with EGCG, which showed similar effects in *N. salina* when screening either with water or with DMSO (Table 30). This result indicated that the need for DMSO may be dependent on either the compound or the microalgae strain. In the specific case with the diatom *P. tricornutum*, the use of water as a delivery agent resulted in an increase in the potency of several compounds (Tables 28-30). Without wishing to be bound by theory, it is believed that the results with *P. tricornutum* were attributed to an enhanced sensitivity of the diatom to DMSO.

DMSO was independently screened in microplates at concentrations from 0-1.4% (v/v) to determine how the vehicle affected microalgae growth and intracellular lipid levels. At less than 0.4% v/v DMSO did not show a toxic or detrimental effect on the growth for any of the four microalgae strains tested (39, 46). With the addition of higher levels of DMSO (e.g. >0.8% v/v) a more substantial and detrimental effect on growth and cell density was observed for *N. oculata* and *N. salina*. Upon comparison of batch culture control experiments for DMSO (at 0.4% v/v), we observed a 39% increase in lipid levels with *N. oculata* and a 25% increase in lipid levels with *N. salina* (Table 30). In *P. tricornutum* or *Nan-*

*nochloris* sp., the addition of 0.4% v/v DMSO generally showed no effect, or a small decrease in growth and lipid production (Table 30).

Effects of Antioxidant Molecules

In all green microalgae strains, we observed that nanomolar or micromolar concentrations of EGCG increased growth and lipid extract levels (Table 30). In the case of *N. salina*, this result was consistent when the compound was delivered using either DMSO or water as the vehicle (Table 30). Various biological effects have been reported for EGCG, including inhibition of fatty acid synthase, α-glucosidase and MAP kinase-mediated signaling pathways (47, 48). Furthermore and without wishing to be bound by theory, we believe that the antioxidant action of EGCG may protect cells from lipid peroxidation (49), which may be involved in modulating photooxidative stress pathways and could therefore reduce photooxidative stress and enhance photosynthetic efficiency (50, 51). Although some information is known in plants, the effects of oxidative stress and the connection to lipid production are poorly understood in microalgae (52).

Without wishing to be bound by theory, we believe that antioxidants such as EGCG may serve as an oxidative signaling molecule to enhance photoprotection, and thus may provide a new pathway for increasing lipid production. To test this, we determined the effects of several additional molecules with known antioxidant properties, with a particular focus on readily-available derivatives and molecules already used in industrial applications, such as butylated hydroxyanisole (BHA), a preservative used in packaged foods.

We first evaluated a series of antioxidants in microplate assays to identify optimal concentration ranges (Tables 28-29), and then moved to larger batch culture experiments (Table 30). In batch cultures with *N. salina*, both BHA (4 nM) and propyl gallate (40 nM), a simplified derivative of the EGCG structure, showed positive results with increases in intracellular lipid levels (Table 30). In particular, BHA showed a 63% increase in lipid levels, while propyl gallate showed a 67% increase in lipid levels (Table 30).

In conclusion, we have demonstrated an example of chemical genetic phenotypic screening with microalgae and have identified several molecules that increase growth and lipid levels at nM and μM concentrations. In order to optimize microalgae lipid production to make algal biodiesel more cost-effective, the ideal conditions will increase the amount of lipid produced per cell while the cell density per culture is simultaneously increased. An increase in lipids, whether by increasing lipid per cell or overall increase in biomass, demonstrates how overall lipid yield can be increased by using a small molecule in nanomolar concentration. Using a novel approach to accomplish this goal, we have demonstrated that chemical genetics and phenotypic screening can be used to identify chemical triggers of signaling pathways relevant to increase cell density or lipid levels in several oleaginous microalgae relevant for biofuel feedstock (3). Our results here confirm that the small molecules forskolin, quinacrine, BPDQ, and EGCG provide useful modulators to study lipid pathways, as an alternative to the use of nitrogen-deficient conditions. Without wishing to be bound by theory, it is believed that these results may lead to the development of chemical triggers to increase biomass and lipid production. Our results showing up to an 85% increase in lipid levels in batch cultures represents a significant advance for industrially-relevant strains.

Without wishing to be bound by theory, it is believed that due to the intimacy of the carbon metabolism and photooxidative stress along with the redox signal transduction mechanism that regulates carbon metabolism, oxidative signaling molecules, such as antioxidants and kinase activators/inhibitors may be used to control and improve cell growth while also increasing lipid levels. The results of testing compound effects across multiple microalgae strains indicates that these molecules may be useful as new probes for lipid synthesis and metabolism, and facilitate the identification of conserved protein targets for genetic engineering. Without wishing to be bound by theory, it is believed that by understanding and controlling lipid-producing pathways, the enhanced production of triacylglycerols from microalgae may make algae-derived biofuels an economically-feasible liquid fuel option. While the direct mode of action for these known bioactive molecules remains to be confirmed in microalgae, the above results demonstrate the power of using small molecules to modulate microalgae pathways and show significant promising results for commercial applications (54).

References For Examples 1 and 2

1 Sheehan, J., Dunahay, T., Benemann, J. & Roessler, P. A look back at the US department of energy's aquatic species program—Biodiesel from Algae. *National Renewable Energy Laboratory*, 328 (1998).
2 Huang, G., Chen, F., Wei, D., Zhang, X. & Chen, G. Biodiesel production by microalgal biotechnology. *Applied Energy*, 1-9, doi:10.1016/j.apenergy.2009.06.016 (2009).
3 Rodolfi, L. et al. Microalgae for oil: Strain selection, induction of lipid synthesis and outdoor mass cultivation in a low-cost photobioreactor. *Biotechnol. Bioeng.* 102, 100-112, doi:10.1002/bit.22033 (2009).
4 Hu, Q. et al. Microalgal triacylglycerols as feedstocks for biofuel production: perspectives and advances. *Plant J* 54, 621-639, doi:10.1111/j.1365-313x.2008.03492.x (2008).
5 Spolaore, P., Joannis-Cassan, C., Duran, E. & Isambert, A. Commercial applications of microalgae. *J. Biosci. Bioeng.* 101, 87-96, doi:10.1263/jbb.101.87 (2006).
6 Song, D., Fu, J. & Shi, D. Exploitation of oil-bearing microalgae for biodiesel. *Chin J Biotechnol* 24, 341-348, doi:10.1016/S1872-2075(08)60016-3 (2008).
7 Chisti, Y. Biodiesel from microalgae. *Biotechnol. Adv.* 25, 294-306, doi:10.1016/j.biotechadv.2007.02.001 (2007).
8 Chisti, Y. Biodiesel from microalgae beats bioethanol. *Trends Biotechnol.* 26, 126-131, doi:10.1016/j.tibtech.2007.12.002 (2008).
9 James, G. O. et al. Fatty acid profiling of *Chlamydomonas reinhardtii* under nitrogen deprivation. *Bioresour. Technol.* 102, 3343-3351, doi:10.1016/j.biortech.2010.11.051 (2011).
10 Wang, Z. T., Ullrich, N., Joo, S., Waffenschmidt, S. & Goodenough, U. Algal Lipid Bodies: Stress Induction, Purification, and Biochemical Characterization in Wild-Type and Starchless *Chlamydomonas reinhardtii*. *Eukaryotic Cell* 8, 1856-1868, doi:10.1128/EC.00272-09 (2009).
11 Lamers, P. P. et al. Carotenoid and fatty acid metabolism in light-stressed *Dunaliella salina*. *Biotechnol. Bioeng.*, n/a-n/a, doi:10.1002/bit.22725 (2010).
12 Richardson, B., Orcutt, D., Schwertner, H., Martinez, C. & Wickline, H. Effects of nitrogen limitation on the growth and composition of unicellular algae in continuous culture. *Applied and Environmental Microbiology* 18, 245-250 (1969).
13 Suen, Y., Hubbard, J. S., Holzer, G. & Tornabene, T. G. Total lipid production of the green alga *Nannochloropsis* sp. qII under different nitrogen regimes. *J Phycol* 23, 289-296, doi:10.1111/j.1529-8817.1987.tb04137.x (1987).

14. Zhila, N. O., Kalacheva, G. S. & Volova, T. G. Influence of nitrogen deficiency on biochemical composition of the green alga Botryococcus. *J. Appl. Phycol.* 17, 309-315, doi:10.1007/s10811-005-7212-x (2005).
15. Siaut, M., Cuine, S., Cagnon, C., Fessler, B., Nguyen, M., Carrier, P., Beyly, A., Beisson, F., Triantaphylides, C., Li-Beisson, Y. & Peltier, G. Oil accumulation in the model green alga Chlamydomonas reinhardtii: characterization, variability between common laboratory strains and relationship with starch reserves. *BMC Biotechnology* 11, 7 (2011).
16. Li, Y., Han, D., Hu, G., Sommerfeld, M. & Hu, Q. Inhibition of starch synthesis results in overproduction of lipids in Chlamydomonas reinhardtii. *Biotechnol. Bioeng.* 107, 258-268, doi:10.1002/bit.22807 (2010).
17. Schreiber, S. L. Small molecules: the missing link in the central dogma. *Nat Chem Biol* 1, 64-66 (2005).
18. Walsh, D. P. & Chang, Y.-T. Chemical Genetics. *Chem. Rev.* 106, 2476-2530, doi:10.1021/cr0404141 (2006).
19. Stockwell, B. R. Exploring biology with small organic molecules. *Nature* 432, 846-854 (2004).
20. Blackwell, H. E. & Zhao, Y. Chemical Genetic Approaches to Plant Biology. *Plant Physiol.* 133, 448-455, doi: 10.1104/pp. 103.031138 (2003).
21. Lehár, J., Stockwell, B. R., Giaever, G. & Nislow, C. Combination chemical genetics. *Nat Chem Biol* 4, 674-681, doi:10.1038/nchembio.120 (2008).
22. Chen, W., Zhang, C., Song, L., Sommerfeld, M. & Hu, Q. A high throughput Nile red method for quantitative measurement of neutral lipids in microalgae. *J. Microbiol. Methods* 77, 41-47, doi:10.1016/j.mimet.2009.01.001 (2009).
23. Danielewicz, M. A., Anderson, L. A. & Franz, A. K. Triacylglycerol profiling of marine microalgae by mass spectrometry. *J. Lipid Res.* 52, 2101-2108, doi:10.1194/jlr.D018408 (2011).
24. Knothe, G. & Kenar, J. A. Comment on "Biodiesel Production from Freshwater Algae". *Energy Fuels* 24, 3299-3300, doi:10.1021/ef100356e (2010).
25. Knothe, G. Improving biodiesel fuel properties by modifying fatty ester composition. *Energy & Environmental Science* 2, 759-766 (2009).
26. Burns, A. R. et al. High-throughput screening of small molecules for bioactivity and target identification in Caenorhabditis elegans. *Nat. Protocols* 1, 1906-1914 (2006).
27. Hadvary, P., Lengsfeld, H. & Wolfer, H. Inhibition of pancreatic lipase in vitro by the covalent inhibitor tetrahydrolipstatin. *Biochem. J.* 256, 357-361 (1988).
28. Sutherland, C. A. & Amin, D. Relative activities of rat and dog platelet phospholipase A2 and diglyceride lipase. Selective inhibition of diglyceride lipase by RHC 80267. *Journal of Biological Chemistry* 257, 14006-14010 (1982).
29. Long, J. Z. et al. Selective blockade of 2-arachidonoylglycerol hydrolysis produces cannabinoid behavioral effects. *Nat Chem Biol* 5, 37-44, 2009.
30. Conde-Frieboes, K. et al. Activated Ketones as Inhibitors of Intracellular Ca2+-Dependent and Ca2+-Independent Phospholipase A2. *Journal of the American Chemical Society* 118, 5519-5525, doi:10.1021/ja953553w (1996).
31. Loonen, A. J. M., Soe-Agnie, C. J. & Soudijn, W. Effects of halopemide on GABA receptor binding, uptake and release. *Brain Research* 210, 485-492 (1981).
32. Hansen, M., Chae, H. S. & Kieber, J. J. Regulation of ACS protein stability by cytokinin and brassinosteroid. *Plant J,* 9, doi:10.1111/j.1365-313x.2008.03711.x (2008).
33. Mazur, H., Konop, A. & Synak, R. Indole-3-acetic acid in the culture medium of two axenic green microalgae. *J. Appl. Phycol.* (2001).
34. Piotrowska, Czerpak, Pietryczuk, Olesiewicz & Wedolowska. The effect of indomethacin on the growth and metabolism of green alga Chlorella vulgaris Beijerinck. *Plant Growth Regul* 55, 125-136, doi:10.1007/s10725-008-9267-6 (2008).
35. Bishop, D. G. & Smillie, R. M. The effect of chloramphenicol and cycloheximide on lipid synthesis during chloroplast development in Euglena gracilis. *Arch Biochem Biophys* 139, 179-189 (1970).
36. Nakai, S., Inoue, Y. & Hosomi, M. Algal growth inhibition effects and inducement modes by plant-producing phenols. *Water Research* 35, 1855-1859, doi:10.1016/s0043-1354(00)00444-9 (2001).
37. Wang, X. & Tian, W. Green Tea Epigallocatechin Gallate: A Natural Inhibitor of Fatty-Acid Synthase. *Biochem. Biophys. Res. Commun.* 288, 1200-1206, doi:10.1006/bbrc.2001.5923 (2001).
38. Lambert, J. D. & Yang, C. S. Mechanisms of Cancer Prevention by Tea Constituents. *The Journal of Nutrition* 133, 3262S-3267S (2003).
39. Saffari, Y. & Sadrzadeh, S. M. H. Green tea metabolite EGCG protects membranes against oxidative damage in vitro. *Life Sci.* 74, 1513-1518, doi:10.1016/j.lfs.2003.08.019 (2004).
40. Williams, A. C. & Barry, B. W. Penetration enhancers. *Advanced Drug Delivery Reviews* 56, 603-618, doi: 10.1016/j.addr.2003.10.025 (2004).
41. McNeil, S. D., Nuccio, M. L. & Hanson, A. D. Betaines and Related Osmoprotectants. Targets for Metabolic Engineering of Stress Resistance. *Plant Physiology* 120, 945-949, doi:10.1104/pp. 120.4.945 (1999).
42. Sanmartín-Suárez, C., Soto-Otero, R., Sánchez-Sellero, I. & Méndez-Álvarez, E. Antioxidant properties of dimethyl sulfoxide and its viability as a solvent in the evaluation of neuroprotective antioxidants. *J. Pharmacol. Toxicol. Methods* 63, 209-215, doi:10.1016/j.vascn.2010.10.004.
43. De La Vega, F. M. & Mendoza-Figueroa, T. Dimethyl sulfoxide enhances lipid synthesis and secretion by long-term cultures of adult rat hepatocytes. *Biochimie* 73, 621-624, doi:10.1016/0300-9084(91)90033-w (1991).
44. Lee, P. A. & De Mora, S. J. Intracellular dimethylsulfoxide (DMSO) in unicellular marine algae: speculations on its origin and possible biological role. *J Phycol* 35, 8-18, doi:10.1046/j.1529-8817.1999.3510008.x (1999).
45. Sunda, W., Kieber, D. J., Kiene, R. P. & Huntsman, S. An antioxidant function for DMSP and DMS in marine algae. *Nature* 418, 317-320, 2002.
46. Merrett, M. J., Nimer, N. A. & Dong, L. F. The utilization of bicarbonate ions by the marine microalga Nannochloropsis oculata (Droop) Hibberd. *Plant, Cell & Environment* 19, 478-484, doi:10.1111/j.1365-3040.1996.tb00340.x (1996).
47. Gurtovenko, A. A. & Anwar, J. Modulating the Structure and Properties of Cell Membranes: The Molecular Mechanism of Action of Dimethyl Sulfoxide. *The Journal of Physical Chemistry B* 111, 10453-10460, doi:10.1021/jp073113e (2007).
48. Lemieux, G. A. et al. A whole-organism screen identifies new regulators of fat storage. *Nat Chem Biol* 7, 206-213, 2011.
49. Baniecki, M. L., Wirth, D. F. & Clardy, J. High-Throughput Plasmodium falciparum Growth Assay for Malaria Drug Discovery. *Antimicrob. Agents Chemother.* 51, 716-723, doi:10.1128/AAC.01144-06 (2007).

50 Kaufman, C. K., White, R. M. & Zon, L. Chemical genetic screening in the zebrafish embryo. *Nat. Protocols* 4, 1422-1432 (2009).

51 Huang, J. et al. Finding new components of the target of rapamycin (TOR) signaling network through chemical genetics and proteome chips. *Proceedings of the National Academy of Sciences of the United States of America* 101, 16594-16599, doi:10.1073/pnas.0407117101 (2004).

52 Bowler, C. et al. The Phaeodactylum genome reveals the evolutionary history of diatom genomes. *Nature* 456, 239-244 (2008).

53 Knothe, G. "Designer" Biodiesel: Optimizing Fatty Ester Composition to Improve Fuel Properties. *Energy & Fuels* 22, 1358-1364, doi:10.1021/ef700639e (2008).

54 Matsusue, K., Ishii, Y., Ariyoshi, N. & Oguri, K. A highly toxic PCB produces unusual changes in the fatty acid composition of rat liver. *Toxicology Letters* 91, 99-104, doi: 10.1016/s0378-4274(97)03881-2 (1997).

55 Bligh, E. G. & Dyer, W. J. A rapid method of total lipid extraction and purification. *Can J Physiol Pharmacol* 37, 911-917 (1959).

56 Folch, J., Lees, M. & Stanley, G. H. S. A simple method for the isolation and purification of total lipides from animal tissues. *J. Biol. Chem.* 226, 497-509 (1957).

57 Lee, J.-Y Yoo, C., Jun, S.-Y., Ahn, C.-Y. & Oh, H.-M. Comparison of several methods for effective lipid extraction from microalgae. *Bioresour. Technol.* 101, S75-S77, doi:10.1016/j.biortech.2009.03.058 (2010).

58 Guckert, J., Cooksey, K. & Jackson, L. Lipid sovent systems are not equivalent for analysis of lipid classes in the microeukaryotic green alga, *Chlorella. J. Microbiol. Methods* 8, 139-149 (1988).

59 Iverson, S., Lang, S. & Cooper, M. Comparison of the bligh and dyer and folch methods for total lipid determination in a broad range of marine tissue. *Lipids* 36, 1283-1287, doi:10.1007/s11745-001-0843-0 (2001).

60 Cooney, M., Young, G. & Nagle, N. Extraction of bio-oils from microalgae. *Sep Purif Rev* 38, 291-325, doi:info:doi/10.1080/15422110903327919 (2009).

61 Picariello, G., Paduano, A., Sacchi, R. & Addeo, F. MALDI-TOF Mass spectrometry profiling of polar and nonpolar fractions in heated vegetable oils. *J. Agric. Food Chem.* 57, 5391-5400, doi:10.1021/jf9008795 (2009).

References for Example 3

1. Hu, Q., Sommerfeld, M., Jarvis, E., Ghirardi, M., Posewitz, M., Seibert, M., and Darzins, A. (2008) Microalgal triacylglycerols as feedstocks for biofuel production: perspectives and advances, *Plant J.* 54, 621-639.
2. Wijffels, R. H., and Barbosa, M. J. (2010) An Outlook on Microalgal Biofuels, Science 329, 796-799.
3. Sheehan, J., Dunahay, T., Benemann, J., and Roessler, P. (1998) A look back at the US Department of Energy's Aquatic Species program—Biodiesel from Algae, *National Renewable Energy Laboratory*, 328.
4. Chisti, Y. (2007) Biodiesel from microalgae, *Biotechnol. Adv.* 25, 294-306.
5. Suen, Y., Hubbard, J. S., Holzer, G., and Tornabene, T. G. (1987) Total lipid production of the green alga *Nannochloropsis* sp. qII under different nitrogen regimes, *J. Phycol.* 23, 289-296.
6. Cerón Garcia, M. C., Sánchez Mirón, A., Fernandez Sevilla, J. M., Molina Grima, E., and Garcia Camacho, F. (2005) Mixotrophic growth of the microalga *Phaeodactylum tricornutum*: Influence of different nitrogen and organic carbon sources on productivity and biomass composition, *Process Biochem.* 40, 297-305.
7. Kilian, O., Benemann, C. S. E., Niyogi, K. K., and Vick, B. (2011) High-efficiency homologous recombination in the oil-producing alga *Nannochloropsis* sp, *Proc. Natl. Acad. Sci.* 108, 21265-21269.
8. Boussiba, S., Vonshak, A., Cohen, Z., Avissar, Y., and Richmond, A. (1987) Lipid and biomass production by the halotolerant microalga *Nannochloropsis salina*, Biomass 12, 37-47.
9. Yu, W.-L., Ansari, W., Schoepp, N., Hannon, M., Mayfield, S., and Burkart, M. (2011) Modifications of the metabolic pathways of lipid and triacylglycerol production in microalgae, *Microb. Cell Fact.* 10, 91-102.
10. Roesler, K., Shintani, D., Savage, L., Boddupalli, S., and Ohlrogge, J. (1997) Targeting of the *Arabidopsis* homomeric acetyl-coenzyme A carboxylase to plastids of rapeseeds, *Plant Physiol.* 113, 75-81.
11. Dehesh, K., Tai, H., Edwards, P., Byrne, J., and Jaworski, J. (2001) Overexpression of 3-ketoacyl-acyl-carrier protein synthase IIIs in plants reduces the rate of lipid synthesis, *Plant Physiol.* 125, 1103-1114.
12. Vigeolas, H., and Geigenberger, P. (2004) Increased levels of glycerol-3-phosphate lead to a stimulation of flux into triacylglycerol synthesis after supplying glycerol to developing seeds of *Brassica napus* L. in planta, *Planta* 219, 827-835.
13. Vigeolas, H., Waldeck, P., Zank, T., and Geigenberger, P. (2007) Increasing seed oil content in oil-seed rape (*Brassica napus* L.) by over-expression of a yeast glycerol-3-phosphate dehydrogenase under the control of a seed-specific promoter, *Plant Biotechnol. J.* 5, 431-441.
14. Jain, R., Coffey, M., Lai, K., Kumar, A., and MacKenzie, S. (2000) Enhancement of seed oil content by expression of glycerol-3-phosphate acyltransferase genes, *Biochem. Soc. Trans.* 28, 958-961.
15. Zou, J., Katavic, V., Giblin, E., Barton, D., MacKenzie, S., Keller, W., Hu, X., and
Taylor, D. (1997) Modification of seed oil content and acyl composition in the Brassicaceae by expression of a yeast sn-2 acyltransferase gene, *Plant Cell* 9, 909-923.
16. Wang, Z. T., Ullrich, N., Joo, S., Waffenschmidt, S., and Goodenough, U. (2009) Algal Lipid Bodies: Stress Induction, Purification, and Biochemical Characterization in Wild-Type and Starchless *Chlamydomonas reinhardtii*, *Eukaryot. Cell* 8, 1856-1868.
17. Siaut, M., Cuine, S., Cagnon, C., Fessler, B., Nguyen, M., Carrier, P., Beyly, A., Beisson, F., Triantaphylides, C., Li-Beisson, Y., and Peltier, G. (2011) Oil accumulation in the model green alga *Chlamydomonas reinhardtii*: characterization, variability between common laboratory strains and relationship with starch reserves, *BMC Biotechnol.* 11, 7-21.
18. Li, Y., Han, D., Hu, G., Sommerfeld, M., and Hu, Q. (2010) Inhibition of starch synthesis results in overproduction of lipids in *Chlamydomonas reinhardtii*, *Biotechnol. Bioeng.* 107, 258-268.
19. Moellering, E. R., and Benning, C. (2010) RNA Interference Silencing of a Major Lipid
Droplet Protein Affects Lipid Droplet Size in *Chlamydomonas reinhardtii*, *Eukaryot. Cell* 9, 97-106.
20. Molnar, A., Bassett, A., Thuenemann, E., Schwach, F., Karkare, S., Ossowski, S., Weigel, D., and Baulcombe, D. (2009) Highly specific gene silencing by artificial microRNAs in the unicellular alga *Chlamydomonas reinhardtii*, *Plant J.* 58, 165-174.
21. Schreiber, S. L. (2005) Small molecules: the missing link in the central dogma, *Nat Chem Biol* 1, 64-66.

22. Walsh, D. P., and Chang, Y.-T. (2006) Chemical Genetics, *Chem. Rev.* 106, 2476-2530.
23. Stockwell, B. R. (2004) Exploring biology with small organic molecules, *Nature* 432, 846-854.
24. Lemieux, G. A., Liu, J., Mayer, N., Bainton, R. J., Ashrafi, K., and Werb, Z. (2011) A whole-organism screen identifies new regulators of fat storage, *Nat. Chem. Biol.* 7, 206-213.
25. Kaufman, C. K., White, R. M., and Zon, L. (2009) Chemical genetic screening in the zebrafish embryo, *Nature Protocols* 4, 1422-1432.
26. Burns, A. R., Kwok, T. C. Y., Howard, A., Houston, E., Johanson, K., Chan, A., Cutler,
S. R., McCourt, P., and Roy, P. J. (2006) High-throughput screening of small molecules for bioactivity and target identification in *Caenorhabditis elegans, Nature Protocols* 1, 1906-1914.
27. Blackwell, H. E., and Zhao, Y. (2003) Chemical genetic approaches to plant biology, *Plant Physiol* 133, 448-455.
28. Maucourt, K., Agarwal, M., René, B., and Fermandjian, S. (2002) Use of *Chlamydomonas reinhardtii* mutants for anticancer drug screening, *Biochem. Pharmacol.* 64, 1125-1131.
29. Avasthi, P., Marley, A., Lin, H., Gregori-Puigjane, E., Shoichet, B. K., von Zastrow, M., and Marshall, W. F. (2012) A Chemical Screen Identifies Class A G-Protein Coupled Receptors As Regulators of Cilia, *ACS Chem. Biol.* 7, 911-919.
30. Chen, W., Zhang, C., Song, L., Sommerfeld, M., and Hu, Q. (2009) A high throughput Nile red method for quantitative measurement of neutral lipids in microalgae, *J. Microbiol. Meth.* 77, 41-47.
31. Danielewicz, M. A., Anderson, L. A., and Franz, A. K. (2011) Triacylglycerol profiling of marine microalgae by mass spectrometry, *J. Lipid Res.* 52, 2101-2108.
32. Knothe, G. (2009) Improving biodiesel fuel properties by modifying fatty ester composition, *Energy Environ. Sci.* 2, 759-766.
33. White, D. A., Pagarette, A., Rooks, P., and Ali, S. T. (2012) The effect of sodium bicarbonate supplementation on growth and biochemical composition of marine microalgae cultures, *J. Appl. Phycol.*, 1-13.
34. Gardner, R. D., Cooksey, K. E., Mus, F., Macur, R., Moll, K., Eustance, E., Carlson, R. P., Gerlach, R., Fields, M. W., and Peyton, B. M. (2012) Use of sodium bicarbonate to stimulate triacylglycerol accumulation in the chlorophyte *Scenedesmus* sp. and the diatom *Phaeodactylum tricornutum, J. Appl. Phycol.* 24, 1311-1320.
35. Mazur, H., Konop, A., and Synak, R. (2001) Indole-3-acetic acid in the culture medium of two axenic green microalgae, *J. Appl. Phycol.* 13, 35-42.
36. Piotrowska, Czerpak, Pietryczuk, Olesiewicz, and Wedolowska. (2008) The effect of indomethacin on the growth and metabolism of green alga *Chlorella vulgaris* Beijerinck, *Plant Growth Regul* 55, 125-136.
37. Bishop, D. G., and Smillie, R. M. (1970) The effect of chloramphenicol and cycloheximide on lipid synthesis during chloroplast development in *Euglena gracilis, Arch. Biochem. Biophys.* 139, 179-189.
38. Schimmel, R. J. (1984) Stimulation of cAMP accumulation and lipolysis in hamster adipocytes with forskolin, *Am. J. Physiol.—Cell Ph.* 246, C63-C68.
39. Jay, A. (1996) Effects of organic solvents and solvent-atrazine interactions on two algae, *Chlorella vulgaris* and *Selenastrum capricornutum, Arch. Environ. Contam. Toxicol.* 31, 84-90.
40. Gurtovenko, A. A., and Anwar, J. (2007) Modulating the Structure and Properties of Cell Membranes: The Molecular Mechanism of Action of Dimethyl Sulfoxide, *J. Phys. Chem. B* 111, 10453-10460.
41. McNeil, S. D., Nuccio, M. L., and Hanson, A. D. (1999) Betaines and Related Osmoprotectants. Targets for Metabolic Engineering of Stress Resistance, *Plant Physiol.* 120, 945-949.
42. Sanmartin-Suarez, C., Soto-Otero, R., Sanchez-Sellero, I., and Mendez-Alvarez, E. Antioxidant properties of dimethyl sulfoxide and its viability as a solvent in the evaluation of neuroprotective antioxidants, *J. Pharmacol. Toxicol. Methods* 63, 209-215.
43. De La Vega, F. M., and Mendoza-Figueroa, T. (1991) Dimethyl sulfoxide enhances lipid synthesis and secretion by long-term cultures of adult rat hepatocytes, *Biochimie* 73, 621-624.
44. Lee, P. A., and de Mora, S. J. (1999) Intracellular Dimethylsulfoxide (DMSO) in Unicellular Marine Algae: Speculations on Its Origin and Possible Biological Role, *J. Phycol.* 35, 8-18.
45. Sunda, W., Kieber, D. J., Kiene, R. P., and Huntsman, S. (2002) An antioxidant function for DMSP and DMS in marine algae, *Nature* 418, 317-320.
46. Okumura, Y., Koyama, J., Takaku, H., and Satoh, H. (2001) Influence of Organic Solvents on the Growth of Marine Microalgae, *Arch. Environ. Contam. Toxicol.* 41, 123-128.
47. Wang, X., and Tian, W. (2001) Green Tea Epigallocatechin Gallate: A Natural Inhibitor of Fatty-Acid Synthase, *Biochem. Biophys. Res. Commun.* 288, 1200-1206.
48. Kamiyama, O., Sanae, F., Ikeda, K., Higashi, Y., Minami, Y., Asano, N., Adachi, I., and
Kato, A. (2010) In vitro inhibition of α-glucosidases and glycogen phosphorylase by catechin gallates in green tea, *Food Chem.* 122, 1061-1066.
49. Saffari, Y., and Sadrzadeh, S. M. H. (2004) Green tea metabolite EGCG protects membranes against oxidative damage in vitro, *Life Sci.* 74, 1513-1518.
50. Foyer, C. H., and Shigeoka, S. (2011) Understanding Oxidative Stress and Antioxidant Functions to Enhance Photosynthesis, *Plant Physiol.* 155, 93-100.
51. Ledford, H. K., and Niyogi, K. K. (2005) Singlet oxygen and photo-oxidative stress management in plants and algae, *Plant Cell Environ.* 28, 1037-1045.
52. Tanaka, S., Ikeda, K., Miyasaka, H., Shioi, Y., Suzuki, Y., Tamoi, M., Takeda, T., Shigeoka, S., Harada, K., and Hirata, K. (2011) Comparison of three *Chlamydomonas* strains which show distinctive oxidative stress tolerance, *J. Biosci. Bioeng.* 112, 462-468.
53. Georgianna, D. R., and Mayfield, S. P. (2012) Exploiting diversity and synthetic biology for the production of algal biofuels, *Nature* 488, 329-335.
54. León-Bañares, R. (2004) Transgenic microalgae as green cell-factories, *Trends Biotechnol.* 22, 45-52.
56. Folch, J., Lees, M., and Sloane Stanley, G. H. (1957) A simple method for the isolation and purification of total lipides from animal tissues, *J. Biol. Chem.* 226, 497-509.
57. Lee, J.-Y., Yoo, C., Jun, S.-Y., Ahn, C.-Y., and Oh, H.-M. (2010) Comparison of several methods for effective lipid extraction from microalgae, *Bioresour. Technol.* 101, S75-S77.

We claim:
1. A method of increasing lipid levels in an algal cell population, comprising:
   contacting an algal cell population with at least one compound in an amount sufficient to increase lipid levels in said cell population, wherein said at least one compound comprises an antioxidant compound, and does not inhibit fatty acid metabolism.

2. The method of claim 1, wherein the antioxidant compound comprises at least one from the group consisting of resveratrol, (+)-catechin, (−)-epicatechin gallate, (−)-epigallocatechin, (−)-epigallocatechin gallate, butylated hydroxyanisole (BHA), propyl gallate, ascorbic acid, N,N'-di-sec-butyl-p-phenylenediamine, α-D-tocopherol, chlorogenic acid, luteolin, cytochrome P450 1B1 inhibitor, and quercetin.

3. The method of claim 1, wherein the at least one compound is derived from a composition selected from the group consisting of a plant extract, a fruit extract, grape pomace, olive pomace, and tea extract.

4. The method of claim 1, wherein the at least one compound comprises two, three, four, or five compounds.

5. The method of claim 1, wherein the at least one compound is present in an amount sufficient to increase growth rate of the cell population.

6. The method of claim 1, wherein the cell population is grown under nutrient-deficient conditions.

7. The method of claim 1, wherein the at least one compound is present in an amount sufficient to decrease growth rate of the cell population.

8. The method of claim 1, wherein the cell population is contacted with the at least one compound during lag growth phase.

9. The method of claim 1, wherein the cell population is contacted with the at least one compound during exponential growth phase.

10. The method of claim 1, wherein the increased lipid levels comprise increased triacylglycerol levels.

11. The method of claim 1, wherein lipid levels in the cell population are increased by 40% to 400% as compared to a corresponding cell population not contacted with the at least one compound.

12. The method of claim 1, further comprising producing a biofuel from the lipids.

13. A method of producing saturated or monounsaturated triacylglycerols in an algal cell population, comprising:
contacting an algal cell population with at least one compound in an amount sufficient to induce production of one or more saturated or monounsaturated triacylglycerols in said cell population, wherein said at least one compound comprises an antioxidant compound.

14. The method of claim 1, wherein the antioxidant compound comprises at least one from the group consisting of resveratrol, (+)-catechin, (−)-epicatechin gallate, (−)-epigallocatechin, (−)-epigallocatechin gallate, butylated hydroxyanisole (BHA), propyl gallate, α-D-tocopherol, chlorogenic acid, luteolin, cytochrome P450 1B1 inhibitor, and quercetin.

15. The method of claim 1, wherein the antioxidant compound comprises butylated hydroxyanisole (BHA).

16. The method of claim 13, wherein the antioxidant compound comprises at least one from the group consisting of resveratrol, (+)-catechin, (−)-epicatechin gallate, (−)-epigallocatechin, (−)-epigallocatechin gallate, butylated hydroxyanisole (BHA), propyl gallate, α-D-tocopherol, chlorogenic acid, luteolin, cytochrome P450 1B1 inhibitor, and quercetin.

17. The method of claim 13, wherein the antioxidant compound comprises butylated hydroxyanisole (BHA).

* * * * *